US012673926B2

(12) United States Patent
Kjær et al.

(10) Patent No.: US 12,673,926 B2
(45) Date of Patent: Jul. 7, 2026

(54) TETRAZINE COMPOUNDS FOR IN VIVO IMAGING

(71) Applicants: KØBENHAVNS UNIVERSITET, Copenhagen K (DK); RIGSHOSPITALET, Copenhagen Ø (DK)

(72) Inventors: Andreas Kjær, Frederiksberg (DK); Ida Nymann Petersen, Copenhagen Ø (DK); Matthias Manfred Herth, Malmö (SE); Jesper Langgard Kristensen, Copenhagen N (DK)

(73) Assignees: Københavns Universitet, Copenhagen K (DK); Rigshospitalet, Copenhagen Ø (DK)

( * ) Notice: Subject to any disclaimer, the term of this patent is extended or adjusted under 35 U.S.C. 154(b) by 1411 days.

(21) Appl. No.: 17/297,924

(22) PCT Filed: Nov. 29, 2019

(86) PCT No.: PCT/DK2019/050374
§ 371 (c)(1),
(2) Date: May 27, 2021

(87) PCT Pub. No.: WO2020/108720
PCT Pub. Date: Jun. 4, 2020

(65) Prior Publication Data
US 2022/0119359 A1     Apr. 21, 2022

(30) Foreign Application Priority Data
Nov. 30, 2018    (DK) ........................... PA 2018 70791

(51) Int. Cl.
A61K 9/00      (2006.01)
A61K 51/04     (2006.01)
(Continued)

(52) U.S. Cl.
CPC .......... *C07D 257/08* (2013.01); *A61K 51/044* (2013.01); *C07D 401/04* (2013.01)

(58) Field of Classification Search
CPC .................................................... A61K 51/044
See application file for complete search history.

(56) References Cited

U.S. PATENT DOCUMENTS 3,863,010 A      1/1975  Lang, Jr. et al.

FOREIGN PATENT DOCUMENTS

| | | |
|---|---|---|
| WO | WO 2012/012612 A2 | 1/2012 |
| WO | WO 2014/065860 A1 | 5/2014 |
| WO | WO 2017/093263 A1 | 6/2017 |

OTHER PUBLICATIONS

Mboyi, Building Diversity in ortho-Substituted s-Aryltetrazines by Tuning N-Directed Palladium C—H Halogenation: Unsymmetrical Polyhalogenated and Biphenyl s-Aryltetrazines ACS Catal. 2017, 7, 8493-8501 (Year: 2017).*

(Continued)

*Primary Examiner* — Paul W Dickinson
(74) *Attorney, Agent, or Firm* — Foley & Lardner LLP

(57)       ABSTRACT

The present invention relates to novel tetrazine compounds of formula I, wherein one of $R_1$-$R_5$ is $^{18}F$, for use in pretargeted in vivo imaging. The compounds are suitable for use in click chemistry, i.e. reactions that join a targeting molecule and a reporter molecule. The invention further (Continued)

relates to precursors to formula I, wherein one of $R_1$-$R_5$ is $SnR_3$, $B(OR)_2$, $B(OH)_2$. Formula (I).

(I)

19 Claims, 10 Drawing Sheets

(51) Int. Cl.
    *C07D 257/08*     (2006.01)
    *C07D 401/04*     (2006.01)

(56)                References Cited

OTHER PUBLICATIONS

Denk, Development of a 18F-Labeled Tetrazine with Favorable Pharmacokinetics for Bioorthogonal PET Imaging, Angew. Chem. Int. Ed. 2014, 53, 9655-9659 (Year: 2014).*

Knorr et al., "Bioorthogonally Applicable Fluorogenic Cyanine-Tetrazines for No-Wash Super-Resolution Imaging," Bioconjugate Chemistry, vol. 29, pp. 1312-1318 (2018).

Testa, Christelle et al.; "Ortho-Functionalized Aryltetrazines by Direct Palladium-Catalyzed C—H Halogenation: Application to Fast Electrophilic Fluorination Reactions"; Angew. Chem. Int. Ed., vol. 55; Mar. 24, 2016; pp. 5555-5559.

* cited by examiner

Figure 2
PET images with compound [$^{18}$F]9 in bones (knee) and a control region (the heart)
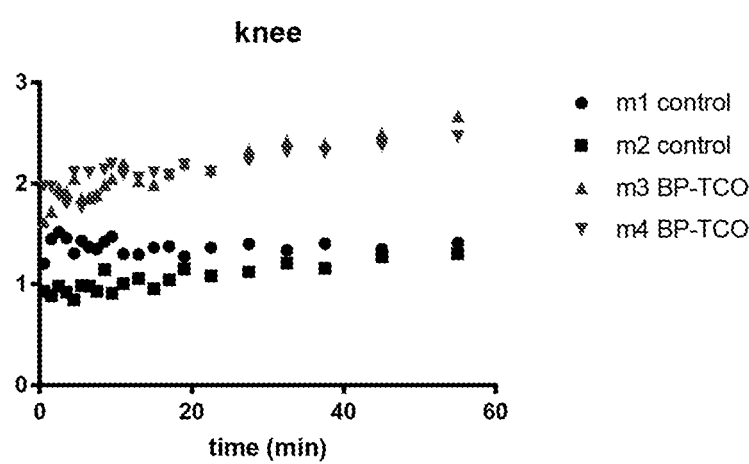
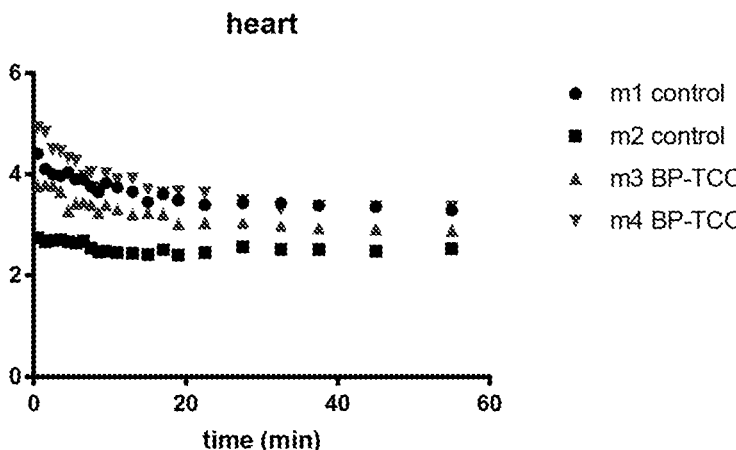

Figure 4 HPLC chromatograms compound [$^{18}$F]6
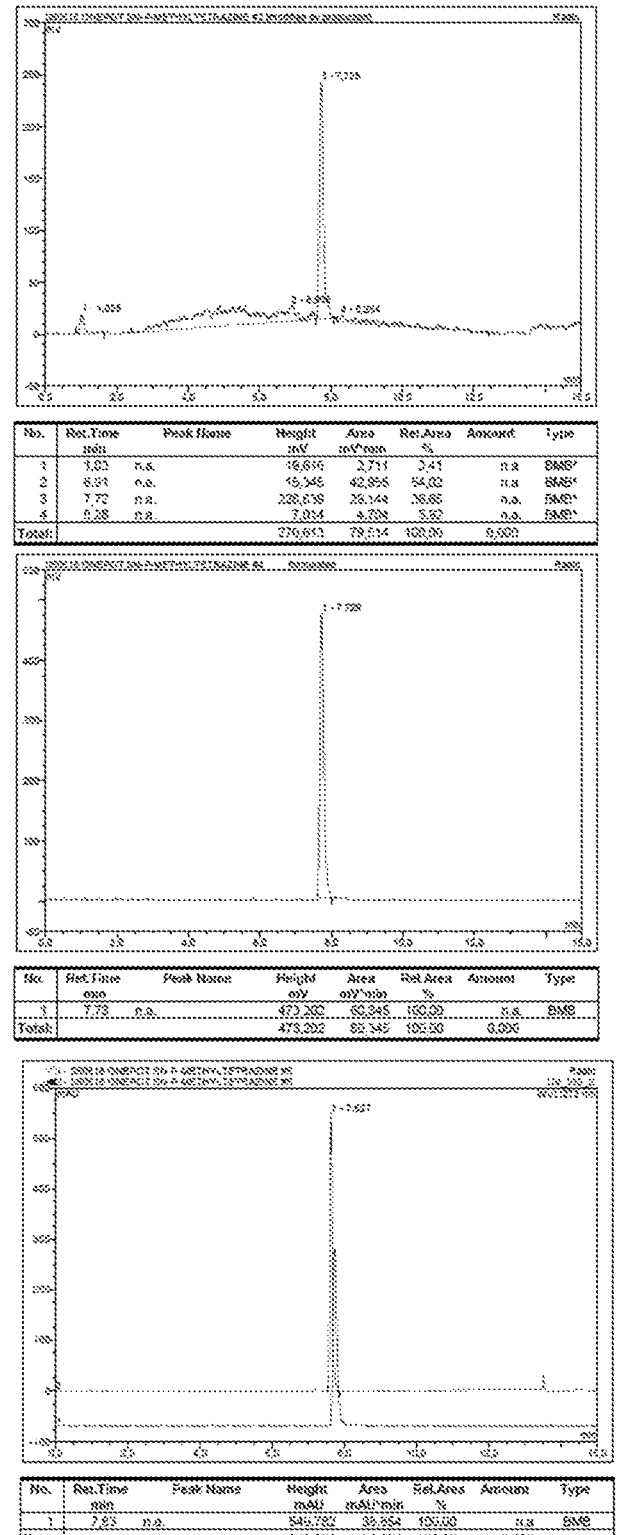

Figure 5 HPLC chromatograms compound [$^{18}$F]7
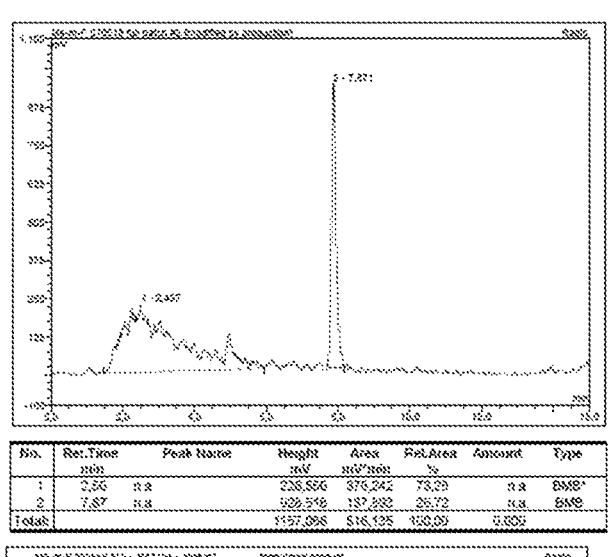
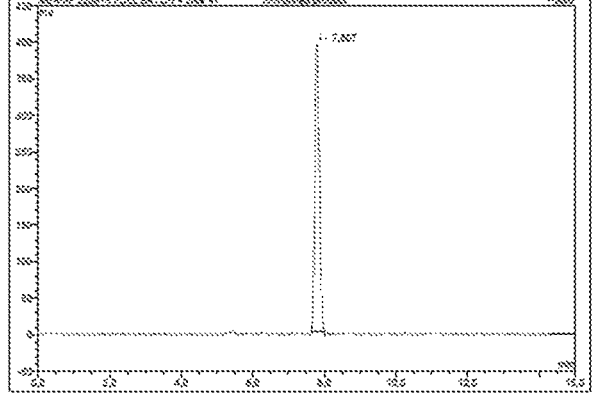
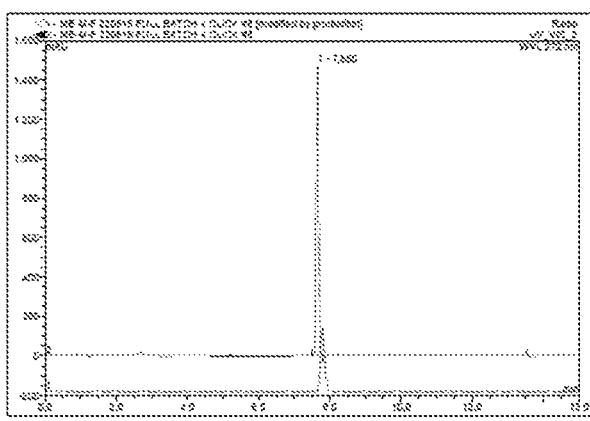

Figure 6 HPLC chromatograms compound [¹⁸F]8
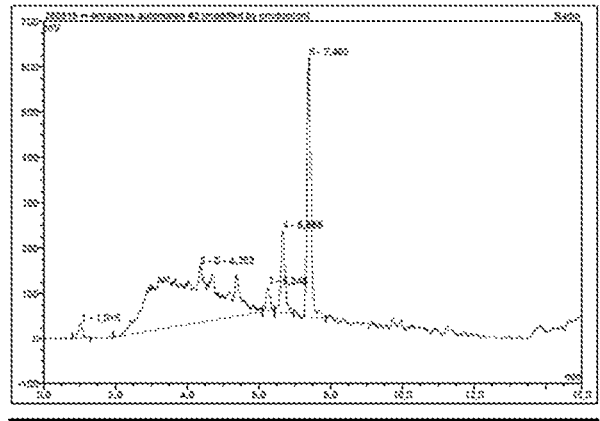
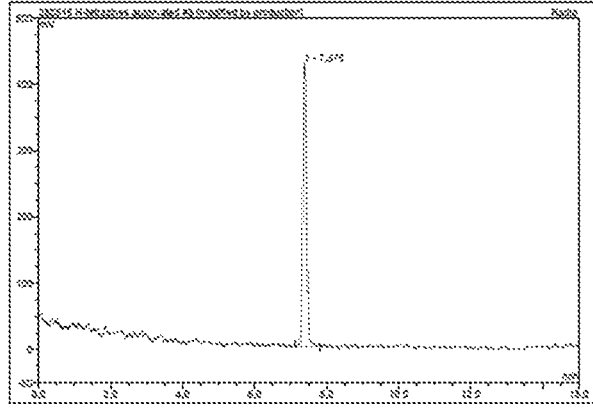
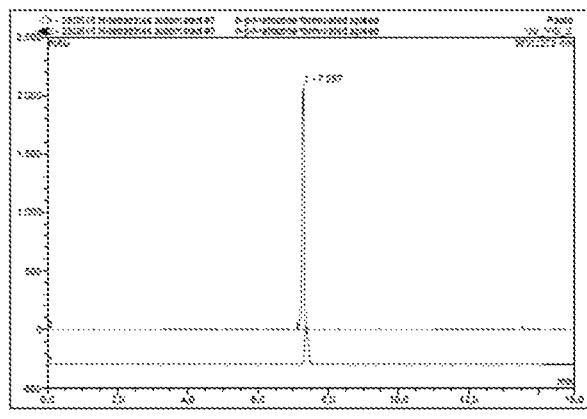

Figure 7 HPLC chromatograms compound [$^{18}$F]9
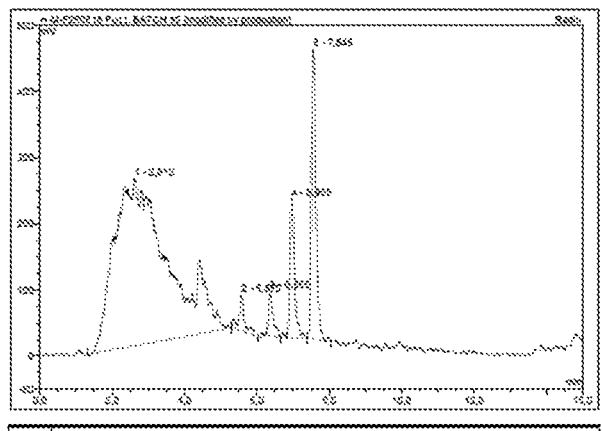
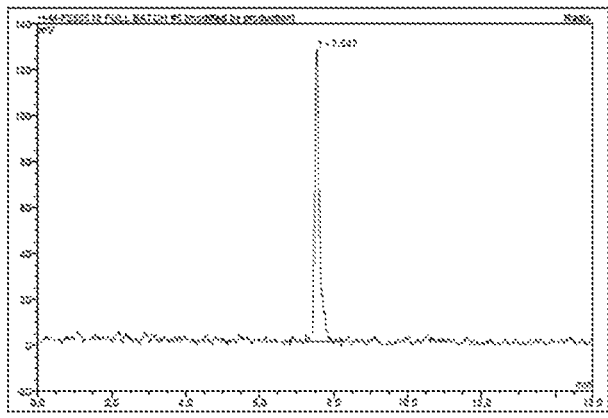
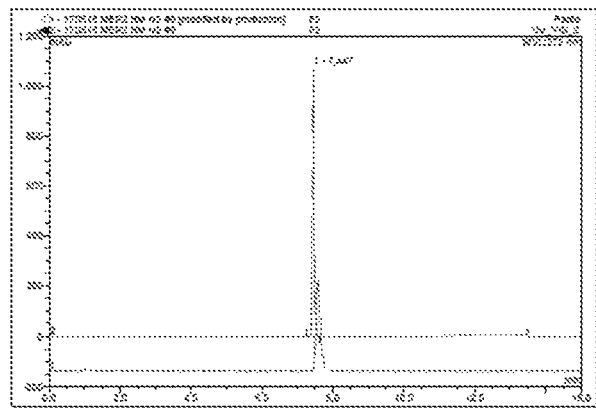

Figure 8-I preferred compounds

Figure 8-II preferred compounds

| RCC [%] | 30 | 28 | 30 | 25 | ✕ | 18 | ✕ | 11 |

TETRAZINE COMPOUNDS FOR IN VIVO IMAGING

CROSS-REFERENCE TO RELATED APPLICATIONS

The present application is the U.S. National Stage of International Application No. PCT/DK2019/050374, filed Nov. 29, 2019, and claims priority to Denmark Patent Application No. PA 2018 70791, filed Nov. 30, 2018.

"The project leading to this patent application has received funding from the European Union's Horizon 2020 research and innovation programme under grant agreement No 668532."

FIELD OF THE INVENTION

The present invention is within the field of bioorthogonal chemistry and relates to novel tetrazine compounds for use in pretargeted in vivo imaging. The compounds are suitable for use in click chemistry, i.e. reactions that join a targeting molecule and a reporter molecule.

BACKGROUND OF THE INVENTION

Click chemistry has emerged as a versatile tool for pretargeted imaging, radiotherapy and recently also for specific drug release in vivo. Click chemistry is of particular interest in bioorthogonal chemistry.

Bioorthogonal chemistry refers to any chemical reaction that can occur inside living systems without interfering with native biochemical processes. A pretargeting strategy makes use of bioorthogonal chemistry and proceeds in two steps. A first step is where a substrate is modified with a bioorthogonal functional group (denoted chemical reporter or target vector) and introduced to the patient. Normally, a substrate can be a metabolite, an enzyme inhibitor, monoclonal antibody, nanomedicine, polymer, nanoparticle, etc. The second step is where a probe, that contains the complementary functional group, is introduced and reacts and labels the substrate. The probe is a small effector molecule carrying the label (payload). FIG. 1 displays the principle.

Especially, the tetrazine ligation based on highly reactive tetrazines (Tzs) and trans-cyclooctenes (TCO's)) has been investigated as candidates for pretargeted strategies due to their extremely rapid reaction kinetics sans catalyst.

WO2012012612 describes the Tetrazine-trans-cyclooctene system and the synthesis of three 18F tetrazines. However, their low yield led to the conclusion that the 18F labelling should be on the trans cyclooctene. The present invention has overcome the yield challenges in WO2012012612 and various new compounds have been invented.

As mentioned above, a pretargeted strategy involves a vector tagged with a reactive moiety. The vector accumulates at the target site after administration. Subsequently, a small effector molecule carrying a payload of interest (e.g. a radiolabelled probe) is administered. A ligation reaction (click chemistry) between the targeting vector and the small effector molecule carrying the payload takes place in vivo, whereby the payload is coupled to the target of interest.

When target vectors such as monoclonal antibodies (mAbs), polymers or nanoparticles (NPs) are applied, advantages in respect to nuclear medicine applications can be obtained. The advantages include improved imaging contrast (up to 100-fold when additional blood circulating targeting vector is deactivated or removed), lower radiation burden to healthy tissue, and maximized therapeutic doses within the target region compared to more traditional approaches. The advantages are mainly a result of a two-step process, where the first step is the slow targeting process of the vector and the second step is a rapid targeting process of the payload.

Positron-Emission-Tomography (PET) is a powerful and routinely used diagnostic imaging tool in precision medicine. This is because it is highly sensitive, it offers isotropism, and it is quantifiable, i.e. it can be used to quantify the amount of nanomedicine delivered to the target region. Fluorine-18 ($^{18}$F) is considered as the "gold standard" PET radionuclide for clinical applications. It is ideal because of its relatively short positron range (2.4 mm max. range in water), good branching ratio (96.7% positron decay) and its half-life ($t_{1/2}$=110 min), resulting in good resolution, relatively low radiation burden and ability to distribute within a several hundred kilometres range.

Consequently, in recent years there have been several efforts to develop $^{18}$F-imaging agents for tetrazine (Tz) ligation-based pretargeted imaging. Initially, TCO's have been explored for $^{18}$F-labeling strategies. However, it seems as if TCOs are better suited to be attached to the targeting vector itself rather than used as a small effector molecule.

Tzs with relatively low reactivity are suitable for $^{18}$F-aliphatic substitution ($S_N2$), whereas access to higher reactive and more clinically relevant structures was not reachable. To address this problem, multi-step synthon-based $^{18}$F-labeling procedures have been developed. However, none of these procedures appears to be optimal suited for clinical applications since multi-step procedures are usually challenging to set up for clinical routine.

Recently, chelator approaches to label Tz's with Al[$^{18}$F]F have been successfully explored. However, these strategies exclude most likely targets beyond cell membranes or the blood-brain-barrier since passive diffusion is limited due to the polar chelator character of these structures. Furthermore, targets that are located extracellular could be difficult to access since many targets internalize after binding of a TCO-functionalized targeting vector. Consequently, many targets associated with brain diseases such as the Alzheimer's disease or the Parkinson's disease cannot be imaged using pretargeted chelator-based approaches. Other targets such as the partly internalizing HER2-receptor can only be imaged with suboptimal targeting vector availability.

In conclusion, a rapid and convenient entry to highly activated directly $^{18}$F-labeled Tzs with clinically relevant reaction rates is still missing. Herein, we report the first approach that succeeds in such an attempt.

BRIEF DESCRIPTION OF THE FIGURES

FIG. 2 shows PET images with BP-TCO pretreated mice and controls, higher uptake can be detected with compound [$^{18}$F]9 in bones (knee) the target region of BP-TCOs compared to controls (upper), in a control region (the heart), where BP-TCO is not expected to bind, no differences could be detected between treated and non-treated mice;

FIG. 4 shows HPLC chromatograms for compound [$^{18}$F] 6;

FIG. 5 shows HPLC chromatograms for compound [$^{18}$F] 7;

FIG. 6 shows HPLC chromatograms for compound [$^{18}$F] 8;

3

4

Figure 9:
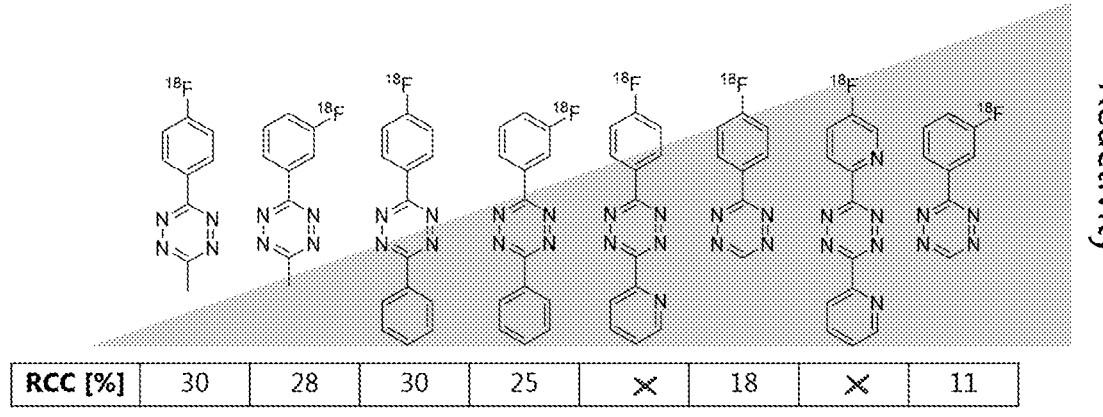

FIG. 7 shows HPLC chromatograms for compound [$^{18}$F] 9;

Figure 8:
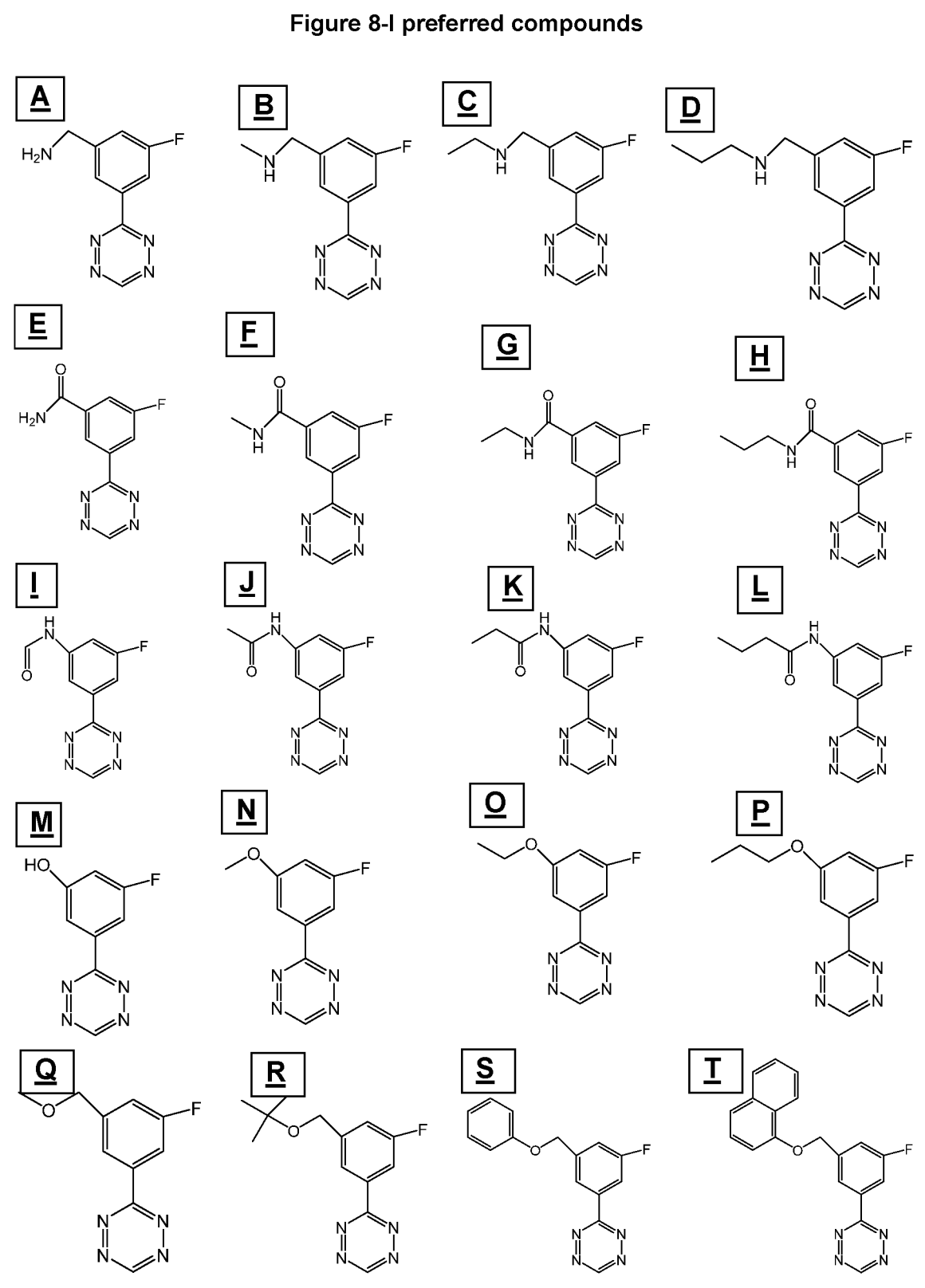
Figure 8:
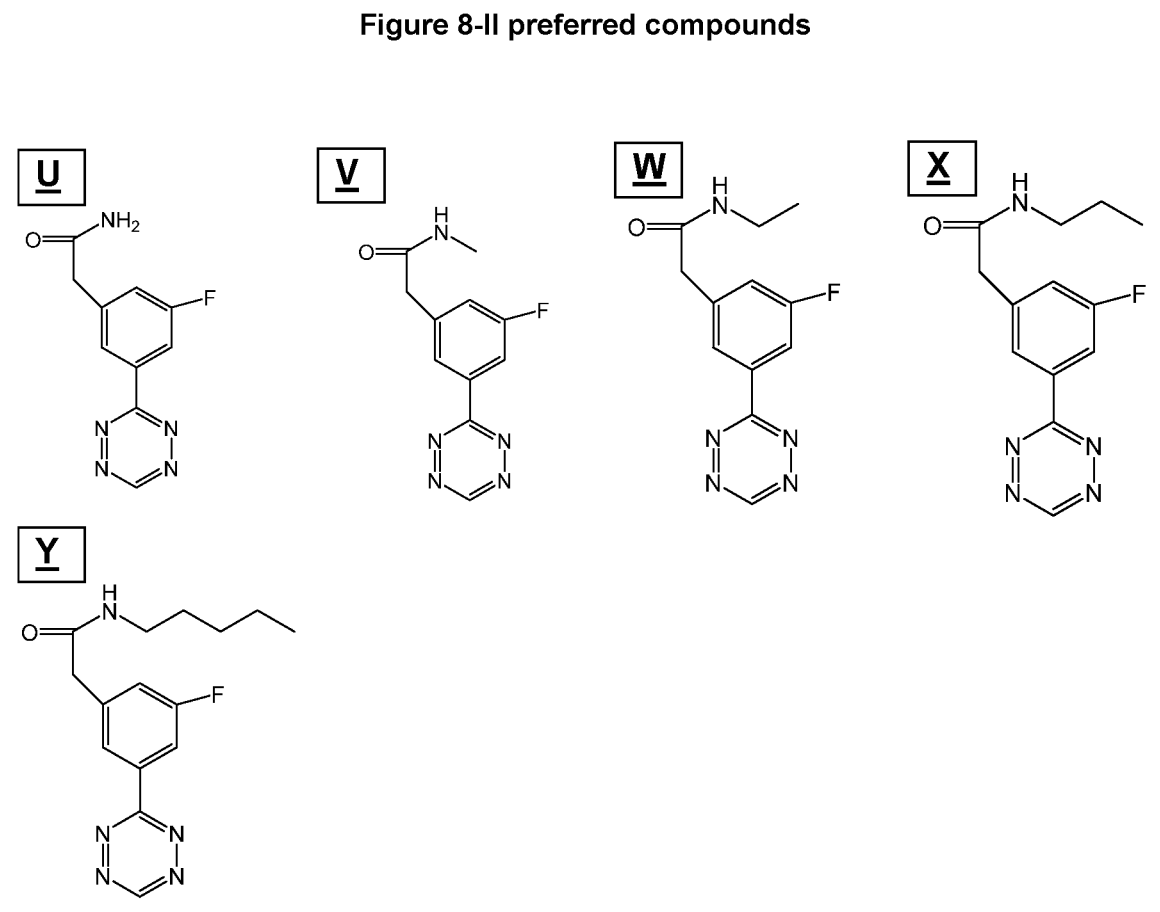

FIG. 8 (8-1 and 8-11) shows preferred compounds of the invention;

FIG. 9 shows the ranking of compounds according to the reactivity ranked according to their reactivity in the ligation reaction.

DETAILED DESCRIPTION OF THE INVENTION

The present invention provides $^{18}$F-labelled tetrazines suitable for use in bioorthogonal chemistry.

Bioorthogonal chemistry can be used in e.g. dose-finding studies. Dose-finding is an important part of the drug discovery process, i.e. how much of a putative new drug substance should be administered in the initial clinical investigations. If the dose is too low, one might not see the expected effects from the pre-clinical data, and if the dose is higher than needed, problems with side-effect might lead to the termination of a clinical program of good compounds. Thus, information about target engagement (which dose is needed for it to reach and engage the desired target to a certain degree) is crucial at an early stage.

The present invention relates to a tetrazine having the following formula I:

Formula I wherein one of $R_1$-$R_5$ is $^{18}$F, at least two of the remaining $R_1$-$R_5$ are H, and the other remaining $R_1$-$R_5$ are the same or different and are selected from H, alkyl, halogen, —CF$_3$, —CN, —O-alkyl, —S-alkyl, —NH-alkyl, —N(alkyl)$_2$, —NH(C═O)-alkyl, —N-alkyl-(C═O)-alkyl, —SO$_2$-alkyl, —SO$_2$—NH$_2$, —SO$_2$—NHalkyl, —SO$_2$—N(alkyl)$_2$, —C(═O)—NH$_2$, —C(═O)—NH-alkyl, —C(═O)—N(alkyl)$_2$, —C(═O)—OH, —C(═O)—O-alkyl, —CH$_2$—NH$_2$, —CH$_2$—NH-alkyl, —OH, CH$_2$—O-alkyl, CH$_2$—O-aryl, CH$_2$—O-phenyl, CH$_2$—O-naphthyl,

, wherein n is an integer from 1 to 4, and $R_6$ is selected from H, CH$_3$, phenyl, wherein the curly bond indicates the link to the tetrazine moiety.

In the present context, the term alkyl is intended to mean linear or branched C$_1$-C$_6$ alkyl, cyclic C$_1$-C$_6$ alkyl, optionally substituted with —OH, —NH$_2$ or halogen.

In the present context, the term halogen is intended to mean I, Br, Cl or F.

C$_1$-C$_6$ alkyl includes methyl, ethyl, propyl, isopropyl, butyl, sec. butyl, tert. butyl, pentyl and branched pentyl, hexyl and branched hexyl, and C$_3$-C$_6$ cyclic alkyl includes cyclopropyl, cyclobutyl, cyclopentyl, cyclohexyl.

Polyethylene glycol includes ethylene glycol (n=1) and polyethylene glycols, wherein n is an integer from 2 to 4.

In general, a compound with low reactivity is preferred for normal labelling procedures whereas compounds with higher reactivity is suitable for in vivo use. Thus, compounds with $R_6$ being CH$_3$ or phenyl are suitable for normal labeling and compounds with $R_6$ being H, are particular useful for in vivo use.

In an alternative embodiment, the invention relates to a tetrazine having the above described formula I, wherein one of $R_1$-$R_5$ is $^{18}$F, at least two of the remaining $R_1$-$R_5$ are H, and the other remaining $R_1$-$R_5$ are the same or different and are selected from H, alkyl, halogen, —CF$_3$, —CN, —O-alkyl, —S-alkyl, —NH-alkyl, —N(alkyl)$_2$, —NH(C═O)-alkyl, —N— alkyl-(C═O)-alkyl, —SO$_2$-alkyl, —SO$_2$—NH$_2$, —SO$_2$—NHalkyl, —SO$_2$—N(alkyl)$_2$-C(═O)—NH$_2$, —C(═O)—NH-alkyl, —C(═O)—N(alkyl)$_2$, —C(═O)—OH, —C(═O)—O-alkyl,

, wherein n is an integer from 1 to 4, and $R_6$ is selected from H, wherein the curly bond indicates the link to the tetrazine moiety.

In the present context, the term alkyl is intended to mean linear or branched C$_1$-C$_6$ alkyl, cyclic C$_1$-C$_6$ alkyl, optionally substituted with —OH, —NH$_2$ or halogen.

In the present context, the term halogen is intended to mean I, Br, Cl, or F.

C$_1$-C$_6$ alkyl includes methyl, ethyl, propyl, isopropyl, butyl, sec. butyl, tert. butyl, pentyl and branched pentyl, hexyl and branched hexyl, and C$_3$-C$_6$ cyclic alkyl includes cyclopropyl, cyclobutyl, cyclopentyl, cyclohexyl.

Polyethylene glycol includes ethylene glycol (n=1) and polyethylene glycols, wherein n is an integer from 2 to 4.

Tetrazines of interest are tetrazines where:

$R_1$ is $^{18}F$ and all other R's are H; or $R_2$ is $^{18}F$ and all other R's are H; or $R_3$ is $^{18}F$ and all other R's are H; or $R_1$ is $^{18}F$ and $R_2$, $R_3$, $R_4$, and $R_5$ are H, and $R_6$ is H or or $R_2$ is $^{18}F$ and $R_1$, $R_3$, $R_4$, and $R_5$ are H, and $R_6$ is H or or $R_3$ is $^{18}F$ and $R_1$, $R_2$, $R_4$, and $R_5$ are H, and $R_6$ is H or The reactivity of the tetrazine compounds may be adjusted by the nature of the substituents $R_1$-$R_5$. Thus, e.g. an electron-donating group will typically result in a decrease in reactivity, whereas an electron withdrawing group typically will result in an increase in reactivity.

The $^{18}F$-tetrazines according to the invention are suitable for use in bioorthogonal chemistry (click chemistry) where they act as small effector molecules (tetrazines) carrying $^{18}F$ as payloads. They react in situ with TCO that—carried by a target vector—already is located at the target of interest.

The $^{18}F$-tetrazine compounds are highly reactive compounds. In many applications of pretargeted strategies, the target vector such as an antibody may only very slowly accumulate at their site of action. It may take hours or days. In contrast, small molecules often reach their target within seconds or minutes. As mentioned above, TCO and tetrazine are the two parts reacting with each other at the site of action. It is therefore possible either to use a target vector with TCO or a target vector with Tz and then an effector molecule being either TZ (for the target vector with TCO) or TCO (for the target vector with Tz). However, Tz compounds (corresponding to the Tz compounds of the present invention, but without the label $^{18}F$) are very reactive, which means that using a target vector with Tz most likely will result in degradation of the compound before it reaches the site of action or during its localization at the site of action, which—in both cases—result in no or only minor click reaction after administration of the effector molecule.

Various $^{18}F$-Tz compounds of the invention are small compounds capable of penetrating the blood-brain barrier. This means that these compounds can be used also for CNS targets. In addition, the $^{18}F$ is a short-lived isotope, which is advantageous to use as the radiation exposure is reduced to a minimum compared to standardly used long-lived radionuclides to image nanomedicines such as $^{89}Zr$. Displayed Tz frameworks are chosen because they display high rate constants that are most likely necessary to perform pretargeted strategies in humans. $^{18}F$-substitution in m-position are of special interest because they increase unexpectedly the rate constants compared to the p-substituted version (see Scheme 3). Thus, compounds of the general Formula I wherein $R_2$ or $R_4$ is $^{18}F$ are preferred embodiments of the invention. Variations at the aryl moiety can be used to fine tune the physicochemical properties of the probe in respect to lipophilicity, metabolic stability, etc. for various applications, such as pre-targeted imaging beyond membranes or solubility.

Particularly preferred tetrazine compounds are compounds with $^{18}F$-substitution in m position and a substituent in the other m position. Such tetrazine compounds are compounds of the general formula II:

formula II

Where $R_7$ is selected from —$CH_2$—$NH_2$, —$CH_2$—NH-Alkyl, —C(=O)—$NH_2$, —C(=O)NH-Alkyl, —NH—CH(=O), —NH—C(=O)-Alkyl, —OH, —O-Alkyl, —$CH_2$—O-Alkyl, —$CH_2$—O-phenyl, —$CH_2$—O-Alkyl, —$CH_2$—O-naphthalene, —$CH_2$—C(=O)$NH_2$, —$CH_2$—C(=O)—NH-alkyl In the present context, the term alkyl is intended to mean linear or branched $C_1$-$C_6$ alkyl, cyclic $C_1$-$C_6$ alkyl, optionally substituted with —OH, —$NH_2$ or halogen.

Preferred compounds of formula II are shown in FIG. 8 and listed in table 1 with characteristics below:

TABLE 1

| Compound | LogP (partition coefficient) | LogD (distribution coefficient) |
|---|---|---|
| A | −0.14 | −1.64 |
| B | 0.25 | −1.41 |
| C | 0.27 | −1.14 |
| D | 0.33 | −0.79 |
| E | −0.49 | −0.49 |
| F | −0.26 | −0.26 |
| G | 0.09 | 0.09 |
| H | 0.58 | 0.58 |
| I | 0.00 | 0.00 |
| J | 0.06 | 0.06 |
| K | 0.71 | 0.71 |
| L | 1.13 | 1.13 |
| M | 0.45 | 0.31 |
| N | 0.53 | 0.53 |
| O | 0.88 | 0.88 |
| P | 1.37 | 1.37 |
| Q | 0.54 | 0.54 |
| R | 1.45 | 1.45 |
| S | 2.26 | 2.26 |
| T | 3.26 | 3.26 |
| U | −0.42 | −0.42 |
| V | −0.18 | −0.18 |
| W | 0.17 | 0.17 |

TABLE 1-continued

| Compound | LogP (partition coefficient) | LogD (distribution coefficient) |
| --- | --- | --- |
| X | 0.66 | 0.66 |
| Y | 1.08 | 1.08 |

The advantage of the tetrazines mentioned in table 1 above are their increased reaction kinetics compared to tetrazines that are not labelled at the meta-position of the phenyl ring. Faster conjugation is as such possible with these synthons.

The present invention also includes suitable precursors to the $^{18}$F-radiolabelled tracers detailed above. Suitable compounds are tin-species or boronic acid/esters with following formula III:

Formula III wherein one of $R_1$-$R_5$ is $SnR_3$, $B(OR)_2$, $B(OH)_2$ or similar tin or boronic acid/ester species. R is a alkyl as defined herein that may contain one or more heteroatoms selected from oxygen and nitrogen; and at least two of the remaining $R_1$-$R_5$ are H, and the other remaining $R_1$-$R_5$ are the same or different and are selected from H, alkyl, halogen, —CF$_3$, —CN, —O-alkyl, —S-alkyl, —NH-alkyl, —N(alkyl)$_2$, —NH(C=O)-alkyl, —N-alkyl-(C=O)-alkyl, —SO$_2$-alkyl, —SO$_2$—NH$_2$, —SO$_2$—NHalkyl, —SO$_2$—N(alkyl)$_2$-C(=O)—NH$_2$, —C(=O)—NH-alkyl, —C(=O)—N(alkyl)$_2$, —C(=O)—OH, —C(=O)—O-alkyl, —CH$_2$—NH$_2$, —CH$_2$—NH-alkyl, —OH, CH$_2$—O-alkyl, CH$_2$—O-aryl, CH$_2$—O-phenyl, CH$_2$—O-naphthyl wherein n is an integer from 1 to 4, and $R_6$ is selected from H, CH$_3$, phenyl, wherein the curly bond indicates the link to the tetrazine moiety.

In the present context, the term alkyl is intended to mean linear or branched C$_1$-C$_6$ alkyl, cyclic C$_1$-C$_6$ alkyl, optionally substituted with —OH, —NH$_2$ or halogen.

In the present context, the term halogen is intended to mean I, Br, Cl, or F.

C$_1$-C$_6$ alkyl includes methyl, ethyl, propyl, isopropyl, butyl, sec. butyl, tert. butyl, pentyl and branched pentyl, hexyl and branched hexyl, and C$_3$-C$_6$ cyclic alkyl includes cyclopropyl, cyclobutyl, cyclopentyl, cyclohexyl.

Polyethylene glycol includes ethylene glycol (n=1) and polyethylene glycols, wherein n is an integer from 2 to 4.

In an alternative embodiment, the present invention also includes suitable precursors of formula III, wherein one of $R_1$-$R_5$ is $SnR_3$, $B(OR)_2$, $B(OH)_2$ or similar tin or boronic acid/ester species. R is an alkyl as defined herein that may contain one or more heteroatoms selected from oxygen and nitrogen; and at least two of the remaining $R_1$-$R_5$ are H, and the other $R_1$-$R_5$ are the same or different and are selected from H, alkyl, halogen, —CF$_3$, —CN, —O-alkyl, —S-alkyl, —NH-alkyl, —N(alkyl)$_2$, —NH(C=O)-alkyl, —N-alkyl(C=O)-alkyl, —SO$_2$-alkyl, —SO$_2$—NH$_2$, —SO$_2$—NHalkyl, —SO$_2$—N(alkyl)$_2$-C(=O)—NH$_2$, —C(=O)NH-alkyl, —C(=O)—N(alkyl)$_2$, —C(=O)—OH, —C(=O)—Oalkyl, wherein n is an integer from 1 to 4, and $R_6$ is selected from H, wherein the curly bond indicates the link to the tetrazine moiety.

Further, the invention relates to an iodine precursor to the above-mentioned tin-species or boronic acid/esters precursors.

A tetrazine compound having the following formula IV:

Formula IV wherein one of $R_1$-$R_5$ is iodine (1), at least two of the remaining $R_1$-$R_5$ are H, and the other remaining $R_1$-$R_5$ are the same or different and are selected from H, alkyl, halogen, —CF$_3$, —CN, —O-alkyl, —S-alkyl, —NH-alkyl, —N(alkyl)$_2$, —NH(C=O)-alkyl, —N-alkyl(C=O)-alkyl, —SO$_2$-alkyl, —SO$_2$—NH$_2$, —SO$_2$—NHalkyl, —SO$_2$—N(alkyl)$_2$-C(=O)—NH$_2$, —C(=O)NH-alkyl, —C(=O)—N(alkyl)$_2$,

9

—C(=O)—OH, —C(=O)—O-alkyl, —CH₂—NH₂,

—C(=O)—OH,　　—C(=O)—O-alkyl,　　—CH$_2$—NH$_2$, —CH$_2$—NH-alkyl, —OH, CH$_2$—O-alkyl, CH$_2$—O-aryl, CH$_2$—O-phenyl, CH$_2$—O-naphthyl

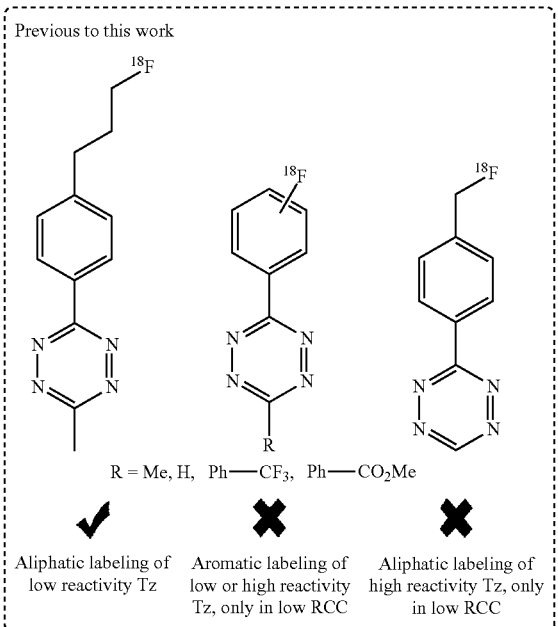

wherein n is an integer from 1 to 4, and

R$_6$ is selected from H, CH$_3$, phenyl, wherein the curly bond indicates the link to the tetrazine moiety.

In the present context, the term alkyl is intended to mean linear or branched C$_1$-C$_6$ alkyl, cyclic C$_1$-C$_6$ alkyl, optionally substituted with —OH, —NH$_2$ or halogen.

In the present context, the term halogen is intended to mean I, Br, Cl, or F.

C$_1$-C$_6$ alkyl includes methyl, ethyl, propyl, isopropyl, butyl, sec. butyl, tert. butyl, pentyl and branched pentyl, hexyl and branched hexyl and C$_3$-C$_6$ cyclic alkyl includes cyclopropyl, cyclobutyl, cyclopentyl, cyclohexyl.

Polyethylene glycol includes ethylene glycol (n=1) and polyethylene glycols, wherein n is an integer from 2 to 4.

Preferred iodine precursors according to the invention are a tetrazine compound of formula IV, wherein one of R$_1$-R$_5$ is iodine (1), at least two of the remaining R$_1$-R$_5$ are H, and the other remaining R$_1$-R$_5$ are the same or different and are selected from H, alkyl, halogen, —CF$_3$, —CN, —O-alkyl, —S-alkyl, —NH-alkyl, —N(alkyl)$_2$, —NH(C=O)-alkyl, —N-alkyl-(C=O)-alkyl, —SO$_2$-alkyl, —SO$_2$—NH$_2$, —SO$_2$—NHalkyl, —SO$_2$—N(alkyl)$_2$-C(=O)—NH$_2$, —C(=O)—NH-alkyl, —C(=O)—N(alkyl)$_2$, —C(=O)—OH, —C(=O)—O-alkyl, wherein n is an integer from 1 to 4, and R$_6$ is selected from H, wherein the curly bond indicates the link to the tetrazine moiety.

In the present context, the term alkyl is intended to mean linear or branched C$_1$-C$_6$ alkyl, cyclic C$_1$-C$_6$ alkyl, optionally substituted with —OH, —NH$_2$ or halogen.

In the present context, the term halogen is intended to mean I, Br, Cl, or F.

C$_1$-C$_6$ alkyl includes methyl, ethyl, propyl, isopropyl, butyl, sec. butyl, tert. butyl, pentyl and branched pentyl, hexyl and branched hexyl, and C$_3$-C$_6$ cyclic alkyl includes cyclopropyl, cyclobutyl, cyclopentyl, cyclohexyl.

Polyethylene glycol includes ethylene glycol (n=1) and polyethylene glycols, wherein n is an integer from 2 to 4.

In a particularly preferred embodiment, the iodine precursors have iodine in the meta position, i.e. R$_2$ or R$_4$ is I (iodine).

The inventors of the present invention have tested several synthetic routes in order to prepare the compounds of the present invention. Standard procedures in this respect have been applied.

With reference to the following scheme 1, until now it has only been possible to obtain [18]F Tz compounds where the fluorine moiety is directly linked to the phenyl group with very low radiochemical conversion (RCC), which result in clinical irrelevant amounts. Moreover, the [18]F Tz compound, where the fluorine is linked via an alkyl group, has no clinical relevance. This is because of the associated low rate constants which will not be suitable for pretargeted strategies in humans.

Scheme 1

-continued

This work

R₁-₅ see above, one is ¹⁸F

R₆ = H,

Aromatic labeling of
high reactivity
Tz in high RCC

Conventional ¹⁸F-labeling conditions result in decomposition of highly activated Tz's. Recently, several alternative strategies have been published that minimize basicity during the labeling procedure, proceed via a different mechanistic pathway or apply better leaving groups. Especially, Cu-mediated oxidative fluorination of tin- and boronic ester/acid species, concerted nucleophilic aromatic substitution of uronium salts, hypervalent iodonium based precursors and minimalistic labeling strategies have shown potential for this purpose. Structures that have been thought to be impossible to label can now be ¹⁸F-fluorinated using these new strategies.

The inventors of the present invention decided to study if one of these approaches could be used to radiolabel highly activated Tzs. As a model compound, an initial focus was on relatively low reactive methyl-phenyl Tz (roughly 100 times lower than H— or bispyridyl based Tz). The purpose was to investigate whether the respective precursors are synthetic accessible and if specific radiolabeling conditions can be applied to the Tzs in question.

Synthesis of the reference compound (6) proceeded in low but satisfying yield and was carried out in a Pinner-like, 2-step synthesis procedure starting from 4-fluoro-benzonitrile, hydrazine and MeCN and subsequently followed by an oxidation using NaNO₂. Precursor for the conventional labeling approach (1) and for the concerted substitution (3) were synthesized in accordance, whereas the spirocyclic iodonium ylide (4), iodonium salt (3) and tin species precursor (5) were synthesized with the aid of a Pd-mediated pathway starting from (1).

In a next step, efforts were directed towards ¹⁸F-radiolabeling. Aliquot labeling experiments were carried out to increase through-put and investigate the feasibility of each pathway most efficiently. Initially, labeling conditions were chosen based on a literature research using selection criteria such as maximum RCC, low basicity reaction conditions and short reaction time. RCC was determined using thin-layer chromatography (TLC) and the identity of the ¹⁸F-labeled product was determined via high-performance liquid chromatography (HPLC). The following Scheme 2 summarizes the investigated strategies, the X meaning no product was detected.

Scheme 2

Conventional ¹⁸F-labeling

Nucleophile labeling via Iodonium ylides

SₙAr

SₙAr

1

4

-continued

Nucleophile labeling via Iodonium salt

2

CS$_N$Ar ✗→

[$^{18}$F]6

Cu-mediated $^{18}$F-fluorination via tin species oxidative
fluorination ✓

5

Nucleophile labeling via uronium salt

3

CS$_N$Ar ✗→

Radiolabeled product ([$^{18}$F]6) could only be detected starting from the tin-precursor (5). Radiolabeling using one of the other approaches including minimalist approaches failed. Only decomposition adducts could be detected. In contrast, the Cu-mediated $^{18}$F-fluorination of (5) resulted in [$^{18}$F]6 in a radiochemical conversion (RCC) of 38% after reaction optimization. The table below summarized these efforts. Interestingly, high temperatures had a deleterious effect on the reaction. Short reaction time (5 min) already yielded in the highest possible RCC. Table 2 summarizes the obtained results.

TABLE 2

Optimization attempts to synthesize [$^{18}$F]6:
a) General labeling conditions;
b) Effect of the reaction time on the RCC;
c) Temperature effect on the RCC, and
d) Base amount influence on the RCC:

a)
Cu(OTf)$_2$, pyridine, [$^{18}$F]KF
DNA, time, temperature →

(5)                                             [$^{18}$F]6

TABLE 2-continued

Optimization attempts to synthesize [$^{18}$F]6:
a) General labeling conditions;
b) Effect of the reaction time on the RCC;
c) Temperature effect on the RCC, and
d) Base amount influence on the RCC:

b)

| Entry | Reaction time [min] | RCC[b] [%] |
|---|---|---|
| 3 | 5 | 38 |
| 5 | 15 | 36 |

[a]Conditions: Cu(OTf)$_2$, pyridine, [$^{18}$F]KF, DMA 100° C.;
[b]determined by TLC c)

| Entry | Temperature [° C.] | RCC[b] [%] |
|---|---|---|
| 3 | 100 | 38 |
| 5 | 130 | — |

[a]Conditions: Cu(OTf)$_2$, pyridine, [$^{18}$F]KF, DMA, 5 min;
[b]determined by TLC d)

| Entry | Base amount [μg] | RCC[b] [%] |
|---|---|---|
| 2 | 50 | 25 |
| 4 | 200 | 38 |

[a]Conditions: Cu(OTf)$_2$, pyridine, [$^{18}$F]KF, DMA 100° C., 5 min;
[b]determined by TLC Based on these encouraging results, a study was performed to investigate whether the identified labeling conditions could be applied to Tzs that are more reactive. In this respect, Tz's with stepwise increased reactivity have been tested. This set up also made it possible to investigate the product characteristics of the suggested labeling procedure (Scheme 3). Synthesis of respective reference compounds and precursors was completed in the same manner as discussed before. Respective second-order rate constants were determined via stopped-flow measurements. Interestingly, meta-substitution increased the rate constants by a factor of approximately 2. Radiolabeling was studied using the best aliquot conditions identified in our previous experiments. RCC for [$^{18}$F]7, [$_{18}$F]8 and [$^{18}$F]9 were 35%, 30%, and 33%, respectively.

---

Scheme 3

| | [$^{18}$F]6 | [$^{18}$F]7 | [$^{18}$F]8 | [$^{18}$F]9 |
|---|---|---|---|---|
| Radiochemical incorporation [%] | 38 | 35 | 30 | 33 |
| Radiochemical yield [%] | 5 | 4.7 | 2 | 2.3 |
| Second-order rate constant $k_2$ [$M^{-1}s^{-1}$] at 25° C. | 2.25 | not determined | 159 | 222 |

---

In order to enable up-scaling of the method, the inventors investigated whether a one-pot method could be used. For Cu-mediated $^{18}$F-fluorinations, up-scaling from aliquot conditions is not always easily achievable because of the base sensitivity of the reaction. In addition, for some radioactivity losses are not accounted for in aliquot labeling. For example, the loss due to [$^{18}$F]-fluoride vessel wall absorption is not accounted for. Compounds [$^{18}$F]6, [$^{18}$F]7, [$^{18}$F]8, and [$^{18}$F]9 were selected to investigate this issue. In this manner low and high reactivity compounds could be studied. A non-decay corrected (n.d.c) radiochemical yield (RCY) of 4-5% could be isolated at the end of synthesis (EOS) for the lower reactive Tz's, [$^{18}$F]6 and [$^{18}$F]7. The synthesis including [$^{18}$F]fluoride collection, azeotropic drying, labeling, HPLC separation and formulation could be carried out in approximately one hour (Scheme 3). The more volatile compounds [$^{18}$F]8 and [$^{18}$F]8 could only be isolated with appropriate cooling before work-up. A n.d.c. RCY of approximated 2% (Scheme 3). In a follow up experiment compound 8 gave a yield of 5.1% and compound 9 a yield of 5.3%, so both have a yield of approximately 5%

A general method for preparing the compounds of the invention is as follows:

X = C or N
Y = C or N

The general method can also be used for preparing compounds with additional substitutions as shown below:

This general method has been used to prepare the compounds below:

| RCC [%] | 3.62 | nd | 0 | nd | 13.72 |

| RCC [%] | nd | nd | nd | nd |

More details appear from the examples herein.

REFERENCES

1. Fan X, Ge Y, Lin F, Yang Y, Zhang G, Ngai W S C, Lin Z, Zheng S, Wang J, Zhao J. Optimized tetrazine derivatives for rapid bioorthogonal decaging in living cells. Angewandte Chemie International Edition 2016; 55(45): 14046-14050.
2. Yang J, Karver M R, Li W, Sahu S, Devaraj N K. Metal-Catalyzed One-Pot Synthesis of Tetrazines Directly from Aliphatic Nitriles and Hydrazine. Angewandte Chemie 2012; 124(21):5312-5315.
3. Thompson A L, Kabalka G W, Akula M R, Huffman J W. The conversion of phenols to the corresponding aryl halides under mild conditions. Synthesis 2005; 2005(04): 547-550.
4. Murata M, Oyama T, Watanabe S, Masuda Y. Palladium-catalyzed borylation of aryl halides or triflates with dialkoxyborane: A novel and facile synthetic route to arylboronates. The Journal of organic chemistry 2000; 65(1):164-168.
5. McIntee J W, Sundararajan C, Donovan A C, Kovacs M S, Capretta A, Valliant J F. A convenient method for the preparation of fluorous tin derivatives for the fluorous labeling strategy. The Journal of organic chemistry 2008; 73(21):8236-8243.
6. Makaravage K J, Brooks A F, Mossine A V, Sanford M S, Scott P J. Copper-Mediated Radiofluorination of Arylstannanes with [18F] K F. Organic letters 2016; 18(20): 5440-5443.

Experimental

All chemicals were received from commercial sources (SigmaAldrich, VWR International and Alfa Aesar) and used without further purification. TLC analysis was completed using Silica Gel 60 F254 on aluminium with a 1:1 mixture of n-heptane and EtOAc as the mobile phase. Flash chromatography was completed using 40-60 μm silica gel. NMR spectra were recorded with either a 400 MHz Bruker Avance III or a 600 MHz Bruker Avance III HD. Mass spectra analysis was completed using MS-Acquity-A: Waters Acquity UPLC with QDa-detector. Reagents and solvents were obtained from suppliers and used without further purification. Radioactivity high-performance liquid chromatography (radioHPLC), radioactivity thin layer chromatography (radioTLC) were carried out using Thermo Fisher Scientific devices and radiodetectors from ScanSys and Elysia-Raytest.

Rate Constant Measurements

Reaction kinetics were determined by pseudo-first order measurements in PBS (pH=7.4) at 37.0±0.1° C. Measurements were performed using a SX20 stopped flow photometer (Applied Photophysics, UK) equipped with a 360 nm LED light source and a photomultiplier type R374 in combination with a 400 nm longpass filter as detector.

Production of [18F]Fluoride

[18F]fluoride was produced via a (p,n)-reaction on a CTI Siemens cyclotron (Rigshospitalet, Denmark) by irradiating [18O]H_2O with 11 MeV protons. An anion exchange resin (Sep-Pak Light Waters Accell Plus QMA cartridge) was washed with EtOH (20 mL), 9 mg/mL KOTf (aq) (10 mL) and water (20 mL) and dried with air. Then the aqueous [18F]fluoride solution was passed through this exchange resin and the resin eluted with a mixture of KOTf (10 mg) and K_2CO_3 (150 μg) in 550 μL water. The resulting mixture was then gently concentrated to dryness at 90° C. by acetropic drying with 2×ACN (0.6 mL), under a nitrogen stream for 20 min, to give no-carrier-added K[18F]F complex as a white semi-solid residue (dried fluoride).

Radiochemical Conversion (RCC)

Radiochemical conversion (RCC) was determined by radio thin-layer chromatography (TLC) by dividing the integrated area of the spot by the total contained on the plate. Analytical HPLC of all radiolabeled compounds was completed by comparison of the $^{19}$F reference compounds synthesised previously vide supra.

Radiochemical Yield (RCY)

Radiochemical yield (RCY) was determined using the activity of the dried fluoride at the start of the reaction and that of the purified product and it has not been decay corrected.

Labeling of Tetrazines

Aliquot Procedure Starting from Tin Precursor

Dried fluoride was redissolved in in 1 mL DMA. 0.1 mL of this solution was added to the corresponding trimethyl ditin precursor (0.01 mmol), $Cu(OTf)_2$ (7.2 mg, 0.02 mmol) and pyridine (12 μL, 0.15 mmol), which was dissolved in 0.9 mL DMA. This mixture was heated to 100° C. for 5 min. The mixture was cooled to 40° C. before the mixture was transferred to 3 mL of water and analyzed using radioTLC.

One-Pot Procedure Starting from Tin Precursors

Trimethyl ditin precursor (0.01 mmol) was dissolved in 0.8 mL DMA and added 0.1 mL of stock solutions of $Cu(OTf)_2$ (7.2 mg, 0.02 mmol) and pyridine (12 μL, 0.15 mmol). This mixture was added to the dried [$^{18}$F]FK and heated to 100° C. for 5 min[1]. The mixture was cooled to 40° C. before the mixture was transferred to 3 mL of water and afterwards purified via semi-preparative HPLC (LUNA (phenomenex) 250×10 mm, 10 μm, 50:50 ACN:$H_2O$ (0.1% TFA), flowrate 6 mL/min. The fraction containing [$^{18}$F] tetrazine was collected into a vial containing 30 mL water. This was then transferred to a Sep-Pack plus cartridge. The product was eluted with DCM (2 mL) and evaporated to dryness under a stream of helium. Typically, 1% RCY was obtained (not decay corrected) in a synthesis time of 1 h including drying of fluorine-18. The residue was dissolved in 0.05 mL EtOH and 1 ml phosphate buffer.

[1] In the initial optimization samples were withdrawn at 5, 10 and 15 min. However, it was later realized, that the compounds were volatile under the conditions, therefore the obtained results are unreliable and not shown here.

The product was analyzed using a C18 LUNA (phenomenex) column, 5 μm, 250×4.6 mm in 2-mL/min solvent flow. A gradient system with two eluents, A and B, was used, with the fraction of B varying from 0% to 100% over 15 min. A=$H_2O$, 0.1% TFA; B=ACN: $H_2O$, 0.1% TFA:

| Compound | Retention time analytical | Retention time preparative |
|---|---|---|
| [$^{18}$F]6 | 7.7 min | 525 sec |
| [$^{18}$F]7 | 7.8 min | 650 sec |
| [$^{18}$F]8 | 7.4 min | 575 sec |
| [$^{18}$F]9 | 7.5 min | 600 sec |

(see HPLC chromatograms for further information)

Radiolabeling of [$^{18}$F]6 Using Precursor 1, 2, 3 or 4

Only aliquot labeling conditions were applied:

Starting from 1

Dried fluoride was redissolved in 1 mL DMF. 0.1 mL of this solution was added to the corresponding precursor 1, which was dissolved in 0.9 mL DMF. This mixture was heated to 100° C. for 30 min. After 1, 3, 5, 10, 20 and 30 min reaction time, 0.05 mL sample was removed out of the reaction mixtures, diluted with 3 mL of water and analyzed using radioTLC. No product was detected.

Starting from 2

Dried fluoride was redissolved in 1 mL DMF. 0.1 mL of this solution was added to the corresponding precursor 2, which was dissolved in 0.9 mL DMF. This mixture was heated to 100° C. for 30 min. After 1, 3, 5, 10, 20 and 30 min reaction time, 0.05 mL sample was removed out of the reaction mixtures, diluted with 3 mL of water and analyzed using radioTLC. No product was detected.

Starting from 3

The corresponding phenol (8.7 μmol, 1.0 eq.) and [CpRu (cod)Cl] (1) (8.0 mg, 26 μmol, 3.0 eq.) were added to a vial containing EtOH (50 μL). The vial was capped, and the reaction mixture was stirred at 85° C. for 30 min. The vial was removed from the heating and allowed to cool to RT. Imidazolium chloride (12 mg, 26 μmol, 3.0 eq.) and 150 μL of MBCN were added, and the resulting solution was drawn into a 1.0 mL polypropylene syringe (solution 1). Target water from the cyclotron containing $^{18}$F-fluoride was loaded with a syringe onto a Chromafix 30-PS-HCO$_3$. The cartridge was washed with MBCN (1.0 mL). The cartridge was inverted and fitted with a female×female Luer adapter. With the syringe containing solution 1, $^{18}$F-fluoride loaded onto the Chromafix 30-PS-HCO$_3$ was eluted into a 3.7 mL borosilicate vial. The cartridge was washed with DMSO: MeCN (150 μL, 1:1 (v/v)). The reaction mixture was sealed and heated at 125° C. for 30 min. After 1, 3, 5, 10, 20 and 30 min, 0.05 mL sample was removed out of the reaction mixtures, diluted with 3 mL of water and analyzed using radioTLC. No product was detected.

Starting from 4

Dried fluoride was redissolved in 1 mL DMF. 0.1 mL of this solution was added to the corresponding precursor 4, which was dissolved in 0.9 mL DMF. This mixture was heated to 100° C. for 30 min. After 1, 3, 5, 10, 20 and 30 min reaction time, 0.05 mL sample was removed out of the reaction mixtures, diluted with 3 mL of water and analyzed using radioTLC. No product was detected.

TCO Click Ability

To a solution of TCO-KSMO (the polymer) 500 μL (1 mg/mL) PBS was added 100 μL of the formulated tetrazine.

In given time intervals, 2 μL of the solution was withdrawn and quenched with 20 μL of a 3 mg/mL bispyridine-tetrazine solution. TLC (EtOAc) determined the fraction of tetrazines reacted to the TCO. (tetrazine; front, 1,4 adduct; baseline)

All the Tetrazines Reacted Immediately with the KSMO-TCO

| Tetrazine | 15 sec | 30 sec | 1 min | 2 min | 3 min | 5 min |
|---|---|---|---|---|---|---|
| [$^{18}$F]6 | — | 100% | 100% | 100% | 100% | 100% |
| [$^{18}$F]7 | — | 100% | 100% | 100% | 100% | 100% |
| [$^{18}$F]8 | — | — | 100% | 100% | 100% | 100% |
| [$^{18}$F]9 | 100% | 100% | 100% | 100% | 100% | — |

Blood Stability

Blood stability was tested by mixing 250 μL mice whole blood with 250 μL of the formulated Tz, the mixture was heated and shaken at 37° C. At given time points 1, 2, 3, 5, 10, 20, 60 and 180 min, 20 μL were withdrawn and cooled to 0° C. At the same time points, 20 μL were added to a 20 μL of a solution of 1 mg/mL KSMO (TCO-Polymer) in PBS and left at RT for 1 h.

The mixtures were then centrifuged at 4200 rpm for 3 min, before ACN (40 μL) was added and centrifuged again for 3 min at 4200 rpm. The supernatant was withdrawn and analyzed with TLC and/or HPLC.

TLC Data

|  | [18F]7 | | [18F]8 | |
|---|---|---|---|---|
| Time | Stability | TCO click ability | Stability | TCO-Click- ability |
| 0 min | 94% | 100% | 90% | 100% |
| 1 min | 95% | 100% | 72% | 100% |
| 2 min | 96% | 100% | 85% | 100% |
| 3 min | 95% | 100% | 89% | 100% |
| 5 min | 95% | 100% | 88% | 100% |
| 10 min | 96% | 100% | 90% | 100% |
| 20 min | 96% | 100% | 89% | 100% |
| 60 min | 96% | 100% | 88% | 100% |
| 180 min | 77% | 100% | 82% | 100% |

Animal Studies

Figure 3:
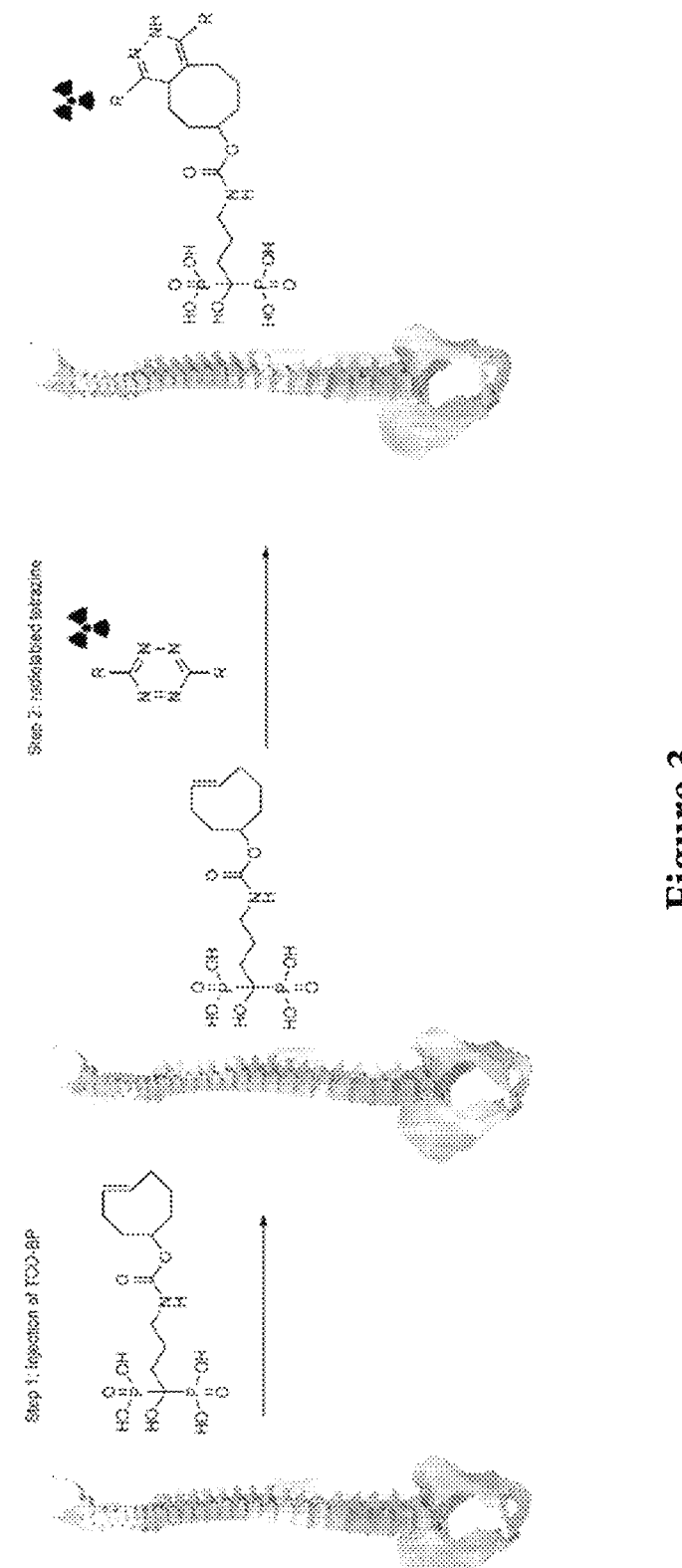
FIG. 3 illustrates the Pretargeting concept using BP-TCO.

FIG. 3 displays the general pretargeted concept that has been used for this study. All animal studied were approved by the Danish Animal Welfare Council, ministry of Justice. Five weeks old female Balb/c mice (Charles River) were acclimatized for one week with access to water and chow ad libitum. Trans-cyclooctene functionalized bisphosphonates (TCO-BP's) (100 µg. 100 µl PBS) were injected i.v. (n=2), and 1 hour later animals were administered i.v. with [18F]9 (ca 4MBq) via the tail vein. Control animal did not receive any TCO-BPs (n=2).

The animals were scanned on a dedicated small animal PET/CT scanner (Siemens) during which they were kept anesthetized by breathing sevoflurane and their temperature maintained by heating pad. Immediately after injection of [18F]9, the animals were moved to a small animal PET/CT scanner and a 60 min dynamic PET acquisition (energy window of 350-650 KeV and a time resolution of 6 ns) was performed followed by a CT scan (360 projections, 65 kV, 500 ρA and 400 ms). Sinograms from PET scans were framed and reconstructed using a 3-dimensional maximum a posteriori algorithm with CT-based attenuation correction. PET and CT images were co-registered and analysed using Inveon software (Siemens). The mean percentage of injected dose per grams (% ID/g) in different tissues was extracted by manually creating regions of interest on fused PET/CT images.

Figure 1:
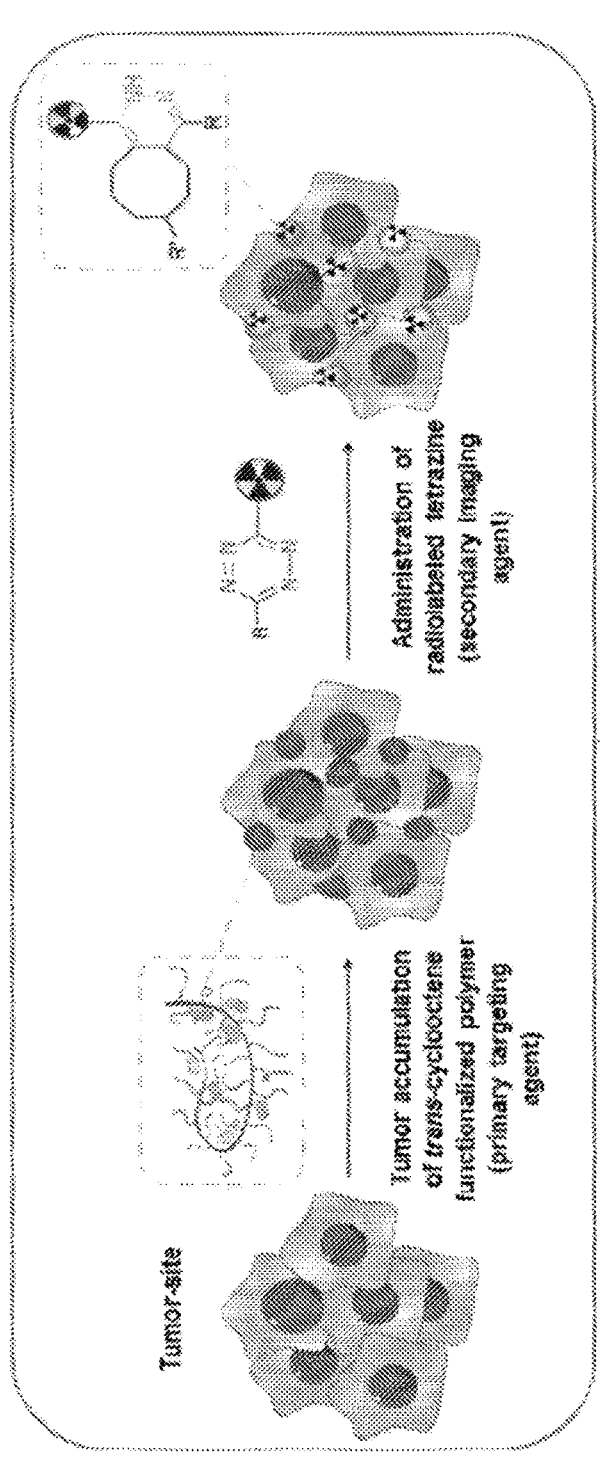
FIG. 1 illustrates the Pretargeting concept.

The bioorthogonal chemistry employed is illustrated in FIG. 1. Please, note that BP illustrates, i.e. bisphosphonate, to which TCO is coupled (TCO-BP). When this target vector has been located to the tissue of interest (in this case the knee, TCO-BPs accumulates at bones), the administration of 18F-Tz results in a click reaction and a labelling of the localised target vector with 18F.

The results are shown in FIG. 2 from which it is seen that the 18F-Tz only clicks to the TCO-BPs bound to bones (in this case the knee). Within blood, no differences within TCO-BP treated and non-treated animals were observed as indicated by the heart signal.

Organic Synthesis

General Procedure A.1. Synthesis of 3-substituted-6-substituted-1,2,4,5-tetrazine The selected aromatic halogenated nitrile (1 mmol, 1 equiv), Zn(OTf)2 (182 mg, 0.5 mmol, 0.5 equiv) and Hydrazine Monohydrate (2.43 mL, 50 mmol, 50 equiv), along with the appropriate second nitrile (5 mmol, 5 equiv), were added to a microwave vial equipped with a stir bar and sealed. The reaction was allowed to stir at 60° C. for 24 hours before being allowed to cool to room temperature and unsealed. NaNO2 (1.35 g, 20 mmol, 20 equiv) in water (6 mL) was added to the now yellow mixture followed by the dropwise addition of HCl (2M) until gas evolution ceased and a pH of 3 was achieved producing a mixture red in colour. The mixture was then extracted with EtOAc, washed with brine, dried with MgSO4, filtered before concentrating in vacuo. The tetrazine was then purified via automatic flash chromatography utilising in various mixtures as the eluent.

3-(3-fluoro)-6-methyl-1,2,4,5-tetrazine (7) (RGV_49): Starting Material 120 mg; The product was purified as a purple solid using flash chromatography (n-Heptane: EtOAc=9:1). Yield: 80 mg (42%); Rf: 0.8; $^1$H NMR (400 Hz, MeOD) δ 8.42 (m, 1H), 8.27 (m, 1H), 7.69 (m, 1H), 7.43 (m, 1H) 2.95 (s, 3H); $^{13}$C NMR (400 Hz, MeOD) δ 167.63, 163.34 (d, J=3.28 Hz), 163.29 (d, J=247.10 Hz), 130.93 (d, J=3.28 Hz), 123.61 (d, J=3.28 Hz), 119.57 (d, J=21.19 Hz), 114.80 (d, J=23.65 Hz), 21.20; UPLCMS [M+H] m/z calc. for $[C_9H_8FN_4]^+$: 191.07; Found: 191.47.

3-(3-hydroxy)-6-methyl-1,2,4,5-tetrazine (12): Starting Material 120 mg; The product was purified as a purple solid using flash chromatography (n-Heptane:EtOAc=8:1). Yield: 86 mg (46%); Rf: 0.52; $^1$H NMR (400 Hz, DMSO) δ 9.97 (s, 1H) 7.94 (m, 2H) 7.50 (t, J=7.83, 15.65 Hz, 1H), 7.11 (d, J=7.66 Hz, 1H), 3.03 (s, 3H); $^{13}$C NMR (400 Hz, DMSO) δ 166.44, 162.69, 137.51, 130.24, 128.21, 99.15, 20.19; UPLCMS [M+H] m/z calc. for $[C_9H_9ON_4]^+$: 188.07

3-(3-iodo)-6-methyl-1,2,4,5-tetrazine (13) (RGV_50): Starting Material 229 mg; The product was purified as a purple solid using flash chromatography (n-Heptane: EtOAc=19:1). Yield: 87.9 mg (29%); Rf: 0.9; $^1$H NMR (400 Hz, CDCl$_3$) δ 8.88 (s, 1H), 8.51 (d, J=9.28 Hz, 1H) 7.88 (d, J=9.28 Hz, 1H), 7.26 (t, J=7.87, 15.78 Hz 1H), 3.05 (s, 3H); $^{13}$C NMR (400 Hz, CDCl$_3$) δ 167.64, 162.95, 141.38, 136.68, 133.72, 130.83, 126.99, 94.79, 21.21; UPLCMS [M+H] m/z calc. for [C$_9$H$_8$IN$_4$]$^+$: 298.97; Found: 299.38.

3-(4-fluorophenyl)-6-phenyl-1,2,4,5-tetrazine (RGV_72): The compound was obtained from 4-Fluorobenzonitrile (121 mg) and Benzonitrile (477 uL). The compound was isolated by preparative TLC using as eluent Toluene/60% n-Heptane, yielded a pink solid. Rf: 0.65 (Toluene:n-Heptane=10:1). $^1$H NMR (600 MHz, Chloroform-d) δ 8.72-8.67 (m, 2H), 8.67-8.62 (m, 2H), 7.69-7.59 (m, 3H), 7.31 (t, J=8.6 Hz, 2H); $^{13}$C NMR (600 MHz, Chloroform-d) δ 166.83, 165.14, 164.11, 163.35, 132.90, 131.86, 130.46 (d, J=9.0 Hz), 129.49, 128.14, 116.75 (d, J=22.0 Hz).

3-(4-iodophenyl)-6-phenyl-1,2,4,5-tetrazine (RGV_14): The compound was obtained from 4-Iodobenzonitrile (229 mg) and Benzonitrile (477 uL) to give 35 mg (10%) of a pink solid. Rf: 0.5 (Toluene:n-Heptane=9:1); $^1$H NMR (400 Hz, CDCl$_3$) δ 8.65 (dd, J=7.3, J=1.5 Hz, 2H), δ 8.38 (d, J=8.5 Hz, 2H), δ 7.98 (d, J=8.5 Hz, 2H), δ 7.67-7.60 (m, 3H); $^{13}$C NMR (600 MHz, CDCl3) δ 164.3, 163.8, 138.8, 133.0, 131.8, 131.5, 129.5, 128.2, 100.5.

3-(3-fluorophenyl)-6-phenyl-1,2,4,5-tetrazine (RGV_71): The compound was obtained from 3-fluorobenzonitrile (107 uL) and Benzonitrile (477 uL). The compound was isolated by preparative TLC using as eluent Toluene/10% n-Heptane, yielded a pink solid. Rf: 0.65 (Toluene:n-Heptane=10:1). $^1$H NMR (400 MHz, Chloroform-d) δ 8.64-8.58 (m, 2H), 8.40 (dt, J=7.8, 1.3 Hz, 1H), 8.33-8.26 (m, 1H), 7.62-7.50 (m, 4H), 7.28 (tdd, J=8.3, 2.7, 1.0 Hz, 1H); $^{13}$C NMR (600 MHz, CDCl3) δ 164.38, 164.32, 163.40 (J=3.09), 162.68, 134.17 (J=8.29), 133.07, 131.76, 131.16 (J=8.01), 129.53, 128.29, 123.84, 119.84 (J=21.35), 114.98 (J=24.4).

3-(3-Iodophenyl)-6-phenyl-1,2,4,5-tetrazine (RGV_15): The compound was obtained from 3-Iodobenzonitrile (229 mg) and Benzonitrile (477 uL) to give 50 mg (14%) of a pink solid. Rf: 0.5 (Toluene:n-Heptane=9:1); $^1$H NMR (400 Hz, CDCl$_3$) δ 9.02 (t, J=1.8 Hz, 1H), δ 8.65 (dd, J=8.0, J=1.6 Hz, 2H), δ 8.62 (d, J=8.0 Hz, 1H), δ 7.97 (d, J=7.9 Hz, 1H), δ 7.66-7.60 (m, 3H), δ 7.35 (t, J=7.4 Hz, 1H); $^{13}$C NMR (600 MHz, CDCl$_3$) δ 164.4, 163.0, 141.6, 136.9, 133.9, 133.1, 131.7, 131.0, 129.52 128.3, 127.2, 95.03.

3-(4-fluorophenyl)-6-(pyridin-2-yl)-1,2,4,5-tetrazine (21) (RGV_3): 2-Cyanopyridine (520 mg, 5 mmol), Zn(OTf)$_2$ (182 mg, 0.5 mmol), Hydrazine Monohydrate (2.43 mL, 50 mmol) and 4-Flourbenzonitril (121 mg, 1 mmol) were added in a microwave vial and sealed. The mixture was allowed to stir at 60° C. for 22 hours, and when the reaction is completed, is cooled at room temperature and unsealed. A solution of $NaNO_2$ (1.35 g, 20 mmol) in water (6 mL) was added to the crude reaction followed by the dropwise addition of HCl (2M) until gas evolution ceased and a pH of 3-2 was achieved producing a red mixture. The crude reaction was extracted with EtOAc and washed once with brine. The organic phase was collected, dried with $MgSO_4$, filtered and concentrated in vacuo. The tetrazine was purified via flash chromatography using n-Heptane:EtOAC (1:1) as eluent, yielded as a pink solid (53.15 mg, 21%). 1H NMR (400 Hz, $CDCl_3$) d 8.97 (d, J=4.32 Hz, 1H), d 8.72 (dd, J=5.41 Hz, J=8.91 Hz, 2H), d 8.69 (d, J=7.93 Hz, 1H), d 8.00 (dd, J=6.93, J=8.63 Hz, 1H), d 7.57 (dd, J=5.2, J=7.79 Hz, 1H), d 7.31 (dd, J=8.67 Hz, 2H).

3-(4-Iodophenyl)-6-(pyridin-2-yl)-1,2,4,5-tetrazine (20): 2-Cyanopyridine (520 mg, 5 mmol), $Zn(OTf)_2$ (182 mg, 0.5 mmol), Hydrazine Monohydrate (2.43 mL, 50 mmol) and 4-Iodobenzonitrile (229 mg, 1 mmol) were added in a microwave vial and sealed. The mixture was allowed to stir at 60° C. for 22 hours, and when the reaction is completed, is cooled at room temperature and unsealed. A solution of $NaNO_2$ (1.35 g, 20 mmol) in water (6 mL) was added to the crude reaction followed by the dropwise addition of HCl (2M) until gas evolution ceased and a pH of 3-2 was achieved producing a red mixture. The crude reaction was extracted with EtOAc and washed once with brine. The organic phase was collected, dried with $MgSO_4$, filtered and concentrated in vacuo. The tetrazine was purified via flash chromatography using Toluene:EtOAC (2:1) as eluent, yielded as a pink solid (57.8 mg, 16%). 1H NMR (400 Hz, $CDCl_3$) d 9.05 (d, J=4.73 Hz, 1H), d 8.77 (d, J=7.93 Hz, 1H), d 8.49 (d, J=8.61 Hz, 2H), d 8.00 (d, J=8.73 Hz, 1H), d 7.65 (dd, J=4.73, J=7.62 Hz, 1H), d 7.33 (dd, J=7.54 Hz, 2H).

3-(4-Iodophenyl)-6-(pyrimidin-2-yl)-1,2,4,5-tetrazine (22): 2-Cyanopyrimidine (525 mg, 5 mmol), $Zn(OTf)_2$ (182 mg, 0.5 mmol), Hydrazine Monohydrate (2.43 mL, 50 mmol) and 4-Iodobenzonitrile (229 mg, 1 mmol) were added in a microwave vial and sealed. The mixture was allowed to stir at 60° C. for 22 hours, and when the reaction is completed, is cooled at room temperature and unsealed. A solution of $NaNO_2$ (1.35 g, 20 mmol) in water (6 mL) was added to the crude reaction followed by the dropwise addition of HCl (2M) until gas evolution ceased and a pH of 3-2 was achieved producing a red mixture. The crude reaction was extracted with EtOAc and washed once with brine. The organic phase was collected, dried with $MgSO_4$, filtered and concentrated in vacuo. The tetrazine was purified via flash chromatography using n-Heptane:EtOAC (1:2) as eluent, yielded as a pink solid (51.8 mg, 14%). 1H NMR (400 Hz, $CDCl_3$) d 9.14 (d, J=4.86 Hz, 2H), d 8.47 (dd, J=6.76 Hz, J=1.78 Hz, 2H), d 8.01 (dd, J=6.76 Hz, J=1.78 Hz, 2H), d 7.60 (t, J=4.85 Hz, 1H).

3-(4-fluorophenyl)-6-(pyrimidin-2-yl)-1,2,4,5-tetrazine (23): 2-Cyanopyrimidine (525 mg, 5 mmol), $Zn(OTf)_2$ (182 mg, 0.5 mmol), Hydrazine Monohydrate (2.43 mL, 50 mmol) and 4-Flourbenzonitril (121 mg, 1 mmol) were added in a microwave vial and sealed. The mixture was allowed to stir at 60° C. for 22 hours, and when the reaction is completed, is cooled at room temperature and unsealed. A solution of $NaNO_2$ (1.35 g, 20 mmol) in water (6 mL) was added to the crude reaction followed by the dropwise addition of HCl (2M) until gas evolution ceased and a pH of 3-2 was achieved producing a red mixture. The crude reaction was extracted with EtOAc and washed once with brine. The organic phase was collected, dried with MgSO$_4$, filtered and concentrated in vacuo. The tetrazine was purified via flash chromatography using n-Heptane:EtOAC (1:1) as eluent, yielded as a pink solid (58.4 mg, 23%). 1H NMR (400 Hz, CDCl$_3$) d 9.14 (d, J=4.87 Hz, 2H), d 8.79 (dd, J=5.41 Hz, J=8.96 Hz, 2H), d 7.59 (t, J=4.87 Hz, 1H), d 7.33 (t, J=8.66 Hz, 2H).

General Procedure A.2 for Synthesis of 3-methyl-6-aryl 1,2,4,5-tetrazine.[1,2]

ACN (0.52 mL, 5 mmol), Zn(OTf)$_2$ (182 mg, 0.5 mmol), Hydrazine Monohydrate (2.52 mL, 50 mmol) along with the appropriate second nitrile (1 mmol) were added to a micro-wave vial equipped with a stir bar and sealed. The reaction was allowed to stir at 60° C. for 24 hours before being allowed to cool to room temperature and unsealed. NaNO$_2$ (1.35 g, 20 mmol) in water (6 mL) was added to the now yellow mixture followed by the dropwise addition of HCl (2M) until gas evolution ceased and a pH of 3 was achieved producing a mixture red in colour. The mixture was then extracted with EtOAc, washed with brine, dried with MgSO$_4$, filtered before concentrating in vacuo. The tetrazine was then purified via flash chromatography utilising n-heptane and EtOAc in various mixtures as the eluent.

3-(4-fluorophenyl)-6-methyl-1,2,4,5-tetrazine (6) (RGV_48): Starting Material 120 mg; The product was purified as a purple solid using flash chromatography (n-Heptane:EtOAc=8:1) Yield: 57 mg (29%); Rf: 0.75; $^1$H NMR (400 Hz, CDCl$_3$) δ 8.55 (d, J=9.28 Hz, 2H), 7.20 (d, J=9.14 Hz, 2H), 3.03 (s, 3H); $^{13}$C NMR (400 Hz, CDCl$_3$) δ 167.22, 165.73 (d, J=254.13 Hz) 163.32, 130.23 (d, J=8.92 Hz), 127.99, 116.48 (d, J=21.87 Hz), 21.13; UPLCMS [M+H]$^+$ calc. for [C$_9$H$_8$FN$_4$]$^+$: 191.07; Found: 191.20.

3-(4-hydroxy)-6-methyl-1,2,4,5-tetrazine (10): Starting Material 120 mg; The product was purified as a purple solid using flash chromatography (n-Heptane:EtOAc=8:1) Yield: 32 mg (20%); Rf: 0.75; $^1$H NMR (400 Hz, MeOD) δ 8.48 (d, J=9.28 Hz, 2H), 7.02 (d, J=9.14 Hz, 2H), 3.85 (s, 3H), 2.99 (s, 3H); $^{13}$C NMR (400 Hz, MeOD) δ 166.42, 163.77, 161.71, 129.32, 122.92, 115.72, 19.47; UPLCMS [M+H] m/z calc. for [C$_9$H$_9$ON$_4$]$^+$: 188.07; Found: 189.40.

3-(4-methoxy)-6-methyl-1,2,4,5-tetrazine (11): Starting Material 133 mg; The product was purified as a purple solid using flash chromatography (n-Heptane:EtOAc=8:1) Yield: 82 mg (41%); Rf: 0.69; $^1$H NMR (600 Hz, CDCl$_3$) δ 8.45 (d, J=8.79 Hz, 2H), 6.99 (d, J=8.85 Hz, 2H), 3.83 (s, 3H), 2.97 (s, 3H); $^{13}$C NMR (600 MHz, CDCl$_3$) δ 166.57, 163.74, 163.26, 129.69, 124.18, 114.66, 55.48, 21.04; UPLCMS [M+H] m/z calc. for [C$_{10}$H$_{11}$ON$_4$]$^+$: 202.09

3-(4-Iodo)-6-methyl-1,2,4,5-tetrazine (1) (RGV_5): Starting Material 229 mg; The product was purified as a purple solid using flash chromatography (n-Heptane: EtOAc=19:1). Yield: 85 mg (39%); Rf 0.9; $^1$H NMR (400 Hz, CDCl$_3$) δ 8.31 (d, J=8.72 Hz, 2H), 7.94 (d, J=8.59 Hz, 2H), 3.09 (s, 3H); $^{13}$C NMR (400 Hz, CDCl$_3$) δ 167.49, 163.77, 138.56, 131.29, 129.27, 100.18, 21.21; UPLCMS [M+H] m/z calc. for [C$_9$H$_8$IN$_4$]$^+$: 298.97; Found: 299.45.

Mesityl(4-(6-methyl-1,2,4,5-tetrazin-3-yl)phenyl)iodonium trifluoromethanesulfonate (2): In a sealed tube m-Chloroperbenzoic acid (6.4 mg, 0.037 mmol) and 3-(4-iodophenyl)-6-methyl-1,2,4,5-tetrazine (10 mg, 0.034 mmol) were dissolved in CH$_2$Cl$_2$ (1 mL/0.23 mmol) and stirred at r.t. during 2 hours. Me (5.2 μL, 0.037 mmol) is added and the mixture is cooled to 0° C. followed by dropwise addition of TfOH (9 μL, 0.102 mmol). The reaction mixture was stirred at r.t during 10 minutes. The crude reaction was concentrated under vacuum. Diethyl ether was added and the mixture was stirred at r.t. during 20 minutes and then stored in the freezer during 1 hour for ensure complete precipitation, before filtered and washed with diethyl ether. The resulting solid was collected with methanol and dried under vacuum. 1H NMR (600 Hz, CD$_3$OD$_3$) δ 8.64 (d, J=8.67 Hz, 2H), δ 8.14 (d, J=8.67 Hz, 2H), δ 7.28 (s, 2H), δ 3.06 (s, 3H), δ 2.70 (s, 6H), δ 2.38 (s, 3H).

8-((4-(6-methyl-1,2,4,5-tetrazin-3-yl)phenyl)-3-iodaney-lidene)-6,10-dioxaspiro[4.5]decane-7,9-dione (4): 3-(4-io-dophenyl)-6-methyl-1,2,4,5-tetrazine (15 mg, 0.09 mmol) is dissolved CH$_2$Cl$_2$ (1 mL/1 mmol) in a microwave vial before adding mCPBA (15 mg, 0.09 mmol), the mixture is sealed and allowed to stir at room temperature 3 hours. A solution of 6,10-dioxaspiro[4.5]decane-7,9-dione (25 mg, 0.09 mmol) in Na$_2$CO$_3$ 10% (2.86 mL/mmol) is prepared and then added dropwise to the mixture in the microwave vial. The mixture was stirred at room temperature during 2 hours more. To the crude reaction 5 mL of water is added and is extracted by CH$_2$Cl$_2$, dried with MgSO$_4$, filtered and concentrated in vacuo. The tetrazine was purified via flash chromatography using n-Heptane:EtOAc (1:2) and 15% EtOH as eluent, yielded as a pink solid (5.4 mg, 15%). 1H NMR (400 Hz, CDCl$_3$) d 8.31 (d, J=8.79 Hz, 2H), d 7.94 (d, J=8.59 Hz, 2H), d 3.09 (s, 3H), d 2.19 (m, 2H), d 1.81 (m, 2H).

3-(5-fluoropyridin-2-yl)-6-(pyridin-2-yl)-1,2,4,5-tetra-zine (RGV_61): The compound was obtained from 5-fluo-ropicolinonitrile (122 mg) and 2-Cyanopyridine (520 uL) to give 45 mg (18%) of a pink solid. Rf: 0.5 (n-Heptane:EtOAC=1:1).

General Procedure B. Synthesis of 3-substituted-6-substi-tuted-1,2-dihydro-1,2,4,5-tetrazine The selected aromatic halogenated nitrile (1 mmol, 1 equiv), sulfur (513 mg, 2 mmol, 2 equiv), Hydrazine Mono-hydrate (804 uL, 16.5 mmol, 16.5 equiv) and ethanol (2.0 mL), along with the appropriate second nitrile (4.5 mmol, 4.5 equiv), were added to a microwave vial equipped with a stir bar and sealed. The reaction mixture was heated to 125° C. for 2 hours before being allowed to cool to room temperature, unsealed and dry under vacuum. The mixture was suspended in 10 mL water for extracted with CH$_2$C$_2$ (2×10 mL), washed with brine, dried with MgSO$_4$, filtered before concentrating in vacuo. The tetrazine was then puri-fied via automatic flash chromatography utilising in various mixtures as the eluent.

3(4-Iodophenyl)-6-(pyridin-2-yl)-1,2-dihydro-1,2,4,5-tet-razine (RGV_16): The compound was obtained from 4-Io-dobenzonitrile (229 mg) and 2-Cyanopyridine (433 uL), to give 71 mg (19%) of an orange solid. Rf=0.38 (Toluene/10% EtOAc); $^1$H NMR (400 MHz, DMSO-d$_6$) δ 9.31 (s, 1H), 8.74 (s, 1H), 8.63 (d, J=4.9 Hz, 1H), 8.00-7.86 (m, 2H), 7.85-7.75 (m, 2H), 7.61 (d, J=8.4 Hz, 2H), 7.53 (ddd, J=6.9, 4.8, 1.6 Hz, 1H); $^{13}$C NMR (600 MHz, CDCl$_3$) δ 148.43, 147.14, 138.15, 137.15, 129.79, 127.59, 125.29, 121.53, 97.03.UPLC-MS [M+H] m/z calc. for [C13H10IN5]+: 364.1

3-(5-Iodopyridin-2-yl)-6-(pyridin-2-yl)-1,2-dihydro-1,2, 4,5-tetrazine: The compound was obtained from 2-Cyano- 5-iodopyridine (231 mg) and 2-Cyanopyridine (433 uL), to give 53 mg (15%) of an orange solid. Rf: 0.44 (EtOAc: heptane=1:2); $^1$H NMR (400 MHz, CDCl$_3$): δ 8.79 (d, J=2.1, 1H), 8.64 (br s, 1H), 8.56-8.59 (m, 1H), 8.40 (br s, 1H), 8.04-8.09 (m, 2H), 7.84 (dd, J=8.6 and J=0.8, 1H), 7.78 (dt, J=7.8 and J=1.7, 1H), 7.35-7.40 (m, 1H).

General Procedure C.1. Synthesis of 3-substituted-6-H-1,2,4,5-tetrazine

CH$_2$Cl$_2$ (0.256 mL, 4.00 mmol, 1 equiv), Sulfur (0.257 g, 1 mmol, 0.25 equiv), Hydrazine monohydrate (1.6 mL, 32.00 mmol, 8 equiv) and ethanol (4.0 mL) along with the appropriate nitrile (2 mmol, 1 equiv) were added to a microwave vial equipped with a stir bar. The vessel was sealed and the reaction mixture was heated to 50° C. for 24 hours, before being allowed to cool to room temperature and unsealed. Then 3 ml of CH$_2$Cl$_2$ and NaNO$_2$ (2.8 g, 40.00 mmol, 10 equiv) in water (40 ml) to the now yellow mixture followed by the dropwise of acetic acid (14 mL), producing a mixture red in colour. The reaction mixture was extracted with CH$_2$Cl$_2$, washed with brine, dried with MgSO$_4$ and filtered before concentrating in vacuo. The tetrazine was then purified via flash chromatography utilising n-Heptane and EtOAc in various mixtures as the eluent and recrystallized in n-Heptane.

3-(4-fluorophenyl)-1,2,4,5-tetrazine (RGV_55): The compound was obtained from 4-fluorobenzonitrile (484 mg). The crude was purified using flash chromatography (90/10 Heptane/EtOAc) to yield 0.24 g (34%) of RGV_55 as red crystals. R$_f$=0.33 (EtOAc-heptane, 1:8); $^1$H NMR (400 MHz, CDCl$_3$): δ 10.22 (s, 1H), 8.64-8.70 (m, 2H), 7.27-7.34 (m, 2H); $^{13}$C NMR (101 MHz, CDCl$_3$): δ 166.1 (J=255.0), 165.7, 157.7, 130.7 (2C, J=9.2), 127.8 (2C, J=22.1). UPLCMS [M+H] m/z calc. for [C$_8$H$_6$FN$_4$]$^+$: 177.05; Found: 177.34.

3-(4-Iodophenyl)-1,2,4,5-tetrazine (RGV_56): The compound was obtained from 4-Iodobenzonitrile (916 mg). The product was purified as a purple solid using flash chromatography (90/10 Heptane/EtOAc) to yield 0.31 mg (27%) of RGV_56 as pink crystals. R$_f$=0.37 (EtOAc-heptane, 1:8); $^1$H NMR (600 MHz, CDCl$_3$): δ 10.24 (s, 1H), 8.32-8.35 (m, 2H), 7.95-7.98 (m, 2H); $^{13}$C NMR (151 MHz, CDCl$_3$): δ 166.3, 158.1, 138.8 (2C), 131.2, 129.7 (2C), 101.2. UPLCMS [M+H] m/z calc. for [C$_8$H$_6$IN$_4$]$^+$: 284.96; Found: 299.45.

3-(3-fluorophenyl)-1,2,4,5-tetrazine (RGV_52): The compound was obtained from 3-fluorobenzonitrile (428 uL). The product was purified using flash chromatography (90/10 Heptane/EtOAc) to yield 0.24 mg (34%) as red crystals. R$_f$=0.34 (EtOAc:heptane, 1=8); 1H NMR (400 MHz, CDCl$_3$): δ 10.26 (s, 1H), 8.43-8.47 (m, 1H), 8.32-8.36 (m, 1H), 7.57-7.63 (m, 1H), 7.33-7.39 (m, 1H); $^{13}$C NMR (101 MHz, CDCl$_3$): δ 165.9 (J=3.2), 163.5 (J=247.6), 158.2, 133.9 (J=8.2), 131.2 (J=8.0), 124.2 (J=3.1), 120.4 (J=21.4), 115.3 (J=24.1); UPLCMS [M+H] m/z calc. for [C$_8$H$_6$FN$_4$]$^+$: 177.05; Found: 177.54.

3-(3-Iodophenyl)-1,2,4,5-tetrazine (RGV_53): The compound was obtained from 3-Iodobenzonitrile (916 mg). The product was purified as a purple solid using flash chromatography (90/10 Heptane/EtOAc) to yield 0.36 mg (32%) of RGV_53 as pink crystals. R$_f$=0.36 (EtOAc; heptane, 1=8); $^1$H NMR (600 MHz, CDCl$_3$): δ 10.26 (s, 1H), 8.98-9.02 (m, 1H), 8.59-8.63 (m, 1H), 7.98-8.01 (m, 1H), 7.36 (t, J=7.9, 1H); $^{13}$C NMR (151 MHz, CDCl$_3$): δ 165.5, 158.2, 142.1, 137.2, 133.6, 131.1, 127.5, 95.0; UPLCMS [M+H] m/z calc.

3(3-fluoro-4-methylphenyl)-1,2,4,5-tetrazine (UB-007). The compound was obtained from 3-Fluoro-4-methylbenzonitrile (0.54 g, 4.00 mmol) following general procedure C. The crude was purified using flash chromatography (95/5 Heptane/EtOAc) to yield 0.400 g of a red solid. Recrystallization from heptane afforded 0.21 g (28%) of UB-007 as a red crystals. R.f.=0.4 (Heptane/EtAOc 80/20); mp=89-91° C.; $^1$H-NMR (CDCl$_3$, 400 MHz): 2.41 (s, 3H, CH$_3$), 7.43 (pseudo t, J=7.8 Hz, 1H, Ar—H), 8.25-8.30 (m, 1H, Ar—H), 8.31-8.36 (m 1H, Ar—H), 10.21 (s, 1H, Ar—H); $^{13}$C-NMR (CDCl$_3$, 100 MHz): 31.9, 114.9 (J$_{C-F}$=25.1 Hz), 123.8 (J$_{C-F}$=3.5 Hz), 130.9 (J$_{C-F}$=17.4 Hz), 131.1 (J$_{C-F}$=8.3 Hz), 157.8, 161.8 (J$_{C-F}$=246.1 Hz), 165.8.

3-(3-Iodo-4-methylphenyl)-1,2,4,5-tetrazine (RGV_100). The compound was obtained from 3-Iodo-4-methylbenzonitrile (972 mg, 4.00 mmol) following general procedure C. The crude was purified using flash chromatography (95/5 Heptane/EtOAc) followed by recrystallization from n-Heptane afforded 0.21 g (18%) of RGV_100 as red crystals. Rf: 0.42 (nHeptane:10% EtOAc); $^1$H NMR (600 MHz, Chloroform-d) δ 10.21 (s, 1H), 9.08 (s, 1H), 8.50 (d, J=9.7 Hz, 1H), 7.46 (d, J=8.0 Hz, 1H), 2.56 (s, 3H); $^{13}$C NMR (600 MHz, CDCl$_3$) δ 165.24, 157.88, 147.21, 138.55, 130.72, 130.45, 127.85, 101.69, 28.46.

3(3-fluoro-4-(trifluoromethyl)phenyl)-1,2,4,5-tetrazine (UB-083). The compound was obtained from 3-fluoro-4-(trifluoromethyl)benzonitrile (0.75 g, 4.00 mmol) following general procedure C. The crude was purified using flash chromatography (95/5 Heptane/EtOAc) to give 0.37 g of a red solid that upon recrystallization from heptane afforded 0.21 g (21%) of UB-083 as a red solid. R.f.=0.41 (Heptane/EtOAc); m.p.: ; $^1$H-NMR (CDCl$_3$, 400 MHz): 7.89 (pseudo t, J=7.6 Hz, 1H, Ar—H), 8.50 (d, J=11.0 Hz, 1H, Ar—H), 8.57 (d, J=8.2 Hz, 1H, Ar—H), 10.35 (s, 1H, Ar—H); $^{13}$C-NMR (CDCl$_3$, 100 MHz): 116.6 (J$_{C-F}$=23.6 Hz), 120.7, 122.4 (m), 123.5, 128.7 (J$_{C-F}$=4.1 Hz), 128.4 (J$_{C-F}$=1.8, 4.4 Hz), 158.3, 160.3 (J$_{C-F}$=2.1, 258.1 Hz), 164.8 (J$_{C-F}$=2.9 Hz).

3-(3-fluoro-4-methoxyphenyl)-1,2,4,5-tetrazine (UB-008). The compound was obtained from 3-Fluoro-4-methoxylbenzonitrile (0.60 g, 4.00 mmol) following general procedure C. The crude was purified using flash chromatography (85/15 Heptane/EtOAc) to yield 0.430 g of a red solid. Recrystallization from Heptane afforded 0.24 g (29%) of UB-008 as a red solid. R.f.=0.39 (Heptyane/EtOAc 80/20); mp=157-159° C.; $^1$H-NMR (CDCl$_3$, 400 MHz): 4.04 (s, 3H, CH$_3$), 7.43 (pseudo t, J=8.5 Hz, 1H, Ar—H), 8.35-8.41 (m, 1H, Ar—H), 8.43-8.48 (m, 1H, Ar—H), 10.18 (s, 1H, Ar—H); $^{13}$C-NMR (CDCl$_3$, 100 MHz): δ6.4, 113.5 (J$_{C-F}$=2.2 Hz), 115.8 (J$_{C-F}$=20.8 Hz), 124.3 (J$_{C-F}$=7.2 Hz), 125.3 (J$_{C-F}$=3.6 Hz), 152.1 (J$_{C-F}$=10.7 Hz), 152.7 (J$_{C-F}$=247.7 Hz), 157.5, 165.5.

3-(3-Iodo-4-methoxyphenyl)-1,2,4,5-tetrazine (RGV_106). The compound was obtained from 3-Iodo-4-methoxylbenzonitrile (1.03 g, 4.00 mmol) following general procedure C. The crude was purified using flash chromatography (95/5 Heptane/EtOAc) to yield after recrystallization with n-Heptane 0.26 g (20%) as a red solid. Rf=0.30 (nHeptane:20% EtOAc); $^1$H NMR (600 MHz, Chloroform-d) δ 10.16 (s, 1H), 9.07 (s, 1H), 8.62 (d, J=10.8 Hz, 1H), 7.01 (d, J=8.7 Hz, 1H), 4.01 (s, 3H); $^{13}$C NMR (600 MHz, CDCl$_3$) δ 165.20, 162.20, 157.70, 139.67, 130.28, 125.84, 111.17, 86.92, 56.85.

trile (0.99 g, 4.00 mmol) following general procedure C. The crude was purified using flash chromatography (95/5 Heptane/EtOAc) to yield 0.33 g (27%) of UB-090 as a red solid. R.f.=0.39 (Heptane/EtOAc 80/20); m.p.=; $^1$H-NMR (CDCl$_3$, 400 MHz): 7.92 (dd, J=6.2, 8.3 Hz, 1H, Ar—H), 8.07 (dd, J=1.9, 8.3 Hz, 1H, Ar—H), 8.19 (dd, J=1.9, 8.7 Hz, 1H, Ar—H), 10.19 (s, 1H, Ar—H); $^{13}$C-NMR (CDCl$_3$, 100 MHz): δ7.2 (J$_{C\text{-}F}$=25.7 Hz), 113.8 (J$_{C\text{-}F}$=26.7 Hz), 124.0 (J$_{C\text{-}F}$=3.6 Hz), 132.8 (J$_{C\text{-}F}$=7.6 Hz), 139.6 (J$_{C\text{-}F}$=1.9 Hz), 157.0, 161.4 (J$_{C\text{-}F}$=246.8 Hz), 164.3 (J$_{C\text{-}F}$=2.9 Hz).

3-(4-chloro-3-fluorophenyl)-1,2,4,5-tetrazine (UB-009). The compound was obtained from 3-Fluoro-4-chlorobenzonitrile (0.62 g, 4.00 mmol) following general procedure C. The crude was purified using flash chromatography (95/5 Heptane/EtOAc) to yield g of a red solid. Recrystallization from iPrOH afforded 0.18 g (21%) of UB-009 as a red crystals. R.f.=0.41 (Heptane/EtOAc 80/20); mp=89-91° C.; $^1$H-NMR (CDCl$_3$, 400 MHz): 7.73 (dd, J=6.9, 8.4 Hz, 1H, Ar—H), 8.24 (ddd, J=0.7, 2.0, 8.3 Hz, 1H, Ar—H), 8.30 (dd, J=2.0, 9.3 Hz, 1H, Ar—H), 10.20 (s, 1H, Ar—H); $^{13}$C-NMR (CDCl$_3$, 100 MHz): 115.2 (J$_{C\text{-}F}$=21.2 Hz), 115.9 (J$_{C\text{-}F}$=25.1 Hz), 124.8 (J$_{C\text{-}F}$=3.7 Hz), 132.8 (J$_{C\text{-}F}$=3.7 Hz), 132.8 (J$_{C\text{-}F}$=7.5 Hz), 158.0, 159.8 (J$_{C\text{-}F}$=249.0 Hz), 165.

3-(4-bromo-3-fluorophenyl)-1,2,4,5-tetrazine (UB-010). The compound was obtained from 3-Fluoro-4-bromobenzonitrile (0.80 g, 4.00 mmol) following general procedure C. The crude was purified using flash chromatography (95/5 Heptane/EtOAc) to yield 0.350 g of a red solid. Recrystallization from heptane afforded 0.20 g (20%) of UB-010 as a red crystals. R.f.=0.42 (Heptane/EtOAc 80/20); mp=98-100° C.; $^1$H-NMR (CDCl$_3$, 400 MHz): 7.63-7.72 (m, 1H, Ar—H), 8.37-8.51 (m, 2H, Ar—H), 10.28 (s, 1H, Ar—H); $^{13}$C-NMR (CDCl$_3$, 100 MHz): 116.2 (J$_{C\text{-}F}$=23.7 Hz), 124.5 (J$_{C\text{-}F}$=3.8 Hz), 126.7 (J$_{C\text{-}F}$=17.7 Hz), 131.8, 132.0 (J$_{C\text{-}F}$=7.3 Hz), 158.0, 158.7 (J$_{C\text{-}F}$=250.5 Hz), 165.1 (J$_{C\text{-}F}$=3.0 Hz).

3-(3-fluoro-4-Iodophenyl)-1,2,4,5-tetrazine (UB-090). The compound was obtained from 3-Fluoro-4-iodobenzoni- 3-(4-hydroxy-3-fluorophenyl)-1,2,4,5-tetrazine (UB-011). The compound was obtained from 3-Fluoro-4-hydroxybenzonitrile (0.55 g, 4.00 mmol) following general procedure C. The crude was purified using flash chromatography (40/60 Heptane/EtOAc) to yield 0.220 g of a red solid. Crystallization from toluene afforded 0.15 g (19%) of UB-011 as a red crystals. R.f.=0.26 (Heptane/EtOAc 80/20); mp=165-167° C.; $^1$H-NMR (CD$_3$OD, 400 MHz): 7.14 (pseudo t, J=8.7 Hz, 1H, Ar—H), 8.11-8.35 (m, 2H, Ar—H), 10.24 (s, 1H, Ar—H); $^{13}$C-NMR (CD$_3$OD, 100 MHz): 115.2 (J$_{C\text{-}F}$=21.1 Hz), 118.1 (J$_{C\text{-}F}$=3.1 Hz), 123. (J$_{C\text{-}F}$=6.7 Hz), 124.8 (J$_{C\text{-}F}$=3.1 Hz), 149.9 (J$_{C\text{-}F}$=12.9 Hz), 151.8 (J$_{C\text{-}F}$=241.9 Hz), 157.4, 165.5.

2-Fluoro-4-(1,2,4,5-tetrazin-3-yl)benzoic acid (UB-096). The compound was obtained from 2-fluoro-4-cyanobenzoic acid (0.66 g, 4.00 mmol) following general procedure C. The crude was purified using flash chromatography (30/70 Heptane/EtOAc) to yield 0.360 g of a red solid. The powder was triturated in DCM and fileted to afford 0.32 g (36%) of UB-96 as a pink solid. mp=228-230° C.; $^1$H-NMR (MeOD, 600 MHz): 8.20 (pseudo t, J=7.74 Hz, 1H, Ar—H), 8.40 (dd, J=1.6, 11.5 Hz, 1H, Ar—H), 8.50 (dd, J=1.6, 8.1 Hz, 1H, Ar—H), 10.44 (s, 1H, Ar—H); $^{13}$C-NMR (MeOD, 150 MHz): 115.8 (J$_{C\text{-}F}$=25.7 Hz), 122.8 (J$_{C\text{-}F}$=10.6 Hz), 123.1 (J$_{C\text{-}F}$=4.0 Hz), 132.8, 138.0 (J$_{C\text{-}F}$=8.8 Hz), 158.2, 162.1 (J$_{C\text{-}F}$=259.0 Hz), 165.0 (J$_{C\text{-}F}$=2.7 Hz), 165.1 (J$_{C\text{-}F}$=3.3 Hz).

Methyl 2-fluoro-4-(1,2,4,5-tetrazin-3-yl)benzoate
(UB-102)

2-Fluoro-4-(1,2,4,5-tetrazin-3-yl)benzoic acid (0.20 g, 0.90 mmol) was solubilized in MeOH (30 mL) and then a 4 M solution of HCl in dioxane (2.0 mL) was added. The reaction as stirred for 3 h and then the solvent was removed under reduced pressure. The compound was purified by flash chromatography (90/10 heptane/EtoAc) and recrystallized from heptane to give 0.14 g (66%) of UB-102 as a red solid. R.f.=0.41 (Heptane/EtOAc 80/20); mp=° C.; $^1$H-NMR (CDCl$_3$, 400 MHz): 3.92 (s, 3H, CH$_3$), 8.06-8.12 (m, 1H, Ar—H), 8.35 (dd, J=1.6, 11.3 Hz, 1H, Ar—H), 8.41 (dd, J=1.6, 8.2 Hz, 1H, Ar—H), 10.24 (s, 1H, Ar—H); $^{13}$C-NMR (CDCl$_3$, 100 MHz): δ2.7, 116.7 (J$_{C\text{-}F}$=25.5 Hz), 122.6 (J$_{C\text{-}F}$=10.4 Hz), 133.2 (J$_{C\text{-}F}$=1.2 Hz), 137.3 (J$_{C\text{-}F}$=8.9 Hz), 116.7 (J$_{C\text{-}F}$=25.5 Hz), 158.1, 162.1 (J$_{C\text{-}F}$=261.3 Hz), 164.1 (J$_{C\text{-}F}$=3.8 Hz), 165.1 (J$_{C\text{-}F}$=2.7 Hz).

Tert-butyl 2-fluoro-4-(1,2,4,5-tetrazin-3-yl)benzoate (UB-102). Tert-butyl 4-cyano-2-fluorobenzoate: 4-Cyano-2-fluorobenzoic acid (1.09 g, 6.54 mmol) was dissolved in t-BuOH (9 mL) and THF (3 mL). Boc anhydride (2.90 g, 13.27 mmol) was added followed by DMAP (0.24 g, 1.99 mmol). The mixture was stirred at RT under N$_2$ for 12 h. The solvents were removed. The residue was dissolved in EtOAc and washed with saturated aqueous NaHCO$_3$ and brine. It was dried over MgSO$_4$ and concentrated to give 1.25 g (85%) of tert-butyl 4-cyano-2-fluorobenzoate as white solid. m.p.: 61-63° C.; $^1$H-NMR (CDCl$_3$, 600 MHz): 1.62 (s, 9H, C(CH$_3$)$_3$), 7.43 (dd, J=1.5, 9.7 Hz, 1H, Ar—H), 7.50 (dd, J=1.5, 8.1 Hz, 1H, Ar—H), 7.43 (dd, J=7.0, 8.1 Hz, 1H, Ar—H); $^{13}$C-NMR (CDCl$_3$, 150 MHz): 28.1, 83.4, 116.79 (J$_{C\text{-}F}$=2.7 Hz), 116.85 (J$_{C\text{-}F}$=9.5 Hz), 120.8 (J$_{C\text{-}F}$=26.3 Hz), 125.1 (J$_{C\text{-}F}$=10.5 Hz), 127.5 (J$_{C\text{-}F}$=4.6 Hz), 132.9 (J$_{C\text{-}F}$=1.9 Hz), 161.0 (J$_{C\text{-}F}$=262.6 Hz), 161.9 (J$_{C\text{-}F}$=3.8 Hz).

The final compound was obtained from tert-butyl 4-cyano-2-fluorobenzoate (1.19 g, 5.31 mmol) following general procedure C. The crude was purified using flash chromatography (95/5 Heptane/EtOAc) and recrystallized from Heptane to afford 0.21 g (14%) of UB-112 as a pink solid. R.f.=0.41 (Heptane/EtOAc 80/20); mp=° C.; $^1$H-NMR (CDCl$_3$, 400 MHz): 1.66 (s, 9H, C(CH$_3$)$_3$), 8.11 (dd, J=7.2, 8.1 Hz, 1H, Ar—H), 8.41 (dd, J=1.6, 11.3 Hz, 1H, Ar—H), 8.48 (dd, J=1.6, 8.1 Hz, 1H, Ar—H), 10.32 (s, 1H, Ar—H); $^{13}$C-NMR (CDCl$_3$, 100 MHz): 28.2, 82.8, 116.6 (J$_{C\text{-}F}$=25.8 Hz), 123.4 (J$_{C\text{-}F}$=4.0 Hz), 124.6 (J$_{C\text{-}F}$=10.5 Hz), 132.9, 136.6 (J$_{C\text{-}F}$=8.8 Hz), 158.1, 162.0 (J$_{C\text{-}F}$=260.2 Hz), 162.7 (J$_{C\text{-}F}$=3.7 Hz), 165.2 (J$_{C\text{-}F}$=2.7 Hz).

2-fluoro-4-(1,2,4,5-tetrazin-3-yl)benzamide (UB-022). 4-Cyano-2-fluorobenzamide: To a solution of 4-cyano-2-fluorobenzoic acid (0.99 g, 6.0 mmol) in acetonitrile (20 ml) was added 1,1'-carbonyldiimidazole (1.46 g, 9.0 mmol). The mixture was stirred at room temperature for 45 min, before addition of aqueous ammonium hydroxide solution (35%, 20 ml). The reaction mixture was stirred for 45 min and ice cold water (15 ml) was added.

The precipitate was collected by filtration and dried to give the title compound 0.78 g (79%) of 4-cyano-2-fluo-robenzamide as a white solid. m.p: 226-228° C.; $^1$H-NMR (DMSO-d$_6$, 400 MHz): 7.71-7.82 (m, 2H, Ar—H), 7.86 (br s, 1H, NH), 7.91-8.02 (m, 2H, Ar—H+NH); $^{13}$C-NMR (DMSO-d$_6$, 100 MHz): 114.6 (J$_{C\text{-}F}$=9.9 Hz), 117.7 (J$_{C\text{-}F}$=2.7 Hz), 120.8 (J$_{C\text{-}F}$=26.7 Hz), 129.2 (J$_{C\text{-}F}$=4.0 Hz), 129.6 (J$_{C\text{-}F}$=15.7 Hz), 131.6 (J$_{C\text{-}F}$=4.0 Hz), 158.9 (J$_{C\text{-}F}$=251.4 Hz), 164.6.

The final compound was obtained from 4-cyano-2-fluo-robenzamide (0.78 g, 4.75 mmol) following general procedure C. The crude was purified using flash chromatography (90/10 DCM/MeOH) to yield 0.21 g (20%) of UB-22 as a pink solid. R.f.=0.32 (Heptane/EtOAc 60/40); mp=220-222° C.; $^1$H-NMR (DMSO-d$_6$, 400 MHz): 7.83 (br s, 1H, NH), 7.93 (pseudo t, J=7.7 Hz, 1H, Ar—H), 7.97 (br s, 1H, NH), 8.30 (dd, J=1.6, 11.1 Hz, 1H, Ar—H), 8.39 (dd, J=1.6, 8.0 Hz, 1H, Ar—H), 10.68 (s, 1H, Ar—H); $^{13}$C-NMR (DMSO-d$_6$, 100 MHz): 115.6 (J$_{C\text{-}F}$=25.4 Hz), 124.1 (J$_{C\text{-}F}$=3.4 Hz), 128.2 (J$_{C\text{-}F}$=15.2 Hz), 131.8 (J$_{C\text{-}F}$=3.4 Hz), 136.5 (J$_{C\text{-}F}$=8.5 Hz), 158.8, 159.9 (J$_{C\text{-}F}$=250.1 Hz), 164.8 (J$_{C\text{-}F}$=2.9 Hz), 165.1.

2-fluoro-4-(1,2,4,5-tetrazin-3-yl)aniline (UB-030). Tert-butyl (4-cyano-2-fluorophenyl)carbamate: 4-Amino-3-fluo-robenzonitrile (1.0 g, 7.34 mmol) was heated at reflux with Boc₂O (4.81 g, 22.04 mmol) and DMAP (0.09 g, 0.73 mmol) in THF (50 mL) overnight. The reaction mixture was evaporated to dryness in vacuo, and the residue was dissolved in dichloromethane (50 mL). TFA (1.6 mL) was then added. The mixture was stirred at room temperature for 3 h. The mixture was made basic using concentrated aqueous ammonia, and then extracted with water. The organic portion was dried with Na₂SO₄, and the solvents were evaporated to dryness in vacuo. The crude was purified by flash chromatography (90/10 Heptane/EtOAc) to give 1.21 g (70%) of tert-butyl (4-cyano-2-fluorophenyl)carbamate as a white solid. m.p.: 108-110° C.; ¹H-NMR (DMSO-d₆, 400 MHz): 1.48 (s, 9H, C(CH₃)₃), 7.58-7.66 (m, 1H, Ar—H), 7.78-7.88 (m, 1H, Ar—H), 7.99 (pseudo t, J=8.3 Hz, 1H, Ar—H), 9.54 (br s, 1H, NH); ¹³C-NMR (DMSO-d₆, 100 MHz): 28.4, 80.9, 105.6 ($J_{C-F}$=9.3 Hz), 118.4 ($J_{C-F}$=2.6 Hz), 119.8 ($J_{C-F}$=23.3 Hz), 123.0 ($J_{C-F}$=2.7 Hz), 129.7 ($J_{C-F}$=3.5 Hz), 132.6 ($J_{C-F}$=11.0 Hz), 152.4 ($J_{C-F}$=247.9 Hz), 152.9.

Tert-butyl (2-fluoro-4-(1,2,4,5-tetrazin-3-yl)phenyl)car-bamate: The compound was obtained from tert-butyl (4-cyano-2-fluorophenyl)carbamate (1.15 g, 4.86 mmol) following general procedure C. The crude was purified using flash chromatography (90/10 Heptane/EtOAc) to yield 0.31 g (22%) of tert-butyl (2-fluoro-4-(1,2,4,5-tetrazin-3-yl)phe-nyl)carbamate as a red solid. R.f.=0.41 (Heptane/EtOAc 80/20); m.p: 181-183° C.; ¹H-NMR (CDCl₃, 600 MHz): 1.58 (s, 9H, C(CH₃)₃), 7.02 (br s, 1H, NH), 8.35 (dd, J=1.8, 12.1 Hz, 1H, Ar—H), 8.39-8.47 (m, 2H, Ar—H), 10.19 (s, 1H, Ar—H); ¹³C-NMR (CDCl₃, 150 MHz): 28.2, 82.0, 114.4 ($J_{C-F}$=22.0 Hz), 119.7, 125.2 ($J_{C-F}$=2.9 Hz), 125.7 ($J_{C-F}$=7.9 Hz), 131.9 ($J_{C-F}$=9.9 Hz), 151.80, 151.84 ($J_{C-F}$=243.2 Hz), 157.6, 165.4 ($J_{C-F}$=3.3 Hz).

To a solution of tert-butyl (2-fluoro-4-(1,2,4,5-tetrazin-3-yl)phenyl)carbamate (0.20 g, 0.69 mmol) in DCM (4 mL) was added TFA (4 mL). The reaction was stirred at room temperature for 10 minutes. The solvent was then evaporated under reduced pressure to give 0.14 g of crude. The compound was recrystallized from Heptane to give 0.12 g (91%) of UB-30 as a red solid. m.p.: 168-170° C.; ¹H-NMR (CDCl₃, 400 MHz): 4.15 (br s, 2H, NH₂), 6.94 (pseudo t, J=8.6 Hz, 1H, Ar—H), 8.20-8.31 (m, 2H, Ar—H), 10.10 (s, 1H, Ar—H); ¹³C-NMR (CDCl₃, 100 MHz): 115.1 ($J_{C-F}$=20.9 Hz), 116.4 ($J_{C-F}$=3.9 Hz), 121.3 ($J_{C-F}$=7.3 Hz), 125.5 ($J_{C-F}$=2.9 Hz), 139.7 ($J_{C-F}$=12.9 Hz), 151.3 ($J_{C-F}$=239.9 Hz), 157.1, 165.7.

N-(2-Fluoro-4-(1,2,4,5-tetrazin-3-yl)phenyl)acetamide (UB-148). N-(4-cyano-2-fluorophenyl)acetamide: To a solution of 4-amino-3-fluorobenzonitrile (0.82 g, 6.00 mmol) in DCM (30.0 mL) was added acetic anhydride (0.80 mL, 8.40 mmol). The mixture was stirred at room temperature for 12 h. The suspension was filtered and the solvent removed under vacuum. Purification by flash chromatography (70/30 Heptane/EtOAc) afforded 0.90 g of N-(4-cyano-2-fluoro-phenyl)acetamide as a white solid. R.f.=0.5 (Heptane/EtOAc 60/40); m.p.=171-173° C.; ¹H-NMR (DMSO-d₆, 400 MHz): 2.15 (s, 3H, CH₃), 7.65 (dt, J=1.3, 8.5 Hz, 1H, Ar—H), 7.88 (dd, J=1.9, 11.1 Hz, 1H, Ar—H), 8.28 (t, J=8.2 Hz, 1H, Ar—H), 10.12 (br s, 1H, NH); ¹³C-NMR (DMSO-d₆, 100 MHz): 24.3, 106.2 ($J_{C-F}$=9.4 Hz), 106.2 ($J_{C-F}$=9.4 Hz), 118.4 ($J_{C-F}$=2.7 Hz), 119.8 ($J_{C-F}$=23.4 Hz), 123.3 ($J_{C-F}$=2.8 Hz), 129.8 ($J_{C-F}$=3.6 Hz), 132.1 ($J_{C-F}$=11.2 Hz), 152.0 ($J_{C-F}$=247.2 Hz), 169.9.

The final compound was obtained from N-(4-cyano-2-fluorophenyl)acetamide (0.71 g, 4.00 mmol) following general procedure C. The crude was purified using flash chro-matography (60/40 Heptane/EtOAc) to yield 0.37 g (40%) of UB-148 as a red solid. R.f.=0.25 (Heptane/EtOAc 60/40); m.p: ° C.; ¹H-NMR (DMSO-d₆, 400 MHz): 2.18 (s, 3H, CH₃), 8.13-8.48 (m, 3H, Ar—H), 10.09 (br s, 1H, NH), 10.58 (s, 1H, Ar—H); ¹³C-NMR (DMSO-d₆, 100 MHz): 24.3, 114.7 ($J_{C-F}$=22.1 Hz), 123.7, 124.7 ($J_{C-F}$=3.3 Hz), 128.0 ($J_{C-F}$=7.9 Hz), 131.4 ($J_{C-F}$=11.2 Hz), 153.2 ($J_{C-F}$=246.0 Hz), 158.4, 164.9 ($J_{C-F}$=3.0 Hz), 169.8.

(2-Fluoro-4-(1,2,4,5-tetrazin-3-yl)phenyl)methanamine hydrochloride (UB-038). 4-((1,3-dioxoisoindolin-2-yl) methyl)-3-fluorobenzonitrile: 4-(Bromomethyl)-3-fluo-robenzonitrile (3.0 g, 14.01 mmol) was dissolved in DMF (20 mL). Phthalimide potassium salt (2.89 g, 15.41) was added and the mixture was stirred for 9 h at 130° C. After cooling to r.t., the mixture was poured on ice. The solid was filtered off. Ethyl acetate and water were added and extracted with ethyl acetate. The organic phase was washed with water, dried, filtered and evaporated to give a light brown solid. Crystallization from EtOAc afforded 3.30 g (84%) of 4-((1,3-dioxoisoindolin-2-yl)methyl)-3-fluorobenzonitrile as a white solid. m.p.: 188-190° C.; $^1$H-NMR (CDCl$_3$, 400 MHz): 4.98 (s, 2H, CH$_2$), 7.35-7.51 (m, 3H, Ar—H), 7.73-7.81 (m, 2H, Ar—H), 7.84-7.91 (m, 2H, Ar—H); $^{13}$C-NMR (CDCl$_3$, 100 MHz): 35.1 ($J_{C-F}$=4.6 Hz), 113.2 ($J_{C-F}$=9.4 Hz), 117.3 ($J_{C-F}$=2.9 Hz), 119.3 ($J_{C-F}$=24.9 Hz), 123.6, 128.3 ($J_{C-F}$=4.0 Hz), 129.1 ($J_{C-F}$=14.6. Hz), 131.8, 134.4, 160.0 ($J_{C-F}$=252.2 Hz), 167.5.

4-(Aminomethyl)-3-fluorobenzonitrile hydrochloride: To a solution of 4-((1,3-dioxoisoindolin-2-yl)methyl)-3-fluorobenzonitrile (3.0 g, 10.70 mmol) in EtOH (5 mL) was added hydrazine hydrate (5 mL). The reaction was then refluxed for 2 h and a white precipitate was formed. The reaction was diluted with NaOH solution (10%, 40 mL) and extracted with EtOAc (3×30 mL). The organic portion was dried with Na$_2$SO$_4$, filtered and the solvents was evaporated to dryness in vacuo. The crude was solubilized in Et$_2$O, filtered and treated with HCl in Et$_2$O (2 mL, 2 M). The solid obtained was filtered and recrystallized from MeOH to give 1.51 g (76%) of 4-(aminomethyl)-3-fluorobenzonitrile hydrochloride as a yellow solid. m.p.: 151-153° C.; $^1$H-NMR (DMSO-d$_6$, 400 MHz): 4.13 (s, 2H, CH$_2$), 7.76-7.88 (m, 2H, Ar—H), 7.95 (d, J=9.9 Hz, 1H, Ar—H), 8.73 (br s, 3H, NH$_3$$^+$); $^{13}$C-NMR (DMSO-d$_6$, 100 MHz): 35.8 ($J_{C-F}$=4.4 Hz), 113.4 ($J_{C-F}$=10.2 Hz), 117.8 ($J_{C-F}$=3.0 Hz), 119.9 ($J_{C-F}$=25.6 Hz), 127.7 ($J_{C-F}$=14.8 Hz), 129.3 ($J_{C-F}$=3.9 Hz), 132.8 ($J_{C-F}$=3.9 Hz), 160.1 ($J_{C-F}$=249.5 Hz).

Tert-butyl 4-cyano-2-fluorobenzylcarbamate: 4-(Aminomethyl)-3-fluorobenzonitrile hydrochloride (1.5 g, 8.04 mmol) and triethylamine (2.35 mL, 16.87 mmol) were dissolved in anhydrous DCM (40 mL) at 0° C. To this stirred solution was added di-tert-butyl dicarbonate (2.10 g, 9.64 mmol), and the reaction allowed to warm to room temperature and stirred for 16 hours. The reaction mixture was evaporated in vacuo, and the residue was re-dissolved in diethyl ether (50 mL), which was washed successively with 0.5 M aq. HCl (2×25 mL), saturated NaHCO$_3$ (2×25 mL) and brine (25 mL). The organic layer was dried with MgSO$_4$, filtered and evaporated in vacuo to give an off-white solid. The residue was purified by flash column chromatography (Heptane/EtOAc=85/15) to afford 1.51 g (75%) od tert-butyl 4-cyano-2-fluorobenzylcarbamate as an orange solid. m.p.: 51-53° C.; $^1$H-NMR (CDCl$_3$, 400 MHz): 1.47 (s, 9H, C(CH$_3$)$_3$), 4.42 (d, J=4.4 Hz, 2H, CH$_2$), 4.99 (br s, 1H, NH), 7.36 (dd, J=1.4, 9.4 Hz, 1H, Ar—H), 7.42-7.56 (m, 2H, Ar—H); $^{13}$C-NMR (CDCl$_3$, 100 MHz): 28.2, 30.0, 79.8, 112.1 ($J_{C-F}$=9.5 Hz), 117.4 ($J_{C-F}$=2.9 Hz), 118.7 ($J_{C-F}$=25.0 Hz), 128.2 ($J_{C-F}$=3.9 Hz), 130.1 ($J_{C-F}$=5.0 Hz), 132.6 ($J_{C-F}$=15.5 Hz), 156.0, 159.9 ($J_{C-F}$=249.8 Hz).

Tert-butyl 2-fluoro-4-(1,2,4,5-tetrazin-3-yl)benzylcarbamate: The compound was obtained from tert-butyl 4-cyano-2-fluorobenzylcarbamate (1.51 g, 5.99 mmol) following general procedure C. The resulting residue was purified using flash chromatography (90/10 Heptane/EtOAc) and recrystallized from Heptane to yield 0.39 g (21%) of tert-butyl 2-fluoro-4-(1,2,4,5-tetrazin-3-yl)benzylcarbamate as a red solid. R.f=0.38 (Heptane/EtOAc 80/20); m.p: ; $^1$H-NMR (CDCl$_3$, 400 MHz): 1.48 (s, 9H, C(CH$_3$)$_3$), 4.49 (d, J=6.3 Hz, 2H, CH$_2$), 5.11 (br s, 1H, NH), 7.60 (pseudo t, J=7.7 Hz, 1H, Ar—H), 8.30 (dd, J=1.7, 10.8 Hz, 1H, Ar—H), 8.41 (dd, J=1.6, 8.0 Hz, 1H, Ar—H), 10.25 (s, 1H, Ar—H); $^{13}$C-NMR (CDCl$_3$, 100 MHz): 28.4, 38.6, 80.0, 115.0 ($J_{C-F}$=24.5 Hz), 124.1, 130.5, 131.6 ($J_{C-F}$=15.0 Hz), 132.6 ($J_{C-F}$=8.5 Hz), 155.8, 157.9, 161.2 ($J_{C-F}$=247.6 Hz), 165.5.

To a solution of tert-butyl 2-fluoro-4-(1,2,4,5-tetrazin-3-yl)benzylcarbamate (0.300 g, 0.98 mmol) in DCM (20 mL) was added a solution of HCl in diethyl ether (1.0 M, 20.0 mL). The mixture was stirred at room temperature for 72 h. The reaction was then concentrated under reduced pressure to give 0.23 g (97%) of UB-38 as a pink solid. m.p.: ; $^1$H-NMR (MeOD, 400 MHz): 2.17 (s, 2H, CH$_2$), 7.74 (pseudo t, J=7.8 Hz, 1H, Ar—H), 8.33 (dd, J=1.6, 10.9 Hz, 1H, Ar—H), 8.43 (dd, J=1.6, 8.0 Hz, 1H, Ar—H), 10.34 (s, 1H, Ar—H); $^{13}$C-NMR (MeOD, 100 MHz): 36.4 ($J_{C-F}$=4.2 Hz), 114.7 ($J_{C-F}$=24.5 Hz), 124.1 ($J_{C-F}$=3.7 Hz), 124.8 ($J_{C-F}$=15.3 Hz), 132.0 ($J_{C-F}$=3.5 Hz), 135.6 ($J_{C-F}$=8.4 Hz), 158.3, 161.4 ($J_{C-F}$=248.3 Hz), 165.1.

3-(3-fluoro-5-methylphenyl)-1,2,4,5-tetrazine (UB-052). The compound was obtained from 3-Fluoro-5-methylbenzonitrile (0.54 g, 4.00 mmol) following general procedure C. The resulting residue was purified using flash chromatography (95/5 Heptane/EtOAc) to afford 0.26 g (34%) of UB-052 as a red oil. R.f.=0.39 (Heptane/EtAOAc 80/20); $^1$H-NMR (CDCl$_3$, 400 MHz): 2.43 (s, 3H, CH$_3$), 7.10 (d, J=9.2 Hz, 1H, Ar—H), 8.05 (d, J=9.4 Hz, 1H, Ar—H), 8.19 (d, J=1.4 Hz, 1H, Ar—H), 10.16 (s, 1H, Ar—H); $^{13}$C-NMR (CDCl$_3$, 100 MHz): 21.4 ($J_{C-F}$=1.8 Hz), 112.3 ($J_{C-F}$=24.4 Hz), 120.8 ($J_{C-F}$=21.2 Hz), 124.7 ($J_{C-F}$=2.7 Hz), 133.3 ($J_{C-F}$=8.9 Hz), 141.8 ($J_{C-F}$=7.7 Hz), 157.9, 163.3 ($J_{C-F}$=246.8 Hz), 165.8 ($J_{C-F}$=3.5 Hz).

3-(3-Iodo-5-methylphenyl)-1,2,4,5-tetrazine (RGV_114). The compound was obtained from 3-Iodo-5-methylbenzonitrile (0.97 g, 4.00 mmol) following general procedure C. The resulting residue was purified using flash chromatography (95/5 Heptane/EtOAc) to yield after crystallization with n-Heptane 0.27 g (22%) as a red solid. Rf: 0.45 (nHeptane:20% EtOAc); $^1$H NMR (400 MHz, Chloroform-d) δ 10.22 (d, J=2.6 Hz, 1H), 8.74 (d, J=9.0 Hz, 1H), 8.38 (d, J=7.2 Hz, 1H), 7.87-7.74 (m, 1H), 2.44 (d, J=4.0 Hz, 3H); $^{13}$C NMR (600 MHz, CDCl$_3$) δ 165.49, 158.09, 142.71, 141.41, 134.34, 133.30, 128.22, 94.99, 21.21.

3-(3-fluoro-5-(trifluoromethyl)phenyl)-1,2,4,5-tetrazine (UB-082). The compound was obtained from 3-fluoro-5-(trifluoromethyl)benzonitrile (0.75 g, 4.00 mmol) following general procedure C. The crude was purified using flash chromatography (95/5 Heptane/EtOAc) to afford 0.23 g (24%) of UB-082 as a red solid. R.f.=0.39 (Heptane/EtOAc 80/20); m.p.=; $^1$H-NMR (CDCl$_3$, 400 MHz): 7.53 (d, J=8.1 Hz, 1H, Ar—H), 8.44 (d, J=9.0 Hz, 1H, Ar—H), 8.65 (s, 1H, Ar—H), 10.25 (s, 1H, Ar—H); $^{13}$C-NMR (CDCl$_3$, 100 MHz): 117.20 (dq, J$_{C-F}$=3.7, 24.6 Hz), 118.41 (J$_{C-F}$=24.1 Hz), 120.9 (m), 122.8 (dd, J$_{C-F}$=2.9, 272.9 Hz), 126.9, 133.9 (qd, J$_{C-F}$=7.9, 34.1 Hz), 134.9 (J$_{C-F}$=8.3 Hz), 158.3, 163.0 (J$_{C-F}$=250.8 Hz), 164.7 (J$_{C-F}$=3.0 Hz).

3-(3-fluoro-5-methoxyphenyl)-1,2,4,5-tetrazine (UB-048). The compound was obtained from 3-Fluoro-5-methoxylbenzonitrile (0.60 g, 4.00 mmol) following general procedure C. The crude was purified using flash chromatography (85/15 Heptane/EtOAc) to yield g of a red solid. Recrystallization from Heptane afforded 0.21 g (26%) of UB-48 as a red solid. R.f.=0.41 (Heptane/EtOAc 80/20); mp=° C.; $^1$H-NMR (CDCl$_3$, 400 MHz): 3.86 (s, 3H, CH$_3$), 6.83 (dd, J=2.4, 10.1 Hz, 1H, Ar—H), 7.87 (ddd, J=1.4, 2.4, 9.1 Hz, 1H, Ar—H), 7.90-7.93 (m, 1H, Ar—H), 10.17 (s, 1H, Ar—H); $^{13}$C-NMR (CDCl$_3$, 100 MHz): δ6.0, 107.0 (J$_{C-F}$=24.9 Hz), 107.7 (J$_{C-F}$=24.7 Hz), 109.0 (J$_{C-F}$=2.8 Hz), 134.0 (J$_{C-F}$=10.7 Hz), 158.0, 161.7 (J$_{C-F}$=11.4 Hz), 164.1 (J$_{C-F}$=246.5 Hz), 165.5.

3-(5-chloro-3-fluorophenyl)-1,2,4,5-tetrazine (UB-067). The compound was obtained from 3-Fluoro-5-chlorobenzonitrile (0.62 g, 4.00 mmol) following general procedure C. The crude was purified using flash chromatography (95/5

Heptane/EtOAc) to yield 0.220 g (26%) of UB-067 as a red crystals. R.f.=0.38 (Heptane/EtOAc 80/20); mp=° C.; $^1$H-NMR (CDCl$_3$, 400 MHz): 7.30 (ddd, J=2.1, 2.4, 8.0 Hz, 1H, Ar—H), 8.17 (ddd, J=1.4, 2.4, 9.0 Hz, 1H, Ar—H), 8.38 (t, J=1.6 Hz, 1H, Ar—H), 10.22 (s, 1H, Ar—H); $^{13}$C-NMR (CDCl$_3$, 100 MHz): 113.6 (J$_{C-F}$=24.2 Hz), 120.7 (J$_{C-F}$=24.7 Hz), 124.7 (J$_{C-F}$=3.3 Hz), 134.7 (J$_{C-F}$=9.2 Hz), 136.6 (J$_{C-F}$=10.2 Hz), 158.2, 163.1 (J$_{C-F}$=251.2 Hz), 164.9 (J$_{C-F}$=3.5 Hz).

3-(5-bromo-3-fluorophenyl)-1,2,4,5-tetrazine (UB-055). The compound was obtained from 3-Fluoro-5-bromobenzonitrile (0.80 g, 4.00 mmol) following general procedure C. The resulting residue was purified using flash chromatography (95/5 Heptane/EtOAc) to yield 0.200 g (20%%) of UB-055 as a red solid. R.f.=0.41 (Heptane/EtOAc 80/20); m.p.=1H-NMR (CDCl$_3$, 400 MHz):7.45 (ddd, J=1.8, 2.4, 7.8 Hz, 1H, Ar—H), 8.21 (ddd, J=1.4, 2.4, 9.1 Hz, 1H, Ar—H), 8.51-8.53 (m, 1H, Ar—H), 10.21 (s, 1H, Ar—H); $^{13}$C-NMR (CDCl$_3$, 100 MHz): 114.0 (J$_{C-F}$=24.0 Hz), 123.6 (J$_{C-F}$=24.5 Hz), 123.9 (J$_{C-F}$=9.5 Hz), 114.09 (J$_{C-F}$=24.0 Hz), 127.2 (J$_{C-F}$=3.3 Hz), 134.9 (J$_{C-F}$=8.9 Hz), 158.2, 163.1 (J$_{C-F}$=252.3 Hz), 164.7 (J$_{C-F}$=3.3 Hz).

3-(3-fluoro-5-Iodophenyl)-1,2,4,5-tetrazine (UB-089). The compound was obtained from 3-Fluoro-5-iodobenzonitrile (0.99 g, 4.00 mmol) following general procedure C. The resulting residue was purified using flash chromatography (95/5 Heptane/EtOAc) to yield 0.31 g (26%) of UB-089 as a red solid. R.f.=0.39 (Heptane/EtOAc 80/20); m.p.=$^1$H-NMR (CDCl$_3$, 400 MHz): 7.61-7.70 (m, 1H, Ar—H), 8.19-8.27 (m, 1H, Ar—H), 8.72 (s, 1H, Ar—H), 10.21 (s, 1H, Ar—H); $^{13}$C-NMR (CDCl$_3$, 100 MHz): 94.4 (J$_{C-F}$=8.0 Hz), 114.8 (J$_{C-F}$=24.1 Hz), 129.9 (J$_{C-F}$=23.7 Hz), 133.0 (J$_{C-F}$=3.3 Hz), 135.0 (J$_{C-F}$=8.5 Hz), 158.2, 162.7 (J$_{C-F}$=253.2 Hz), 164.5 (J$_{C-F}$=3.2 Hz).

3-(5-hydroxy-3-fluorophenyl)-1,2,4,5-tetrazine (UB-072). The compound was obtained from 3-Fluoro-5-hydroxybenzonitrile (0.55 g, 4.00 mmol) following general procedure C. The crude was purified using flash chromatography (70/30 Heptane/EtOAc) to yield 0.23 g (30%) of UB-072 as a red crystals. R.f.=0.28 (Heptane/EtOAc 80/20); mp=° C.; $^1$H-NMR (DMSO-d$_6$, 400 MHz): 6.88-6.96 (m, 1H, Ar—H), 7.65-7.60 (m, 1H, Ar—H), 7.77-7.81 (m, 1H, Ar—H), 10.50 (br s, 1H, OH), 10.62 (s, Ar—H, 1H); $^{13}$C-NMR (DMSO-d$_6$, 100 MHz): 105.3 (J$_{C-F}$=24.4 Hz), 107.3 (J$_{C-F}$=23.8 Hz), 111.3 (J$_{C-F}$=2.4 Hz), 134.9 (J$_{C-F}$=10.9 Hz), 158.8, 160.4 (J$_{C-F}$=12.2 Hz), 164.0 (J$_{C-F}$=243.1 Hz), 165.1 (J$_{C-F}$=3.49 Hz).

3-Fluoro-5-(1,2,4,5-tetrazin-3-yl)benzoic acid (UB-065). The compound was obtained from 3-fluoro-5-cyanobenzoic acid (0.66 g, 4.00 mmol) following general procedure C. The crude was purified using flash chromatography (30/70 Heptane/EtOAc) to yield 0.360 g of a red solid. The powder was triturated in DCM and filtered to afford to 0.21 g (24%) of UB-65 as a pink solid. R.f.=0.31 (Heptane/EtOAc 40/60); mp=; $^1$H-NMR (MeOD, 400 MHz): 7.90 (ddd, J=1.5, 2.6, 8.8 Hz, 1H, Ar—H), 8.42 (ddd, J=1.5, 2.6, 9.2 Hz, 1H, Ar—H), 8.95 (pseudo t, J=1.5 Hz, 1H, Ar—H), 10.32 (s, 1H, Ar—H); $^{13}$C-NMR (MeOD, 100 MHz): 118.3 (J$_{C-F}$=24.7 Hz), 119.9 (J$_{C-F}$=23.2 Hz), 124.6 (J$_{C-F}$=3.0 Hz), 134.5 (J$_{C-F}$=7.2 Hz), 134.9 (J$_{C-F}$=8.2 Hz), 158.3, 163.1 (J$_{C-F}$=247.1 Hz), 165.1, 166.0.

Methyl 3-fluoro-5-(1,2,4,5-tetrazin-3-yl)benzoate (UB-105). 3-Fluoro-5-(1,2,4,5-tetrazin-3-yl)benzoic acid (0.20 g, 0.90 mmol) was solubilized in MeOH (30 mL) and then a 4 M solution of HCl in dioxane (2.0 mL) was added. The reaction as stirred for 3 h and then the solvent was removed under reduced pressure. The compound was purified by flash chromatography (90/10 heptane/EtoAc) and recrystallized from heptane to give 0.18 g (85%) of UB-105 as a red solid. mp=° C.; $^1$H-NMR (CDCl$_3$, 400 MHz): 3.94 (s, 3H, CH$_3$), 7.90-7.98 (m, 1H, Ar—H), 8.43-8.50 (m, 1H, Ar—H), 9-04-9.08 (m, 1H, Ar—H), 10.24 (s, 1H, Ar—H); $^{13}$C-NMR (CDCl$_3$, 100 MHz): δ2.8, 119.3 (J$_{C-F}$=24.2 Hz), 121.0 (J$_{C-F}$=23.3 Hz), 125.1 (J$_{C-F}$=3.1 Hz), 133.7 (J$_{C-F}$=7.5 Hz), 134.1 (J$_{C-F}$=8.1 Hz), 158.2, 163.1 (J$_{C-F}$=249.1 Hz), 165.0 (J$_{C-F}$=3.1 Hz), 165.2 (J$_{C-F}$=3.1 Hz).

Tert-butyl 3-fluoro-5-(1,2,4,5-tetrazin-3-yl)benzoate (UB-113). Tert-butyl 5-cyano-3-fluorobenzoate: 5-Cyano-3-fluorobenzoic acid (1.09 g, 6.54 mmol) was dissolved in t-BuOH (9 mL) and THF (3 mL). Boc anhydride (2.90 g, 13.27 mmol) was added followed by DMAP (0.24 g, 1.99 mmol). The mixture was stirred at RT under N$_2$ for 12 h. The solvents were removed. The residue was dissolved in EtOAc and washed with saturated aqueous NaHCO$_3$ and brine. It was dried over MgSO$_4$ and concentrated to give 1.42 g (97%) of tert-butyl 5-cyano-3-fluorobenzoate: as white solid. m.p.: 78-80° C.; $^1$H-NMR (CDCl$_3$, 400 MHz): 1.53 (s, 9H, C(CH$_3$)$_3$), 7.40-7.49 (m, 1H, Ar—H), 7.81-7.89 (m, 1H, Ar—H), 7.97-8.02 (m, 1H, Ar—H); $^{13}$C-NMR (CDCl$_3$, 100 MHz): 28.0, 83.1, 114.0 (J$_{C-F}$=9.0 Hz), 116.9 (J$_{C-F}$=3.0 Hz), 121.2 (J$_{C-F}$=22.8 Hz), 122.5 (J$_{C-F}$=25.1 Hz), 129.1 (J$_{C-F}$=3.5 Hz), 135.8 (J$_{C-F}$=7.3 Hz), 162.1 (J$_{C-F}$=251.6 Hz), 162.4 (J$_{C-F}$=3.0 Hz).

The final compound was obtained from tert-butyl 5-cyano-3-fluorobenzoate (1.22 g, 5.51 mmol) following general procedure C. The resulting residue was purified using flash chromatography (95/5 Pentane/EtOAc) and recrystallized from Heptane to afford 0.25 g (16%) of UB-113 as a pink solid. R.f.=0.37 (Heptane/EtOAc 80/20); mp=; $^1$H-NMR (CDCl$_3$, 400 MHz): 1.66 (s, 9H, C(CH$_3$)$_3$), 7.91-8.02 (m, 1H, Ar—H), 8.47-8.56 (m, 1H, Ar—H), 9.04 (s, 1H, Ar—H), 10.32 (s, 1H, Ar—H); $^{13}$C-NMR (CDCl$_3$, 100 MHz): 28.1, 82.5, 118.7 (J$_{C-F}$=24.3 Hz), 120.9 (J$_{C-F}$=23.1 Hz), 124.9 (J$_{C-F}$=3.1 Hz), 133.8 (J$_{C-F}$=8.0 Hz), 135.7 (J$_{C-F}$=7.3 Hz), 158.1, 163.0 (J$_{C-F}$=248.6 Hz), 163.6 (J$_{C-F}$=2.9 Hz), 165.3 (J$_{C-F}$=3.1 Hz).

3-fluoro-5-(1,2,4,5-tetrazin-3-yl)benzamide (UB-070). 5-Cyano-3-fluorobenzamide: To a solution of 5-cyano-3-fluorobenzoic acid (0.99 g, 6.0 mmol) in acetonitrile (20 ml) was added 1,1'-carbonyldiimidazole (1.46 g, 9.0 mmol). The mixture was stirred at room temperature for 45 min, before addition of aqueous ammonium hydroxide solution (35%, 20 ml). The reaction mixture was stirred for 45 min and ice cold water (15 ml) was added. The precipitate was collected by filtration and dried to give the title compound 0.77 g (78%) of 5-Cyano-3-fluorobenzamide as a white solid. m.p: 207-209° C.; $^1$H-NMR (DMSO-d$_6$, 400 MHz): 7.78 (br s, 1H, NH), 7.97-8.08 (m, 2H, Ar—H), 8.13-8.18 (m, 1H, Ar—H), 8.21 (br s, 1H, NH); $^{13}$C-NMR (DMSO-d$_6$, 100 MHz): 113.5 (J$_{C-F}$=9.9 Hz), 117.7 (J$_{C-F}$=3.1 Hz), 120.1 (J$_{C-F}$=22.9 Hz), 122.4 (J$_{C-F}$=25.7 Hz), 138.4 (J$_{C-F}$=7.3 Hz), 162.0 (J$_{C-F}$=247.5 Hz), 165.1 (J$_{C-F}$=2.4 Hz).

The final compound was obtained from 4-cyano-2-fluorobenzamide (0.75 g, 4.57 mmol) following general procedure C. The resulting residue was purified using flash chromatography (90/10 DCM/MeoH) to afford 0.36 g (36%) of UB-70 as a pink solid. R.f.=0.31 (Heptane/EtOAc 60/40); mp=° C.; $^1$H-NMR (DMSO-d$_6$, 400 MHz): 7.71 (br s, 1H, NH), 7.99-8.05 (m, 1H, Ar—H), 8.31-8.44 (m, 2H, Ar—H+ NH), 8.88 (s, 1H, Ar—H), 10.69 (s, 1H, Ar—H); $^{13}$C-NMR (DMSO-d$_6$, 100 MHz): 117.3 (J$_{C-F}$=24.1 Hz), 118.8 (J$_{C-F}$=23.0 Hz), 123.6 (J$_{C-F}$=2.9 Hz), 134.9 (J$_{C-F}$=8.2 Hz), 138.3 (J$_{C-F}$=6.9 Hz), 158.9, 162.8 (J$_{C-F}$=245.6 Hz), 164.9 (J$_{C-F}$=3.2 Hz), 166.1 (J$_{C-F}$=2.3 Hz).

3-fluoro-5-(1,2,4,5-tetrazin-3-yl)aniline (UB-087). Ditert-butyl (5-cyano-3-fluorophenyl)carbamate: 3-Amino-5-fluorobenzonitrile (1.0 g, 7.34 mmol) was heated at reflux with Boc$_2$O (4.80 g, 22.04 mmol) and DMAP (0.09 g, 0.73 mmol) in THF (25 mL) overnight. The reaction mixture was evaporated to dryness in vacuo, and the residue was dissolved in dichloromethane (50 mL) and then extracted with water. The organic portion was dried with Na$_2$SO$_4$, and the solvents were evaporated to dryness in vacuo. The crude was purified by flash chromatography (90/10 Heptane/EtOAc) to give 2.25 g (91%) as a white solid. m.p.: 81-83° C.; $^1$H-NMR (CDCl$_3$, 400 MHz): 1.46 (s, 18H, 2×C(CH$_3$)$_3$), 7.19 (td, J=2.2, 8.9 Hz, 1H, Ar—H), 7.29-7.36 (m, 2H, Ar—H); $^{13}$C-NMR (CDCl$_3$, 100 MHz): 27.9, 84.1, 113.7

(J$_{C-F}$=10.8 Hz), 116.8 (J$_{C-F}$=3.5 Hz), 118.1 (J$_{C-F}$=24.6 Hz), 120.9 (J$_{C-F}$=22.6 Hz), 128.1 (J$_{C-F}$=3.6 Hz), 141.8 (J$_{C-F}$=10.5 Hz), 150.7, 162.0 (J$_{C-F}$=251.2 Hz).

Tert-butyl (3-fluoro-5-(1,2,4,5-tetrazin-3-yl)phenyl)carbamate: The compound was obtained from ditert-butyl (5-cyano-3-fluorophenyl)carbamate (1.34 g, 4.00 mmol) following general procedure C. The crude was purified using flash chromatography (85/15 Heptane/EtOAc) to afford 0.33 g (28%) of tert-butyl (3-fluoro-5-(1,2,4,5-tetrazin-3-yl)phenyl)carbamate as a red solid. R.f.=0.36 (Heptane/EtOAc 80/20); m.p.: ; $^1$H-NMR (DMSO-d$_6$, 400 MHz): 1.52 (s, 9H, C(CH$_3$)$_3$), 7.60-7.67 (m, 1H, Ar—H), 7.80-7.85 (m, 1H, Ar—H), 8.54 (s, 1H, Ar—H), 9.95 (br s, 1H, NH), 10.63 (s, 1H, Ar—H); $^{13}$C-NMR (DMSO-d$_6$, 100 MHz): 28.5, 80.5, 107.9 (J$_{C-F}$=24.3 Hz), 109.0 (J$_{C-F}$=26.6 Hz), 113.6 (J$_{C-F}$=2.6 Hz), 134.6 (J$_{C-F}$=10.1 Hz), 143.0 (J$_{C-F}$=11.5 Hz), 153.1, 158.8, 163.2 (J$_{C-F}$=241.7 Hz), 165.1 (J$_{C-F}$=3.8 Hz).

To a solution of tert-butyl (3-fluoro-5-(1,2,4,5-tetrazin-3-yl)phenyl)carbamate (0.15 g, 0.51 mmol) in DCM (5 mL) was added TFA (5 mL). The reaction was stirred at room temperature for 10 minutes. The solvent was then evaporated under reduced pressure to give 0.14 g of crude. The compound was recrystallized from Heptane to give 0.45 g (46%) of UB-87 as a red solid. R.f.=0.31 (Heptane/EtOAc 80/20); m.p.: ° C.; $^1$H-NMR (MeOD, 400 MHz): 6.63-6.70 (m, 1H, Ar—H), 7.45-7.52 (m, 1H, Ar—H), 7.71 (s, 1H, Ar—H), 10.31 (s, 1H, Ar—H); $^{13}$C-NMR (MeOD, 100 MHz): 102.3 (J$_{C-F}$=25.2 Hz), 104.6 (J$_{C-F}$=24.9 Hz), 109.5 (J$_{C-F}$=2.0 Hz), 134.1 (J$_{C-F}$=10.8 Hz), 151.2 (J$_{C-F}$=11.5 Hz), 157.9, 164.4 (J$_{C-F}$=241.6 Hz), 165.9 (J$_{C-F}$=3.8 Hz).

N-(3-Fluoro-5-(1,2,4,5-tetrazin-3-yl)phenyl)acetamide (UB-150). N-(5-cyano-3-fluorophenyl)acetamide: To a solution of 3-amino-5-fluorobenzonitrile (0.82 g, 6.00 mmol) in DCM (30.0 mL) was added acetic anhydride (0.80 mL, 8.40 mmol). The mixture was stirred at room temperature for 12 h. The suspension was filtered and the solvent removed under vacuum. Purification by flash chromatography (70/30 Heptane/EtOAc) afforded 0.92 g of N-(5-cyano-3-fluorophenyl)acetamide as a white solid. R.f.=0.31 (Heptane/EtOAc 60/40); m.p.=187-189° C.; $^1$H-NMR (DMSO-d$_6$, 400 MHz): 2.09 (s, 3H, CH$_3$), 7.45-7.53 (m, 1H, Ar—H), 7.72-7.80 (m, 2H, Ar—H), 10.45 (br s, 1H, NH); $^{13}$C-NMR (DMSO-d$_6$, 100 MHz): 24.5, 110.9 (J$_{C-F}$=26.2 Hz), 113.2 (J$_{C-F}$=12.1 Hz), 113.7 (J$_{C-F}$=25.5 Hz), (J$_{C-F}$=26.2 Hz), 118.1 (J$_{C-F}$=3.6 Hz), 118.6, 142.3 (J$_{C-F}$=11.8 Hz), 162.2 (J$_{C-F}$=244.3 Hz), 169.7.

The final compound was obtained from N-(4-cyano-2-fluorophenyl)acetamide (0.58 g, 3.25 mmol) following general procedure C. The crude was purified using flash chromatography (60/40 Heptane/EtOAc) to yield 0.19 g (25%) of UB-150 as a red solid. R.f.=0.25 (Heptane/EtOAc 60/40); m.p.: ° C.; $^1$H-NMR (DMSO-d$_6$, 400 MHz): 2.12 (s, 3H, CH$_3$), 7.85-7.93 (m, 2H, Ar—H), 8.51-8.54 (m, 1H, Ar—H), 10.48 (br s, 1H, NH), 10.64 (s, 1H, Ar—H); $^{13}$C-NMR (DMSO-d$_6$, 100 MHz): 24.6, 108.7 (J$_{C-F}$=24.4), 109.9 (J$_{C-F}$=26.6), 114.4 (J$_{C-F}$=2.6), 134.4 (J$_{C-F}$=10.1), 142.4 (J$_{C-F}$=11.5), 08.7 (J$_{C-F}$=24.4), 158.8, 163.1 (J$_{C-F}$=242.2), 165.0 (J$_{C-F}$=3.8), 169.5.

(3-Fluoro-5-(1,2,4,5-tetrazin-3-yl)phenyl)methanamine hydrochloride (UB-115). 5-((1,3-dioxoisoindolin-2-yl) methyl)-3-fluorobenzonitrile: 5-(Bromomethyl)-3-fluorobenzonitrile (1.25 g, 5.84 mmol) was dissolved in DMF (10 mL). Phthalimide potassium salt (1.20 g, 6.42) was added and the mixture was stirred for 9 h at 130° C. After cooling to r.t., the mixture was poured on ice. The solid was filtered off and dried to afford 1.62 g (99%) of 5-((1,3-dioxoisoindolin-2-yl)methyl)-3-fluorobenzonitrile as a white solid. m.p.: 156-158° C.; $^1$H-NMR (CDCl$_3$, 400 MHz): 4.87 (s, 2H, CH$_2$), 7.26-7.32 (m, 1H, Ar—H), 7.39-7.44 (m, 1H, Ar—H), 7.53 (s, 1H, Ar—H), 7.74-7.81 (m, 2H Ar—H), 7.86-7.91 (m, 2H, Ar—H); $^{13}$C-NMR (CDCl$_3$, 100 MHz): 40.4 (J$_{C-F}$=1.9 Hz), 114.2 (J$_{C-F}$=9.7 Hz), 117.2 (J$_{C-F}$=3.3 Hz), 118.6 (J$_{C-F}$=24.6 Hz), 120.7 (J$_{C-F}$=21.8 Hz), 123.7, 128.0 (J$_{C-F}$=3.5 Hz), 131.8, 134.4, 140.4 (J$_{C-F}$=7.6 Hz), 162.3 (J$_{C-F}$=251.4 Hz), 167.7.

5-(Aminomethyl)-3-fluorobenzonitrile hydrochloride: To a solution of 5-((1,3-dioxoisoindolin-2-yl)methyl)-3-fluorobenzonitrile (1.6 g, 5.71 mmol) in EtOH (5 mL) was added hydrazine hydrate (5 mL). The reaction was then refluxed for 2 h and a white precipitate was formed. The reaction was diluted with NaOH solution (10%, 40 mL) and extracted with EtOAc (3×30 mL). The organic portion was dried with Na$_2$SO$_4$, filtered and the solvents was evaporated to dryness in vacuo. The crude was solubilized in Et$_2$O, filtered and treated with HCl in Et$_2$O (2 mL, 2 M). The solid obtained was filtered and recrystallized from MeOH/Et$_2$O to give 0.71 g (67%) of 5-(aminomethyl)-3-fluorobenzonitrile hydrochloride as a yellow solid. m.p.: 159-161° C.; $^1$H-NMR (CD$_3$OD, 400 MHz): 4.26 (s, 2H, CH$_2$), 7.64-7.71 (m, 2H, Ar—H), 7.74-7.79 (m, 1H, Ar—H); $^{13}$C-NMR (CD$_3$OD, 100 MHz): 43.0 (J$_{C-F}$=1.5 Hz), 115.7 (J$_{C-F}$=10.1 Hz), 118.0, 120.8 (J$_{C-F}$=25.2 Hz), 122.4 (J$_{C-F}$=22.7 Hz), 130.1 (J$_{C-F}$=3.8 Hz), 138.9 (J$_{C-F}$=8.0 Hz), 163.8 (J$_{C-F}$=249.8 Hz). Tert-butyl 5-cyano-3-fluorobenzylcarbamate: 5-(Aminomethyl)-3-fluorobenzonitrile hydrochloride (0.7 g, 3.75 mmol) and triethylamine (1.15 mL, 8.25 mmol) were dissolved in anhydrous DCM (20 mL) at 0° C. To this stirred solution was added di-tert-butyl dicarbonate (0.98 g, 4.50 mmol), and the reaction allowed to warm to room temperature and stirred for 16 hours. The reaction mixture was evaporated in vacuo, and the residue was re-dissolved in diethyl ether (50 mL), which was washed successively with 0.5 M aq. HCl (2×25 mL), saturated NaHCO$_3$ (2×25 mL) and brine (25 mL). The organic layer was dried with MgSO$_4$, filtered and evaporated in vacuo to give an off-white solid. The residue was purified by flash column chromatography (Heptane/EtOAc=85/15) to afford 0.51 g (54%) of tert-butyl 5-cyano-2-fluorobenzylcarbamate as an orange solid. m.p.: 82-84° C.; $^1$H-NMR (CDCl$_3$, 400 MHz): 1.39 (s, 9H, C(CH$_3$)$_3$), 4.26 (d, J=6.2 Hz, 2H, CH$_2$), 5.57 (t, J=6.2 Hz, 1H, NH), 7.14-7.24 (m, 2H, Ar—H), 7.32 (s, 1H, Ar—H); $^{13}$C-NMR (CDCl$_3$, 100 MHz): 28.2, 43.3, 80.0, 113.6 (J$_{C-F}$=9.7 Hz), 117.5 (J$_{C-F}$=2.7 Hz), 117.6 (J$_{C-F}$=27.6 Hz), 119.1 (J$_{C-F}$=21.6 Hz), 126.5 (J$_{C-F}$=3.2 Hz), 144.2 (J$_{C-F}$=7.5 Hz), 156.0, 162.3 (J$_{C-F}$=250.4 Hz).

Tert-butyl 3-fluoro-5-(1,2,4,5-tetrazin-3-yl)benzylcarbamate: The compound was obtained from tert-butyl 5-cyano-3-fluorobenzylcarbamate (0.40 g, 1.60 mmol) following general procedure C. The resulting residue was purified using flash chromatography (90/10 heptane/EtOAc) to yield 0.16 g (33%) of tert-butyl 3-fluoro-5-(1,2,4,5-tetrazin-3-yl)benzylcarbamate as red solid. R.f.=0.33 (Heptane/EtOAc 80/20); m.p.: ; $^1$H-NMR (CDCl$_3$, 400 MHz): 1.46 (s, 9H, C(CH$_3$)$_3$), 4.46 (d, J=6.4 Hz, 2H, CH$_2$), 5.21 (t, J=6.4 Hz, 1H, NH), 7.28-7.32 (m, 1H, Ar—H), 8.16-8.24 (m, 1H, Ar—H), 8.35 (s, 1H, Ar—H), 10.26 (s, 1H, Ar—H); $^{13}$C-NMR (CDCl$_3$, 100 MHz): 28.3, 44.0, 80.0, 113.9 (J$_{C-F}$=24.3 Hz), 118.8 (J$_{C-F}$=22.2 Hz), 122.5, 133.7 (J$_{C-F}$=8.6 Hz), 143.5 (J$_{C-F}$=5.8 Hz), 155.9, 158.0, 163.4 (J$_{C-F}$=248.0 Hz), 165.6 (J$_{C-F}$=3.3 Hz).

To a solution of tert-butyl 3-fluoro-5-(1,2,4,5-tetrazin-3-yl)benzylcarbamate (0.14 g, 0.46 mmol) in DCM (20 mL) was added a solution of HCl in diethyl ether (1.0 M, 20.0 mL). The mixture was stirred at room temperature for 72 h. The reaction was then concentrated under reduced pressure to give 0.07 g (63%) of UB-115 as a pink solid. m.p.: ; $^1$H-NMR (MeOD, 400 MHz): 4.23 (s, 2H, CH$_2$), 7.49-7.54 (m, 1H, Ar—H), 8.24-8.30 (m 1H, Ar—H), 8.48 (s, 1H, Ar—H), 10.33 (s, 1H, Ar—H); $^{13}$C-NMR (MeOD, 100 MHz): 42.2, 114.9 (J$_{C-F}$=24.3 Hz), 119.9 (J$_{C-F}$=24.3 Hz), 124.1 (J$_{C-F}$=3.1 Hz), 135.4 (J$_{C-F}$=8.5 Hz), 137.0 (J$_{C-F}$=7.9 Hz), 158.3, 163.3 (J$_{C-F}$=247.4 Hz), 165.1 (J$_{C-F}$=3.3 Hz).

3-(3-fluoro-6-methylphenyl)-1,2,4,5-tetrazine (RGV-117). The compound was obtained from 5-Fluoro-2-methylbenzonitrile (0.54 g, 4.00 mmol) following general procedure C. The resulting residue was purified using flash chromatography (95/5 Heptane/EtOAc) to yield after crystallization with n-Heptane 0.12 g (16%) as a red solid. Rf: 0.37 (nHeptane:10% EtOAc); 1H NMR (600 MHz, Chloroform-d) δ 10.23 (s, 1H), 7.72 (dd, J=8.5, 3.2 Hz, 1H), 7.32-7.27 (m, 1H), 7.08 (dd, J=9.1, 4.2 Hz, 1H), 3.90 (s, 3H); $^{13}$C NMR (600 MHz, Chloroform-d) δ 167.77 (d, J=2.2 Hz), 157.88 (d, J=240.2 Hz), 156.99, 156.28, 154.97 (d, J=2.1 Hz), 122.91 (d, J=7.8 Hz), 120.08 (d, J=22.9 Hz), 118.48 (d, J=25.3 Hz), 113.94 (d, J=7.9 Hz), 56.96.

3-(3-fluoro-6-methoxyphenyl)-1,2,4,5-tetrazine (RGV-116). The compound was obtained from 5-Fluoro-2-methoxylbenzonitrile (0.60 g, 4.00 mmol) following general procedure C. The resulting residue was purified using flash chromatography (95/5 Heptane/EtOAc) to yield after crystallization with n-Heptane 0.13 g (16%) as a red solid. Rf: 0.18 (nHeptane:10% EtOAc); 1H NMR (600 MHz, Chloroform-d) δ 10.23 (s, 1H), 8.26 (s, 1H), 8.12 (d, J=9.4 Hz, 1H), 7.17 (d, J=9.1 Hz, 1H), 2.50 (s, 2H); $^{13}$C NMR (151 MHz, Chloroform-d) δ 165.99 (d, J=3.4 Hz), 164.27 (d, J=247.1 Hz), 162.63, 158.11, 141.97 (d, J=7.8 Hz), 133.45 (d, J=8.9 Hz), 124.81, 120.95 (d, J=21.2 Hz), 112.44 (d, J=24.2 Hz), 21.60.

3-(5-Iodo-2-methoxyphenyl)-1,2,4,5-tetrazine (RGV_105). The compound was obtained from 3-iodo-5-methoxybenzonitrile (1.03 g, 4.00 mmol) following general procedure C. The resulting residue was purified using flash chromatography (95/5 Heptane/EtOAc) to yield after crystallization with n-Heptane 0.19 g (15%) as a red solid. Rf=0.21 (nHeptane:20% EtOAc); $^{1}$H NMR (600 MHz, Chloroform-d) δ 10.21 (s, 1H), 8.21 (s, 1H), 7.82 (d, J=11.1 Hz, 1H), 6.88 (d, J=8.8 Hz, 1H), 3.87 (s, 3H); $^{13}$C NMR (600 MHz, CDCl$_3$) δ 167.31, 158.39, 156.94, 142.10, 140.14, 124.08, 114.62, 82.71, 56.35.

3-(6-chloro-3-fluorophenyl)-1,2,4,5-tetrazine (UB-118). The compound was obtained from 3-Fluoro-6-chlorobenzonitrile (0.62 g, 4.00 mmol) following general procedure C. The crude was purified using flash chromatography (95/5 Heptane/EtOAc) to yield 0.14 g (17%) of UB-118 as a red solid. R.f.=0.48 (Heptane/EtOAc 80/20); m.p.=; $^{1}$H-NMR (CDCl$_3$, 400 MHz): 7.31 (ddd, J=3.0, 7.5, 9.1 Hz, 1H, Ar—H), 7.62 (dd, J=4.8, 8.9 Hz, 1H, Ar—H), 7.76 (dd, J=3.0, 8.4 Hz, 1H, Ar—H), 10.35 (s, 1H, Ar—H); $^{13}$C-NMR (CDCl$_3$, 100 MHz): 119.1 (J$_{C-F}$=25.1 Hz), 119.9 (J$_{C-F}$=22.5 Hz), 128.8 (J$_{C-F}$=3.6 Hz), 132.7 (J$_{C-F}$=8.0 Hz), 132.9 (J$_{C-F}$=8.0 Hz), 157.3, 161.2 (J$_{C-F}$=249.1 Hz), 167.7 (J$_{C-F}$=2.3 Hz).

3-(6-bromo-3-fluorophenyl)-1,2,4,5-tetrazine (UB-002). The compound was obtained from 3-Fluoro-6-bromobenzonitrile (0.40 g, 2.00 mmol) following general procedure C. The resulting residue was purified using flash chromatography (90/10 Heptane/EtOAc) to yield 0.18 g of a red solid. Recrystallization from Heptane afforded 0.15 g (34%) of UB-002 as a red solid. R.f.=0.41 (Heptane/EtOAc 80/20); mp=95-97° C.; $^{1}$H-NMR (CDCl$_3$, 400 MHz): 7.26 (ddd, J=3.0, 7.6, 8.9 Hz, 1H, Ar—H), 7.73 (dd, J=3.0, 8.5 Hz, 1H, Ar—H), 7.81 (dd, J=5.0, 8.9 Hz, 1H, Ar—H), 10.36 (s, 1H, Ar—H); $^{13}$C-NMR (CDCl$_3$, 100 MHz): 16.7 (J$_{C-F}$=3.6 Hz), 119.3 (J$_{C-F}$=24.9 Hz), 120.0 (J$_{C-F}$=22.1 Hz), 134.9 (J$_{C-F}$=8.0 Hz), 135.9 (J$_{C-F}$=7.8 Hz), 157.3, 161.9 (J$_{C-F}$=249.5 Hz), 168.4.

3-(3-fluoro-6-Iodophenyl)-1,2,4,5-tetrazine (UB-153). The compound was obtained from 3-Fluoro-6-iodobenzonitrile (0.99 g, 4.00 mmol) following general procedure C. The resulting residue was purified using flash chromatography (95/5 Heptane/EtOAc) to yield 0.25 g (21%) of UB-153 as a red solid. R.f.=0.37 (Heptane/EtOAc 80/20); m.p.=$^{1}$H-NMR (CDCl$_3$, 400 MHz): 7.00 (ddd, J=3.0, 7.8, 8.7 Hz, 1H, Ar—H), 7.64 (dd, J=3.0, 8.8 Hz, 1H, Ar—H), 7.64 (dd, J=5.3, 8.8 Hz, 1H, Ar—H), 10.26 (s, 1H, Ar—H); $^{13}$C-NMR (CDCl$_3$, 100 MHz): δ8.5 (J$_{C-F}$=3.6 Hz), 119.1 (J$_{C-F}$=24.5 Hz), 120.1 (J$_{C-F}$=21.6 Hz), 138.3 (J$_{C-F}$=7.7 Hz), 142.6 (J$_{C-F}$=7.5 Hz), 157.3, 162.9 (J$_{C-F}$=250.3 Hz), 169.1 (J$_{C-F}$=2.5 Hz).

3-(6-hydroxy-3-fluorophenyl)-1,2,4,5-tetrazine (UB-122). The compound was obtained from 3-Fluoro-6-hydroxybenzonitrile (0.55 g, 4.00 mmol) following general procedure C. The crude was purified using flash chromatography (70/30 Heptane/EtOAc) to yield 0.18 g (23%) of UB-122 as a red crystals. R.f.=0.37 (Heptane/EtOAc 80/20), mp=° C.; $^1$H-NMR (CDCl$_3$, 400 MHz): 7.10 (dd, J=4.6, 9.2 Hz, 1H, Ar—H), 7.28 (ddd, J=3.2, 7.4, 9.2 Hz, 1H, Ar—H), 8.33 (dd, J=3.2, 9.3 Hz, 1H, Ar—H), 10.35 (s, 1H, Ar—H), 10.89 (br s, 1H, OH); $^{13}$C-NMR (CDCl$_3$, 100 MHz): 137.9 (J$_{C-F}$=25.6 Hz), 114.0 (J$_{C-F}$=8.3 Hz), 120.3 (J$_{C-F}$=7.7 Hz), 123.3 (J$_{C-F}$=23.9 Hz), 156.3 (J$_{C-F}$=239.8 Hz), 156.7 (J$_{C-F}$=1.7 Hz), 157.1, 166.7 (J$_{C-F}$=3.1 Hz).

General Procedure C.2 for synthesis of
3-H-6-aryl-1,2,4,5-tetrazine.[2]

Formamidine acetate (1.04 g, 10 mmol), Zn(OTf)$_2$ (182 mg, 0.5 mmol), Hydrazine Monohydrate (2.52 mL 50 mmol) along with the appropriate nitrile (1 mmol) were added to a microwave vial equipped with a stir bar and sealed. The reaction was allowed to stir at 30° C. for 24 hours before being allowed to cool to room temperature and unsealed. NaNO$_2$ (1.35 g, 20 mmol) in water (6 mL) was added to the now yellow mixture followed by the dropwise addition of HCl (2M) until gas evolution ceased and a pH of 3 was achieved producing a mixture red in colour. The mixture was then extracted with EtOAc, washed with brine, dried with MgSO$_4$, filtered before concentrating in vacuo. The tetrazine was then purified via flash chromatography utilising heptane and EtOAc in various mixtures as the eluent.

3-(4-fluorophenyl)-1,2,4,5-tetrazine (8): Starting Material 120 mg; The product was purified as a purple solid using flash chromatography (n-Heptane:EtOAc=8:1) Yield: 42%; Rf: 0.75; 1H (400 Hz, CDCl$_3$) δ 10.14 (s, 1H), 8.58 (m, 2H), 7.24 (m, 2H); $^{13}$C NMR (400 Hz, CDCl$_3$) δ 167.36, 165.25 (d, J=83.98 Hz), 157.73, 130.70 (d, J=8.82 Hz), 127.82, 116.67 (d, J=21.64 Hz); UPLCMS [M+H] m/z calc. for [C$_8$H$_6$FN$_4$]$^+$: 177.05; Found: 177.34.

3-(4-Iodophenyl)-1,2,4,5-tetrazine (14): Starting Material 229 mg; The product was purified as a purple solid using flash chromatography (n-Heptane:EtOAc=8:1) Yield: 90 mg (32%); Rf: 0.91; 1H (400 Hz, CDCl$_3$) δ 10.17 (s, 1H), 8.28 (d, J=8.61 Hz, 2H), 7.91 (d, J=8.61 Hz 2H); $^{13}$C NMR (400 Hz, CDCl$_3$) δ 166.20, 157.93, 138.73, 131.07, 129.59, 101.06; UPLCMS [M+H] m/z calc. for [C$_8$H$_6$IN$_4$]$^+$: 284.96; Found: 299.45.

3-(3-fluorophenyl)-1,2,4,5-tetrazine (9): Starting Material 120 mg; The product was purified as a purple solid using flash chromatography (n-Heptane:EtOAc=8:1) Yield: 15%; Rf 0.75; $^1$H (400 Hz, CDCl$_3$) δ 10.18 (s, 1H), 8.37 (m, 1H), 8.26 (m, 1H), 7.52 (m, 1H) 7.29 (m, 1H); $^{13}$C NMR (400 Hz, CDCl$_3$) δ 165.71 (d, J=3.36 Hz) 163.31 (d, J=247.50 Hz), 158.01, 133.75 (d, J=8.15 Hz) 131.07 (d, J=8.17 Hz), 124.02 (d, J=3.41 Hz), 120.20 (d, J=21.27 Hz), 115.17 (d, J=24.42 Hz); UPLCMS [M+H] m/z calc. for [C$_8$H$_6$FN$_4$]$^+$: 177.05; Found: 177.54.

3-(3-Iodophenyl)-1,2,4,5-tetrazine (15): Starting Material 229 mg; The product was purified as a purple solid using flash chromatography (n-Heptane:EtOAc=8:1) Yield: 90 mg (32%); Rf: 0.91; $^1$H NMR (600 Hz, CDCl$_3$) δ 10.17 (s, 1H), 8.93 (s, 1H), 8.54 (d, J=8.53 Hz, 1H) 7.93 (d, J=8.67 Hz, 1H) 7.29 (t, J=7.86, 15.8 Hz); $^{13}$C NMR (600 MHz, CDCl$_3$) δ 165.33, 158.03, 141.97, 137.07, 133.49, 130.94, 127.37, 94.87; UPLCMS [M+H] m/z calc. for [C$_8$H$_6$IN$_4$]$^+$: 284.96; Found: 285.32.

Synthesis of the triflate (16).[3]

-continued

Pyridine (20 μL, 0.25 mmol) was added to a mixture of 3-(4-hydroxy)-6-methyl-1,2,4,5-tetrazine (25 mg, 0.13 mmol) in anhydrous DCM. The solution was cooled to 0° C. followed by the slow addition of Trifluoromethanesulfonic anhydride (30 μL, 0.16 mmol). The reaction was allowed to stir at room temperature until TLC showed full conversion of the starting material (around 30 minutes). The solution was then diluted with Et₂O before being quenched with HCl (2M) followed by washing with NaHCO₃ and Brine, successively. The mixture was dried with MgSO₄, filtered and concentrated in vacuo before purification via flash chromatography utilising n-heptane and EtOAc (5%) as the eluent Yield: 40 mg (95%); Rf 0.9; $^1$H NMR (600 Hz, CDCl₃) δ 8.65 (d, J=9.05 Hz, 2H), 7.45 (d, J=9.07 Hz, 2H), 3.06 (s, H); $^{13}$C NMR (600 Hz, CDCl₃) δ 166.75, 161.88, 151.40, 131.06, 129.01, 121.30, 118.79, 20.21; UPLCMS [M+H] m/z calc. for $[C_{10}H_8F_3N_4O_3S]^+$: 321.02; Found: 321.38. General Synthesis of Organotin Compounds.

General Procedure D.1. Synthesis of Organotin Compounds (Me₃Sn)₂, Pd(OAc)₂, PA-Ph
⟶
THF, 45 min, 70° C.

Palladium acetate (4.5 mg, 12%) and 1,3,5,7-Tetramethyl-2,4,8-trioxa-(2,4-dimethoxyphenyl)-6-phosphaadamantane (PA-Ph) (9.8 mg, 20%) dry THF (1.5 mL) and Hexamethylditin (75 μL, 137 mg, 0.42 mmol, 2.5 equiv.) were successively added to a microwave vial equipped with a stir bar which was then sealed and purged with N2. A solution of the appropriate Iodo-phenyl-1,2,4,5-tetrazine (0.17 mmol) in dry THF (1 mL) was added via a syringe and the reaction allowed to stir at 70° C. in a microwave for 45 minutes. The reaction was allowed to cool to room temperature and unsealed before being quenched with saturated aqueous KF (1 mL). The solution was extracted with CH₂Cl2 washed with brine, dried with MgSO₄, filtered before concentrating in vacuo. The tetrazine was then purified via automatic flash chromatography utilising n-Heptane and EtOAc as the eluent.

3-(4-trimethyltin)-6-methyl-1,2,4,5-tetrazine (18) (RGV_57): Starting Material 50 mg; The product was purified as a purple solid using flash chromatography (n-Heptane:EtOAc=19:1) Yield: 27 mg (61%); Rf: 0.75; $^1$H NMR (400 Hz, CDCl₃) δ 10.13 (s, 1H), 8.48 (d, J=8.52 Hz, 2H), 7.67 (d, J=8.15 Hz, 2H) 0.29 (s, 9H); $^{13}$C NMR (400 MHz, CDCl₃) δ 166.85, 157.80, 150.19, 131.25, 130.14, 128.28, 127.20, −9.47; UPLCMS [M+H] m/z calc. for $[C_{11}H_{15}SnN_4]^+$: 323.04; Found: 323.38.

3-(3-trimethyltin)-1,2,4,5-tetrazine (19) (RGV_54): Starting Material 50 mg; The product was purified as a purple solid using flash chromatography (n-Heptane:EtOAc=19:1). Yield: 28 mg (58%); Rf: 0.9; $^1$H NMR (400 Hz, CDCl₃) δ 10.14 (s, 1H), 8.67 (s, 1H), 8.48 (s, J=7.95 Hz, 1H) 7.72 (d, J=7.51 Hz, 1H) 7.50 (t, J=7.86, 15.8 Hz, 1H) 0.30 (s, 9H); $^{13}$C NMR (400 MHz, CDCl₃) δ 166.83, 157.75, 144.16, 140.60, 135.48, 130.96, 128.74 128.17, −9.38; UPLCMS [M+H] m/z calc. for $[C_{11}H_{15}SnN_4]^+$: 323.04; Found: 323.38.

3-(4-methoxy-3-(trimethylstannyl)phenyl)-1,2,4,5-tetrazine (RGV_109). Starting Material 50 mg. The crude was purified using flash chromatography (90/10 Heptane/EtOAc) to yield 20 mg (36%) of RGV_106 as pink crystals. Rf: 0.28 (nHeptane:10% EtOAc); 1H NMR (400 Hz, CDCl3) δ 8.67-8.65 (m, 2H), δ 8.59 (d, J=8.13 Hz, 2H), δ 7.76 (d, J=8.15 Hz, 2H), δ 8.67-8.65 (m, 3H), δ 0.37 (s, 9H);

$^{13}$C NMR (600 MHz, CDCl$_3$) δ 164.47, 164.13, 149.66, 136.88, 132.80, 132.00, 131.62, 129.46, 128.11, 127.08, −9.32.

3-(2-methoxy-5-(trimethylstannyl)phenyl)-1,2,4,5-tetrazine (RGV_110). Starting Material 50 mg. The crude was purified using flash chromatography (90/10 Heptane/EtOAc) to yield 23 mg (40%) of RGV_110 as pink crystals. Rf: 0.16 (nHeptane:10% EtOAc); 1H NMR (600 MHz, Chloroform-d) δ 10.21 (s, 1H), 8.11-7.92 (m, 1H), 7.75-7.58 (m, 1H), 7.19-7.05 (m, 1H), 3.90 (s, 3H), 0.32 (s, 9H); $^{13}$C NMR (151 MHz, CDCl$_3$) δ 168.91, 158.89, 156.86, 141.13, 139.19, 133.70, 122.09, 112.20, 56.11, −9.19;

3-phenyl-6-(4-(trimethylstannyl)phenyl)-1,2,4,5-tetrazine (RGV_26). Starting Material 50 mg. The crude was purified using flash chromatography (90/10 Heptane/EtOAc) to yield 52 mg (95%) of RGV_26 as pink crystals. Rf=0.48 (nHeptane:10% EtOAc); 1H NMR (400 Hz, CDCl3) δ 8.67-8.65 (m, 2H), δ 8.59 (d, J=8.13 Hz, 2H), δ 7.76 (d, J=8.15 Hz, 2H), δ 8.67-8.65 (m, 3H), δ 0.37 (s, 9H); $^{13}$C NMR (600 MHz, CDCl$_3$) δ 164.47, 164.13, 149.66, 136.88, 132.80, 132.00, 131.62, 129.46, 128.11, 127.08, −9.32;

3-phenyl-6-(3-(trimethylstannyl)phenyl)-1,2,4,5-tetrazine (RGV_25). Starting Material 50 mg. The crude was purified using flash chromatography (90/10 Heptane/EtOAc) to yield 53 mg (95%) of RGV_125 as pink crystals. Rf=0.48 (nHeptane:10% EtOAc); $^1$H NMR (600 MHz, Chloroform-d) δ 8.78 (dt, J=1.7, 0.7 Hz, 1H), 8.69-8.65 (m, 2H), 8.59 (ddd, J=7.9, 2.0, 1.3 Hz, 1H), 7.77 (dt, J=7.2, 1.2 Hz, 1H), 7.65-7.61 (m, 3H), 7.58 (ddd, J=7.8, 7.2, 0.6 Hz, 1H), 0.38 (s, 9H); $^{13}$C NMR (600 MHz, CDCl$_3$) δ 164.44, 164.06, 144.19, 140.31, 135.34, 132.82, 131.98, 131.28, 129.47, 128.87, 128.10, 128.01, −9.24;

3-(pyridin-2-yl)-6-(4-(trimethylstannyl)phenyl)-1,2,4,5-tetrazine (RGV_46). Starting Material 50 mg. The crude was purified using flash chromatography (60/40 Heptane/EtOAc) to yield 14 mg (49%) of RGV_46 as pink crystals. The reduced form never isolated, it oxidized directly. Rf=0.31 (EtOAc:n-Heptane, 1:1); 1H NMR (600 Hz, CDCl3) δ 8.99-8.95 (m, 1H), δ 8.69 (dt, J=7.93, J=1.02 Hz, 1H), δ 8.65-8.60 (m, 2H), δ 8.00 (td, J=7.79, J=7.77, J=1.75, 1H), δ 7.77-7.76 (m, 2H), δ 7.57-7.55 (m, 1H), δ 0.37 (s, 9H).

3-(pyridin-2-yl)-6-(5-(trimethylstannyl)pyridin-2-yl)-1,2,4,5-tetrazine (RGV_60). Starting Material 50 mg. The crude was purified using flash chromatography (70/30 Heptane/EtOAc) to yield 47 mg (85%) as an orange oil which slowly solidified when stored in the freezer; Rf=0.50 (EtOAc-heptane, 1:2); $^1$H NMR (400 MHz, Chloroform-d) δ 8.62-

8.51 (m, 4H), 8.05 (dt, J=8.0, 1.1 Hz, 1H), 7.97 (dd, J=7.7, 1.1 Hz, 1H), 7.84 (dd, J=7.7, 1.5 Hz, 1H), 7.75 (td, J=7.7, 1.7 Hz, 1H), 7.34 (ddd, J=7.5, 4.9, 1.2 Hz, 1H), 0.36 (s, 9H); $^{13}$C NMR (101 MHz, CDCl$_3$) δ 154.24, 148.52, 147.74, 147.18, 147.10, 146.81, 144.22, 139.76, 136.82, 124.95, 121.41, 121.02, −9.35.

The 1,2-dihydro-1,2,4,5-tetrazine stannate was dissolved in dry CH2Cl2 and cooled to 0° C., followed by the portion wise addition of (Diacetoxyiodo)benzene (1.2 equiv.). The reaction was allowed to warm to r.t. and was stirred for 3 h. Celite was added to the mixture and the mixture was concentrated. The crude was purified using flash chromatography.

General Procedure D.2. Synthesis of Organotin Compounds

Palladium acetate (2.1 mg, 6%) and 1,3,5,7-Tetramethyl-2,4,8-trioxa-(2,4-dimethoxyphenyl)-6-phosphaadamantane (PA-Ph) (5.7 mg, 12%) dry THF (1.5 mL) and Hexamethylditin (137 mg, 0.42 mmol, 75 µL) were successively added to a microwave vial equipped with a stir bar which was then sealed and purged with N2. A solution of the appropriate iodo-phenyl-tetrazine (0.17 mmol) in dry THF (1 mL) was added via a syringe and the reaction allowed to stir at 70° C. in a microwave for 30 minutes. The reaction was allowed to cool to room temperature and unsealed before being quenched with saturated aqueous KF (1 mL). The solution was extracted with DCM, filtered and concentrated in vacuo before purification via flash chromatography utilising n-heptane and EtOAc as the eluent.

3-(4-trimethyltin)-6-methyl-1,2,4,5-tetrazine        (5) (RGV_6): Starting Material 50 mg; The product was purified as a purple solid using flash chromatography (n-Heptane:EtOAc=19:1). Yield: 46 mg (76%); Rf: 0.9; $^1$H NMR (400 Hz, CDCl$_3$) δ 8.44 (d, J=8.02 Hz, 2H), 7.65 (d, J=7.90 Hz, 2H), 3.01 (s, 3H), 0.28 (s, 9H); $^{13}$C NMR (400 Hz, CDCl$_3$) δ 167.21, 164.42, 149.17, 136.63, 131.49, 126.89, 21.17, −9.47; UPLCMS [M+H] m/z calc. for [C$_{12}$H$_{17}$SnN$_4$]$^+$: 337.04; Found: 337.45.

3-(3-trimethyltin)-6-methyl-1,2,4,5-tetrazine        (17) (RGV_51): Starting Material 50 mg; The product was purified as a purple solid using flash chromatography (n-Heptane:EtOAc=19:1) Yield: 32 mg (65%); Rf: 0.92; $^1$H (400 Hz, CDCl$_3$) δ 8.62 (s, 1H), 8.44 (d, J=7.95 Hz, 1H) 7.67 (d, J=7.12 Hz, 1H) 7.48 (t, J=7.57, 15.04 Hz, 1H), 3.02 (s, 3H), 0.29 (s, 9H); $^{13}$C NMR (400 MHz, CDCl$_3$) δ 167.15, 164.42, 143.91, 140.00, 135.10, 131.15, 128.63, 127.80, 21.15, −9.40. UPLCMS [M+H] m/z calc. for [C$_{12}$H$_{17}$SnN$_4$]$^+$: 337.04; Found: 337.38.

General Procedure D.3. Synthesis of Organotin Compounds

Pd(PPh3)4 (19.4 mg, 10%) and Hexamethylditin (87 µL, 0.42 mmol, 2.5 equiv) were successively added to a microwave vial equipped with a stir bar which was then sealed and purged with N$_2$. A solution of the appropriate Iodo-phenyl-1,2,4,5-tetrazine (0.17 mmol) in dry THF (2.5 mL) was added via a syringe and the reaction allowed to stir at 65° C. in a microwave for 3 hours. The reaction was allowed to cool to room temperature and unsealed before being quenched with saturated aqueous KF (1 mL). The solution was extracted with CH$_2$Cl$_2$ washed with brine, dried with MgSO$_4$, filtered before concentrating in vacuo. The tetrazine was then purified via automatic flash chromatography utilising n-Heptane and EtOAc as the eluent.

3-(3-methyl-5-(trimethylstannyl)phenyl)-1,2,4,5-tetra-zine (RGV_123). Starting Maternal 50 mg. The crude was purified using flash chromatography (90/10 Heptane/EtOAc) to yield 25 mg (27%) of RGV_0.123 as pink crystals. Rf=0.34 (nHeptane:20% EtOAc); $^1$H NMR (400 MHz, Chloroform-d) δ 10.20 (s, 1H), 8.65-8.50 (in, 1H), 8.48-8.33 (in, 1H), 7.73-7.43 (m, 1H), 2.48 (s, 3H), 0.38 (s, 9H); $^{13}$C NMR (151 MHz, CDCl$_3$) δ 167.05, 157.86, 144.08, 141.58, 138.56, 132.79, 131.00, 128.91, 21.58, −9.25.

In table 3 below, results are summarised for reactions with various substituents when one of the above-mentioned general procedures is followed:

R = -I, -F, -Sn(Me)$_3$

TABLE 3

| Substituent | Position | | |
|---|---|---|---|
| | 4 | 5 | 6 |
| -CH$_3$ | ok | ok | ok |
| -CF$_3$ | ok | ok | No reaction product detected |
| -Cl | ok | ok | ok |
| -Br | ok | ok | ok |
| -I | ok | ok | ok |
| -OH | ok | ok | ok |
| -OCH$_3$ | ok | ok | ok |
| -COOH | ok | ok | No reaction product detected |
| -COOCH$_3$ | ok | ok | No reaction product detected |
| -COOtBu | ok | ok | No reaction product detected |
| -CONH$_2$ | ok | ok | No reaction product detected |
| -NH$_2$ | ok | ok | ok |
| -NHCOCH$_3$ | ok | ok | ok |
| -CH$_2$NH$_2$ | ok | ok | ok |

Compounds that were derivatized in ortho-position (6) did not show detectable reaction when they had a strong electro withdrawing effect.

The following example illustrates the optimization of reaction conditions:

$$\text{Cu(OTf)}_2, \text{pyridine, [}^{18}\text{F]KF} \atop \text{DMA, time, temperature}$$

1. Conditions: Cu(OTf)$_2$, pyridine, [$^{18}$F]KF, DMA, 100° C., 50 ug K$_2$~CO$_3$

| Entry | Reaction time [min] | RCC [%] | | | RCC [%] |
|---|---|---|---|---|---|
| 1 | 1 | 0 | 0 | 0 | 0 |
| 2 | 3 | 34.61 | 17.37 | 26.79 | 26.25 |
| 3 | 5 | 26.46 | 30.08 | 36.6 | 26.16 | 29.83 |
| 4 | 10 | 11.84 | 10.80 | 24.34 | 12.20 | 14.80 |
| 5 | 15 | 17.60 | 15.92 | 14.09 | 15.87 |

2. Conditions: Cu(OTf)$_2$, pyridine, [$^{18}$F]KF, DMA, 5 min, 50 ug K$_2$CO$_3$

| Entry | Temperature [° C.] | RCC [%] | | | RCC [%] |
|---|---|---|---|---|---|
| 1 | 60 | 0 | 0 | 0 | 0 |
| 2 | 80 | 12.31 | 26.13 | 8.02 | 15.54 |
| 3 | 100 | 26.46 | 30.08 | 36.6 | 26.16 | 29.83 |
| 4 | 115 | 16.64 | 18.35 | 23.82 | 22.41 | 20.31 |
| 5 | 130 | 11.52 | 12.70 | 17.17 | 13.65 | 13.76 |

3. Conditions: Cu(OTf)$_2$, pyridine, [$^{18}$F]KF, DMA, 5 min, 100° C.

| Entry | Base amount [µg] | RCC [%] | | | RCC [%] |
|---|---|---|---|---|---|
| 0 | 0 | 28.81 | | | |
| 1 | 25 | 31.26 | 28.81 | 26.79 | 28.95 |
| 2 | 50 | 26.46 | 30.08 | 36.6 | 26.16 | 29.83 |
| 3 | 100 | 20.08 | 17.75 | 16.30 | 18.04 |
| 4 | 150 | 23.02 | 13.39 | 24.10 | 20.17 |
| 5 | 200 | 10.02 | 9.94 | 8.22 | 9.39 |

Reactivity

The compounds below have been syntheses using the general schemes i.e. starting from the iodine version, and via the Sn(Me)$_3$ reaching the F compound:

—CH₂—NH₂, —CH₂—NH-alkyl, —OH, CH₂—O-alkyl, CH₂—O-aryl, CH₂—O-phenyl, CH₂—O-naphthyl, and wherein n is an integer from 1 to 4, and R₆ is selected from H, CH₃, unsubstituted phenyl, wherein the curly bond indicates a link to the tetrazine moiety.

2. A compound according to claim 1, wherein alkyl is selected from linear or branched C₁-C₆ alkyl and cyclic C₁-C₆ alkyl, optionally substituted with —OH, —NH₂ or halogen.

3. A compound according to claim 1, wherein alkyl is selected from linear or branched methyl, ethyl, propyl, isopropyl, butyl, isobutyl, tert, butyl, pentyl, and hexyl.

4. A compound according to claim 1, wherein halogen is selected from I, Br, and Cl.

5. A compound according to claim 1, wherein R₁-R₆ are selected from:

a) R₁ is ¹⁸F and R₂-R₆ are H;

b) R₂ is ¹⁸F and R₁ and R₃-R₆ are H; and c) R3 is ¹⁸F and R₁-R₂ and R₄-R₆ are H.

6. A compound according to claim 1, wherein R₁-R₆ are selected from:

a) R₁ is ¹⁸F and R₂, R₃, R₄, and R₅ are H, and R₆ is selected from H, b) R₂ is ¹⁸F and R₁, R₃, R₄ and R₅ are H, and R₆ is selected from H, and c) R₃ is ¹⁸F and R₁, R₂, R₄, and R₅ are H, and R₆ is selected from H,

---

R = -I, -F, -Sn(Me)₃

In FIG. 9 the compounds are ranked according to their reactivity with increasing reactivity moving to the right.

The invention claimed is:

1. A tetrazine compound comprising a tetrazine moiety and having the following Formula I:

Formula I wherein:

one of R₁-R₅ is ¹⁸F, at least two of the remaining R₁-R₅ are H, and the other remaining R₁-R₅ are the same or different and are selected from H, alkyl, halogen, —CF₃, —CN, —O-alkyl, —S-alkyl, —NH-alkyl, —N(alkyl)₂, —NH(C═O)-alkyl, —N-alkyl-(C═O)-alkyl, —SO₂-alkyl, —SO₂—NH₂, —SO₂—NHalkyl, —SO₂—N(alkyl)₂-C(═O)—NH₂, —C(═O)—NH-alkyl, —C(═O)—N(alkyl)₂, —C(═O)—OH, —C(═O)—O-alkyl,

7. A bioorthogonal chemistry method, comprising administering a compound according to claim 1 to a subject.

8. A diagnostic method, comprising administering a compound according to claim 1 to a subject.

9. An in vivo imagining method, comprising administering a compound according to claim 1 to a subject.

10. A compound according to claim 1, wherein the compound is able to the blood-brain-barrier of a human subject.

11. A method for preparing a compound according to claim 1, wherein the method comprises reacting formamidine acetate and hydrazine monohydrate with a nitrile in the presence of $Zn(OTf)_2$.

12. A method according to claim 11, wherein the method comprises reacting in the presence of hydrazine monohydrate to obtain the tetrazine compound, wherein:

one of $R_1$-$R_5$ is $^{18}F$, at least two of the remaining $R_1$-$R_5$ are H, and the other remaining $R_1$-$R_5$ are the same or different and are selected from H, alkyl, halogen, —$CF_3$, —CN, —O-alkyl, —S-alkyl, —NH-alkyl, —$N(alkyl)_2$, —NH(C=O)-alkyl, —N-alkyl-(C=O)-alkyl, —$SO_2$-alkyl, —$SO_2$—$NH_2$, —$SO_2$—NHalkyl, —$SO_2$—$N(alkyl)_2$-C(=O)—$NH_2$, —C(=O)—NH-alkyl, —C(=O)—N(alkyl)$_2$, —C(=O)—OH, —C(=O)—O-alkyl, —$CH_2$—$NH_2$, —$CH_2$—NH-alkyl, —OH, $CH_2$—O-alkyl, $CH_2$—O-aryl, $CH_2$—O-phenyl, $CH_2$—O-naphthyl, and wherein n is an integer from 1 to 4, and $R_6$ is selected from H, $CH_3$, unsubstituted phenyl, and, wherein the curly bond indicates a link to the carbon atom.

13. A method according to claim 11, wherein the reaction is carried out at a temperature in a range of from 50° C. to 70° C.

14. A method according to claim 12, further comprising cooling to room temperature, adding water, subsequently adding HCl, and extracting with EtOAc.

15. A compound according to claim 1, wherein $R_2$ or $R_4$ is $^{18}F$.

16. A compound according to claim 1, wherein $R_2$ is $^{18}F$ and $R_1$ and $R_3$-$R_6$ are H.

17. A compound according to claim 1, wherein $R_3$ is $^{18}F$ and $R_1$-$R_2$ and $R_4$-$R_6$ are H.

18. A tetrazine compound comprising a tetrazine moiety and having the following Formula I:

Formula I wherein:

$R_2$ or $R_4$ is $^{18}F$, at least two of $R_1$-$R_5$ are H, and the other remaining $R_1$-$R_5$ are the same or different and are selected from H, alkyl, halogen, —$CF_3$, —CN, —O—alkyl, —S—alkyl, —NH—alkyl, $N(alkyl)_2$, —NH(C=O)—alkyl, —N—alkyl—(C=O)—alkyl, —$SO_2$—alkyl, —$SO_2$—$NH_2$, —$SO_2$—NHalkyl, —$SO_2$—$N(alkyl)_2$—C(=O)—$NH_2$, —C(=O)—NH—alkyl, —C(=O)—N(alkyl)$_2$, —C(=O)—OH, —C(=O)—O—alkyl, —$CH_2$—$NH_2$, —$CH_2$—NH—alkyl, —OH, $CH_2$—O—alkyl, $CH_2$—O—aryl, $CH_2$—O—phenyl, $CH_2$—O—naphthyl, and wherein n is an integer from 1 to 4, and $R_6$ is selected from H, $CH_3$, phenyl, wherein the curly bond indicates a link to the tetrazine moiety.

19. A tetrazine compound comprising a tetrazine moiety and having the following Formula II:

Formula II wherein:

$R_7$ is selected from —$CH_2$—$NH_2$, —$CH_2$—NH—alkyl, —C(=O)—$NH_2$, —C(=O)NH—alkyl, —NH—CH(=O), —NH—C(=O)—alkyl, —OH, —O—alkyl, —$CH_2$—O—alkyl, —$CH_2$—O—phenyl, —$CH_2$—O—naphthalene, —$CH_2$—C(=O)$NH_2$, and —$CH_2$—C(=O)—NH—alkyl.

* * * * *